US008652816B2

(12) United States Patent
Lynch

(10) Patent No.: US 8,652,816 B2
(45) Date of Patent: Feb. 18, 2014

(54) COMPOSITIONS AND METHODS FOR 3-HYDROXYPROPIONATE BIO-PRODUCTION FROM BIOMASS

(75) Inventor: Michael D. Lynch, Boulder, CO (US)

(73) Assignee: OPX Biotechnologies, Inc., Boulder, CO (US)

( * ) Notice: Subject to any disclaimer, the term of this patent is extended or adjusted under 35 U.S.C. 154(b) by 0 days.

(21) Appl. No.: 13/284,337

(22) Filed: Oct. 28, 2011

(65) Prior Publication Data

US 2012/0041232 A1 Feb. 16, 2012

Related U.S. Application Data

(63) Continuation of application No. 12/328,588, filed on Dec. 4, 2008, now Pat. No. 8,048,624.

(60) Provisional application No. 60/992,290, filed on Dec. 4, 2007.

(51) Int. Cl.
*C12P 7/62* (2006.01)

(52) U.S. Cl.
USPC ......... 435/135; 435/6; 435/320.1; 435/252.3; 435/136

(58) Field of Classification Search
None
See application file for complete search history.

(56) References Cited

U.S. PATENT DOCUMENTS

| | | |
|---|---|---|
| 2,408,889 A | 10/1946 | Short |
| 2,464,768 A | 3/1949 | Redmon et al. |
| 2,469,701 A | 5/1949 | Redmon |
| 2,798,053 A | 7/1957 | Brown et al. |
| 3,904,685 A | 9/1975 | Shahidi et al. |
| 3,915,921 A | 10/1975 | Schlatzer, Jr. |
| 4,029,577 A | 6/1977 | Godlewski et al. |
| 4,268,641 A | 5/1981 | Koenig et al. |
| 4,301,266 A | 11/1981 | Muenster et al. |
| 4,431,547 A | 2/1984 | Dubin |
| 4,666,983 A | 5/1987 | Tsubakimoto et al. |
| 4,685,915 A | 8/1987 | Hasse et al. |
| 4,708,997 A | 11/1987 | Stanley, Jr. et al. |
| 4,734,478 A | 3/1988 | Tsubakimoto et al. |
| 4,857,610 A | 8/1989 | Chmelir et al. |
| 4,985,518 A | 1/1991 | Alexander et al. |
| 5,009,653 A | 4/1991 | Osborn, III |
| 5,093,472 A | 3/1992 | Bresciani |
| 5,135,677 A | 8/1992 | Yamaguchi et al. |
| 5,145,906 A | 9/1992 | Chambers et al. |
| 5,180,798 A | 1/1993 | Nakamura et al. |
| 5,331,059 A | 7/1994 | Engelhardt et al. |
| 5,342,899 A | 8/1994 | Graham et al. |
| 5,350,799 A | 9/1994 | Woodrum et al. |
| 5,426,199 A | 6/1995 | Lundquist |
| 5,470,928 A | 11/1995 | Harwood et al. |
| 5,510,307 A | 4/1996 | Narayanan et al. |
| 5,510,526 A | 4/1996 | Baniel et al. |
| 5,558,656 A | 9/1996 | Bergman |
| 5,723,639 A | 3/1998 | Datta et al. |
| 5,817,870 A | 10/1998 | Haas et al. |
| 5,827,255 A | 10/1998 | Crainic |
| 5,876,983 A | 3/1999 | Sugimoto et al. |
| 6,004,773 A | 12/1999 | Araki et al. |
| 6,087,140 A | 7/2000 | Cameron et al. |
| 6,284,495 B1 | 9/2001 | Sato et al. |
| 6,297,319 B1 | 10/2001 | Nagasuna et al. |
| 6,472,188 B1 | 10/2002 | Lee et al. |
| 6,534,679 B2 | 3/2003 | Eyal et al. |
| 6,623,944 B2 | 9/2003 | Rieping |
| 6,709,919 B2 | 3/2004 | Tu |
| 6,723,799 B2 | 4/2004 | Sun et al. |
| 6,852,517 B1 | 2/2005 | Suthers et al. |
| 6,960,455 B2 | 11/2005 | Livshits et al. |
| 7,090,008 B2 | 8/2006 | Read |
| 7,141,154 B2 | 11/2006 | Lin et al. |
| 7,153,663 B2 | 12/2006 | Payne et al. |
| 7,166,743 B2 | 1/2007 | Zhong et al. |
| 7,186,541 B2 * | 3/2007 | Gokarn et al. ............... 435/232 |
| 7,186,856 B2 | 3/2007 | Meng et al. |
| 7,223,567 B2 | 5/2007 | Ka-Yiu et al. |
| 7,279,598 B2 | 10/2007 | Meng et al. |
| 7,285,406 B2 | 10/2007 | Payne et al. |
| 7,309,597 B2 | 12/2007 | Liao et al. |
| 7,326,557 B2 | 2/2008 | San et al. |
| 7,358,071 B2 | 4/2008 | Payne et al. |
| 7,393,676 B2 | 7/2008 | Gokarn et al. |
| 7,538,247 B2 | 5/2009 | Craciun et al. |
| 7,638,316 B2 * | 12/2009 | Gokarn et al. ............... 435/135 |
| 7,678,869 B2 | 3/2010 | Matyjaszewski et al. |
| 7,687,661 B2 * | 3/2010 | Lilga et al. ................... 560/212 |
| 7,833,761 B2 | 11/2010 | Terashita et al. |
| 7,943,362 B2 | 5/2011 | Frost |
| 8,076,111 B2 | 12/2011 | Fukui et al. |
| 2002/0164729 A1 | 11/2002 | Skraly et al. |
| 2003/0101046 A1 | 5/2003 | Facciotti et al. |
| 2003/0191146 A1 | 10/2003 | Kabbash et al. |
| 2003/0211131 A1 | 11/2003 | Martin et al. |

(Continued)

FOREIGN PATENT DOCUMENTS

| | | |
|---|---|---|
| EP | 1124789 B1 | 9/2004 |
| EP | 1036190 B1 | 5/2005 |

(Continued)

OTHER PUBLICATIONS

Alber et al. (J. of Bacter., vol. 188, No. 24, Dec. 2006, pp. 8551-8559).*

(Continued)

*Primary Examiner* — Hope Robinson
(74) *Attorney, Agent, or Firm* — Wilson Sonsini Goodrich & Rosati

(57) ABSTRACT

Methods of obtaining mutant nucleic acid sequences that demonstrate elevated oxaloacetate α-decarboxylase activity are provided. Compositions, such as genetically modified microorganisms that comprise such mutant nucleic acid sequences, are described, as are methods to obtain the same.

15 Claims, 18 Drawing Sheets

(56) References Cited

U.S. PATENT DOCUMENTS

| | | |
|---|---|---|
| 2003/0233675 A1 | 12/2003 | Cao et al. |
| 2003/0235892 A1 | 12/2003 | Katz et al. |
| 2004/0076982 A1 | 4/2004 | Gokam et al. |
| 2004/0152159 A1 | 8/2004 | Causey et al. |
| 2004/0152174 A1 | 8/2004 | Cervin et al. |
| 2004/0209337 A1 | 10/2004 | Frost et al. |
| 2004/0210087 A1 | 10/2004 | Meng et al. |
| 2004/0214294 A1 | 10/2004 | Rieping |
| 2005/0054060 A1 | 3/2005 | Chateau et al. |
| 2005/0196758 A1 | 9/2005 | Rock et al. |
| 2005/0222458 A1 | 10/2005 | Craciun et al. |
| 2005/0239179 A1 | 10/2005 | Skraly et al. |
| 2005/0283029 A1 | 12/2005 | Meng et al. |
| 2006/0014977 A1 | 1/2006 | Miller et al. |
| 2006/0084098 A1 | 4/2006 | Gill et al. |
| 2007/0010708 A1 | 1/2007 | Ness |
| 2007/0087403 A1 | 4/2007 | Bestel-Corre et al. |
| 2007/0107080 A1 | 5/2007 | Liao et al. |
| 2007/0148749 A1 | 6/2007 | Yasuda et al. |
| 2007/0184524 A1 | 8/2007 | Gokarn et al. |
| 2007/0219390 A1 | 9/2007 | Zacher et al. |
| 2007/0245431 A1 | 10/2007 | Metz et al. |
| 2008/0076167 A1 | 3/2008 | Gokarn et al. |
| 2008/0124785 A1 | 5/2008 | Liao et al. |
| 2008/0193989 A1 | 8/2008 | Verser et al. |
| 2008/0199926 A1 | 8/2008 | Burgard et al. |
| 2009/0017514 A1 | 1/2009 | Datta et al. |
| 2009/0031453 A1 | 1/2009 | Jessen et al. |
| 2009/0053783 A1* | 2/2009 | Gokarn et al. ............ 435/141 |
| 2009/0076297 A1 | 3/2009 | Bogan, Jr. et al. |
| 2009/0082286 A1 | 3/2009 | Huang et al. |
| 2009/0111151 A1 | 4/2009 | Julien et al. |
| 2009/0234146 A1 | 9/2009 | Cooney et al. |
| 2009/0291480 A1 | 11/2009 | Jessen et al. |
| 2009/0298144 A1 | 12/2009 | Tsobanakis et al. |
| 2009/0305369 A1 | 12/2009 | Donaldson et al. |
| 2009/0325248 A1 | 12/2009 | Marx et al. |
| 2010/0151536 A1 | 6/2010 | Baynes et al. |
| 2010/0210017 A1 | 8/2010 | Gill et al. |
| 2011/0105791 A1* | 5/2011 | Kuppinger et al. ........... 562/599 |
| 2011/0125118 A1* | 5/2011 | Lynch ............................ 604/367 |
| 2011/0183391 A1 | 7/2011 | Frost |
| 2011/0244575 A1 | 10/2011 | Lipscomb et al. |
| 2011/0275851 A1 | 11/2011 | Orjuela et al. |
| 2012/0244586 A1* | 9/2012 | Gokarn et al. ............ 435/135 |

FOREIGN PATENT DOCUMENTS

| | | |
|---|---|---|
| EP | 1305439 B1 | 6/2006 |
| EP | 1124979 B1 | 8/2006 |
| EP | 1731604 A1 | 12/2006 |
| EP | 1105514 B1 | 2/2008 |
| EP | 1778840 B1 | 6/2008 |
| EP | 1975236 A2 | 10/2008 |
| EP | 1654212 B1 | 7/2009 |
| EP | 1975236 A3 | 9/2009 |
| EP | 1706457 B1 | 2/2012 |
| JP | H 09-505463 | 6/1997 |
| WO | WO 98/21339 A1 | 5/1998 |
| WO | WO 98/55442 A1 | 12/1998 |
| WO | WO 00/56693 A1 | 9/2000 |
| WO | WO 01/16346 A1 | 3/2001 |
| WO | WO 01/38284 A1 | 5/2001 |
| WO | WO 02/42418 A2 | 5/2002 |
| WO | WO 03/040690 A2 | 5/2003 |
| WO | WO 02/42418 A3 | 6/2003 |
| WO | WO 03/062173 A2 | 7/2003 |
| WO | WO 2004/018621 A2 | 3/2004 |
| WO | WO 2004/033646 A2 | 4/2004 |
| WO | WO 2004/018621 A3 | 9/2004 |
| WO | WO 03/040690 A3 | 10/2004 |
| WO | WO 2005/003074 A1 | 1/2005 |
| WO | WO 2005/047498 A1 | 5/2005 |
| WO | WO 03/062173 A3 | 11/2005 |
| WO | WO 2005/105770 A2 | 11/2005 |
| WO | WO 2005/118719 A2 | 12/2005 |
| WO | WO 2005/105770 A3 | 3/2006 |
| WO | WO 2004/033646 A3 | 5/2006 |
| WO | WO 2005/118719 A3 | 9/2006 |
| WO | WO 2006/121755 A2 | 11/2006 |
| WO | WO 2007/012078 A1 | 1/2007 |
| WO | WO 2007/030830 A2 | 3/2007 |
| WO | WO 2007/042494 A2 | 4/2007 |
| WO | WO 2007/047680 A2 | 4/2007 |
| WO | WO 2006/121755 A3 | 6/2007 |
| WO | WO 2007/030830 A3 | 10/2007 |
| WO | WO 2007/042494 A3 | 11/2007 |
| WO | WO 2007/047680 A3 | 11/2007 |
| WO | WO 2008/027742 A1 | 3/2008 |
| WO | WO 2008/028002 A1 | 3/2008 |
| WO | WO 2008/089102 A2 | 7/2008 |
| WO | WO 2008/091627 A2 | 7/2008 |
| WO | WO 2008/089102 A3 | 1/2009 |
| WO | WO 2009/031737 A1 | 3/2009 |
| WO | WO 2008/091627 A3 | 5/2009 |
| WO | WO 2009/062190 A2 | 5/2009 |
| WO | WO 2009/094485 A1 | 7/2009 |
| WO | WO 2009/062190 A3 | 9/2009 |
| WO | WO 2011/038364 A1 | 3/2011 |
| WO | WO 2011/063363 A2 | 5/2011 |
| WO | WO 2011/063363 A3 | 8/2011 |
| WO | WO 2011/094457 A1 | 8/2011 |

OTHER PUBLICATIONS

Asano, et al. A new enzymatic method of acrylamide production. Agricultural and Biological Chemistry. 1982; 46(5):1183-1190.

Brown, et al. Synthesis of labeled acrylamide and N-methylolacrylamide (NMA) : 15N-acrylamide, 13C-NMA, 15N-NMA, and 13C,15N-NMA. Journal of labelled compounds & radiopharmaceuticals. 2005; 48(14):1031-1039.

Kurcok, et al. Reactions of β-lactones with potassium alkoxides and their complexes with 18-crown-6 in aprotic solvents. Journal of Organic Chemistry. 1993; 58(16):4219-4220.

Langlois, et al. A new preparation of trifluoromethanesulfinate salts. Journal of Fluorine Chemistry. 2007; 128(7):851-856.

Liang, et al. $Fe_2(SO_4)_3 \cdot 4H_2O$/concentrated $H_2SO_4$: an efficient catalyst for esterification. Journal of Chemical Research, Synopses. 2004; 3:226-227.

Orjuela, et al. Presentation: Recovery of succinic acid from fermentative broth through esterification with ethanol. Department of Chemical Engineering and Materials Science. Michigan State University. East Lansing, Michigan 48824. Jun. 29, 2010.

Ramalinga, et al. A mild and efficient method for esterification and transesterification catalyzed by iodine. Tetrahedron Letters. 2002; 43(5):879-882.

Ren, et al. Molecular Iodine in Ionic Liquid: A Green Catalytic System for Esterification and Transesterification. Synthetic Communications. 2010; 40(11):1670-1676.

Rodriguez, et al. Structure-cytoprotective activity relationship of simple molecules containing an alpha,beta-unsaturated carbonyl system. J Med Chem. Jun. 6, 1997;40(12):1827-34.

Sun, et al. $ZrOC_{12} \times 8H_2O$: an efficient, cheap and reusable catalyst for the esterification of acrylic acid and other carboxylic acids with equimolar amounts of alcohols. Molecules. Apr. 10, 2006;11(4):263-71.

U.S. Appl. No. 13/527,799, filed Jun. 20, 2012, Tengler et al.

Dell'Aquila, et al. Acid-base balance in peritoneal dialysis. J Nephrol. Mar.-Apr. 2006;19 Suppl 9:S104-7.

Duncan, et al. Lactate-utilizing bacteria, isolated from human feces, that produce butyrate as a major fermentation product. Appl Environ Microbiol. Oct. 2004;70(10):5810-7.

Kozliak, et al. Expression of proteins encoded by the *Escherichia coli* cyn operon: carbon dioxide-enhanced degradation of carbonic anhydrase. J Bacteriol. Sep. 1994;176(18):5711-7.

Kozliak, et al. Role of bicarbonate/$CO_2$ in the inhibition of *Escherichia coli* growth by cyanate. J Bacteriol. Jun. 1995;177(11):3213-9.

(56) References Cited

OTHER PUBLICATIONS

Meng, et al. Nucleotide sequence of the *Escherichia coli* cad operon: a system for neutralization of low extracellular pH. J Bacteriol. Apr. 1992;174(8):2659-69.

Moreau. The lysine decarboxylase CadA protects *Escherichia coli* starved of phosphate against fermentation acids. J Bacteriol. Mar. 2007;189(6):2249-61. Epub Jan. 5, 2007.

Stim, et al. Nucleotide sequence of the adi gene, which encodes the biodegradative acid-induced arginine decarboxylase of *Escherichia coli*. J Bacteriol. Mar. 1993;175(5):1221-34.

Turlin, et al. 3-phenylpropionate catabolism and the *Escherichia coli* oxidative stress response. Res Microbiol. Apr. 2005;156(3):312-21. Epub Jan. 27, 2005.

Warnecke, et al. Identification of a 21 amino acid peptide conferring 3-hydroxypropionic acid stress-tolerance to *Escherichia coli*. Biotechnol Bioeng. May 2012;109(5):1347-52. doi: 10.1002/bit.24398. Epub Jan. 2, 2012.

U.S. Appl. No. 13/416,103, filed Mar. 9, 2012, Lipscomb et al.
U.S. Appl. No. 13/498,468, filed Mar. 27, 2012, Lynch.

Agriculture Project Fact Sheet. U.S. Department of Energy, Office of Industrial Technologies. 2001. Chemicals From Lignocellulose, http://www.oit.doe.gov/agriculture/factsheets/lignocellulose.pdf (Apr. 21, 2004).

Bailey, et al. Inverse metabolic engineering: A strategy for directed genetic engineering of useful phenotypes. BBiotechnol Bioeng. Sep. 5, 2002;79(5):568-79.

Bailey. Toward a science of metabolic engineering. Science. Jun. 21, 1991;252(5013):1668-75.

Beguin et al. The biological degradation of cellulose. FEMS Microbiol Rev. Jan. 1994;13(1):25-58.

Chotani, et al. The commercial production of chemicals using pathway engineering. Biochim Biophys Acta. Dec. 29, 2000;1543(2):434-455.

Crameri, et al. DNA shuffling of a family of genes from diverse species accelerates directed evolution . Nature. Jan. 15, 1998;391(6664):288-91.

De Mendoza, et al Thermal regulation of membrane lipid fluidity in bacteria. Trends Biochem. Sci. 1983; 8:49-52.

Energetics Incorporated. 2003. Industrial Bioproducts: Today and Tomorrow. U.S. Department of Energy, Office of Energy Efficiency and Renewable Energy, Office of the Biomass Program, Washington, D.C.

Eppink, et al. Switch of coenzyme specificity of p-hydroxybenzoate hydroxylase. J Mol Biol. Sep. 10, 1999;292(1):87-96.

Epstein, et al. Oil: A Life Cycle Analysis of its Health and Environmental Impacts. The Center for Health and the Global Environment, Harvard Medical School. Mar. 2002. www.med.harvard.edu/chge/oil.html.

Farmer, et al. Improving lycopene production in *Escherichia coli* by engineering metabolic control. Nat Biotechnol. May 2000;18(5):533-7.

Fodor, et al. Light-Directed, Spatially Addressable Parallel Chemical Synthesis. Science. Feb. 15, 1991;251(4995):767-73.

Gronenborn. Overproduction of phage lambda repressor under control of the lac promotor of *Escherichia coli*. Mol Gen Genet. Nov. 17, 1976;148(3):243-50.

Li, et al. Effect of poxB gene knockout on metabolism in *Escherichia coli* based on growth characteristics and enzyme activities. World Journal of Microbiology and Biotechnology V 23(4). Apr. 2007. p. 573-580.

Martin, et al. Engineering a mevalonate pathway in *Escherichia coli* for production of terpenoids. Nat Biotechnol. Jul. 2003;21(7):796-802. Epub Jun. 1, 2003.

Ohmiya, et al. Structure of cellulases and their applications. Biotechnol Genet Eng Rev. 1997;14:365-414.

Ohnishi, et al. A novel methodology employing *Corynebacterium glutamicum* genome information to generate a new L-lysine-producing mutant. Appl Microbiol Biotechnol. Feb. 2002;58(2):217-23.

Patnaik, et al. Genome shuffling of *Lactobacillus* for improved acid tolerance. Nat Biotechnol. Jul. 2002;20(7):707-12.

Pohl et al. A new perspective on thiamine catalysis. Curr Opin Biotechnol. Aug. 2004;15(4):335-42.

Schmidt-Dannert, et al. Molecular breeding of carotenoid biosynthetic pathways. Nat Biotechnol. Jul. 2000;18(7):750-3.

Service. Sugary Recipe Boosts Grow-Your-Own Plastics. Science. Jun. 30. 2006;312(5782):1861.

Stephanopoulos, et al. Network Rigidity and Metabolic Engineering in Metabolite Overproduction. Science. Jun. 21, 1999;252(5013):1675-81.

Stephanopoulos. Challenges in engineering microbes for biofuels production. Science. Feb. 9, 2007;315(5813):801-4.

Tunnicliff, et al. The inhibition by substrate analogues of gamma-aminobutyrate aminotransferase from mitochondria of different subcellular fractions of rat brain. Can J Biochem. Apr. 1977;55(4):479-84.

U.S. Appl. No. 12/891,760, filed Sep. 27, 2010, Lynch.
U.S. Appl. No. 12/891,790, filed Sep. 27, 2010, Lynch.
U.S. Appl. No. 13/062,917, filed Mar. 8, 2011, Lynch.

Alber, et al. Malonyl-coenzyme A reductase in the modified 3-hydroxypropionate cycle for autotrophic carbon fixation in archaeal *Metallosphaera* and *Sulfolobus spp*. J Bacteriol. Dec. 2006;188(24):8551-9.

Barbin, et al. Induction of specific base-pair substitutions in *E. coli* trpA mutants by chloroethylene oxide, a carcinogenic vinyl chloride metabolite. Mutat Res. Nov.-Dec. 1985;152(2-3):147-56.

Bastian, et al. Engineered ketol-acid reductoisomerase and alcohol dehydrogenase enable anaerobic 2-methylpropan-1-ol production at theoretical yield in *Escherichia coli*. Metab Eng. May 2011;13(3):345-52.

Bergler et al. Sequences of the envM gene and of two mutated alleles in *Escherichia coli*. J Gen Microbiol. Oct. 1992;138(10):2093-100.

Brock, et al. Naturally occurring adenines within mRNA coding sequences affect ribosome binding and expression in *Escherichia coli*. J Bacteriol. Jan. 2007;189(2):501-10. Epub Nov. 3, 2006.

Bunch, et al. The ldhA gene encoding the fermentative lactate dehydrogenase of *Escherichia coli*. Microbiology. Jan. 1997;143 ( Pt 1):187-95.

Canada, et al. Directed evolution of toluene ortho-monooxygenase for enhanced 1-naphthol synthesis and chlorinated ethene degradation. J Bacteriol. Jan. 2002;184(2):344-9.

Chang, et al. Acetate metabolism in a pta mutant of *Escherichia coli* W3110: importance of maintaining acetyl coenzyme A flux for growth and survival. J Bacteriol. Nov. 1999;181(21):6656-63.

Cleusix, et al. Inhibitory activity spectrum of reuterin produced by *Lactobacillus reuteri* against intestinal bacteria. BMC Microbiol. Nov. 12, 2007;7:101.

Cowan, et al. Characterization of the major promoter for the plasmid-encoded sucrose genes scrY, scrA, and scrB. J Bacteriol. Dec. 1991;173(23):7464-70.

Cronan, et al. Genetic and biochemical analyses of pantothenate biosynthesis in *Escherichia coli* and *Salmonella typhimurium*.J Bacteriol. Mar. 1982;149(3):916-22.

Cronan, J.E., Beta-Alanine Synthesis in *Escherichia coli* J Bacteriol. Mar. 1980;141(3):1291-7.

Den, et al. Enzymatic Conversion of β-Hydroxypropionate to Malonic Semialdehyde. J Biol Chem Jul. 1959;234(7):1666-1671.

Dohr, et al. Engineering of a functional human NADH-dependent cytochrome P450 system. Proc Natl Acad Sci U S A. Jan. 2, 2001;98(1):81-6.

Drake, et al. Structure of the EntB multidomain nonribosomal peptide synthetase and functional analysis of its interaction with the EntE adenylation domain. Chem Biol. Apr. 2006;13(4):409-19.

European search report dated Jul. 2, 2010 for Application No. 08727619.2.

Funa, et al. A novel quinone-forming monooxygenase family involved in modification of aromatic polyketides. J Biol Chem. Apr. 15, 2005;280(15):14514-23. Epub Feb. 8, 2005.

GenBank Accession No. X81461 AF473544 (Sep. 7, 1994).
GenBank Accession No. AAS20429.1 (Jan. 19, 2004).

Gill, et al. Genome-wide screening for trait conferring genes using DNA microarrays. Proc Natl Acad Sci U S A. May 14, 2002;99(10):7033-8. Epub May 7, 2002.

(56) References Cited

OTHER PUBLICATIONS

Gokarn, et al. Metabolic analysis of *Escherichia coli* in the presence and absence of the carboxylating enzymes phosphoenolpyruvate carboxylase and pyruvate carboxylase. Appl Environ Microbiol. May 2000;66(5):1844-50.
Goodwin, et al. Purification and characterization of methylmalonate-semialdehyde dehydrogenase from rat liver. Identity to malonate-semialdehyde dehydrogenase. J Biol Chem. Sep. 5, 1989;264(25):14965-71.
Gulmezian, et al. Genetic evidence for an interaction of the UbiG O-methyltransferase with UbiX in *Escherichia coli* coenzyme Q biosynthesis. J Bacteriol. Sep. 2006;188(17):6435-9.
Hall, et al. Structure-function analysis of NADPH:nitrate reductase from *Aspergillus nidulans*: analysis of altered pyridine nucleotide specificity in vivo. Microbiology. Jun. 2000;146 ( Pt 6):1399-406.
Hatzimanikatis, et al. Exploring the diversity of complex metabolic networks. Bioinformatics. Apr. 15, 2005;21(8):1603-9. Epub Dec. 21, 2004.
He, et al. A T42M substitution in bacterial 5-enolpyruvylshikimate-3-phosphate synthase (EPSPS) generates enzymes with increased resistance to glyphosate. Biosci Biotechnol Biochem. Jun. 2003;67(6):1405-9.
Heath, et al. Enoyl-acyl carrier protein reductase (fabI) plays a determinant role in completing cycles of fatty acid elongation in *Escherichia coli*.J Biol Chem. Nov. 3, 1995;270(44):26538-42.
Henry, et al. Discovery of novel routes for the biosynthesis of industrial chemicals: 3-Hydroxypropanoate. Slides. AICHE Annual Meeting. Nov. 8, 2007. Salt Lake City, UT.
Herter, et al. Autotrophic $CO_2$ Fixation by *Chloroflexus aurantiacus*: Study of Glyoxylate Formation and Assimilation via the 3-Hydroxypropionate Cycle. J Bacteriol Jul. 2001;183(14):4305-4316.
Hondorp et al. Oxidation of cysteine 645 of cobalamin-independent methionine synthase causes a methionine limitation in *Escherichia coli*. J Bacteriol. May 2009;191(10):3407-10. Epub Mar. 13, 2009.
Hügler, et al. Malonyl-Coenzyme A Reductase from *Chloroflexus aurantiacus*, a Key Enzyme of the 3-Hydroxypropionate Cycle for Autotrophic $CO_2$ Fixation. J Bacteriol May 2002;184(9):2404-2410.
International search report and written report dated Jun. 3, 2011 for PCT Application No. US2010/057690.
International search report dated Feb. 3, 2011 for PCT Application No. US2010/050436.
International search report dated Jun. 4, 2010 for PCT Application No. US2009/51607.
International search report dated Jun. 16, 2011 for PCT Application No. US2011/022790.
International search report dated Dec. 5, 2008 for PCT Application No. US08/50921.
International search report dated Apr. 29, 2010 for PCT Application No. US2009/57058.
Joike, et al. Amino acid substitutions affecting catalytic activity and subunit interactions of aminodeoxychorismate synthase in *E. coli*. Abstracts of the General Meeting of the American Society for Microbiology. 2002; 102:275-276, and 102nd General Meeting of the American Society for Microbiology; Salt Lake, UT, USA; May 19-23, 2002.
Kapol, et al. Purification and characterization of 2-oxoglutarate decarboxylase of *Leuconostoc oenos*. Journal of General Microbiology 136 (1990), 1497-1499.
Kern, et al. Engineering primary metabolic pathways of industrial micro-organisms. J Biotechnol. Mar. 30, 2007;129(1):6-29. Epub Dec. 2, 2006.
Kim et al. Extractive Recovery of Products from Fermentation Broths. Biotechnol. Bioprocess Eng., 1999; 4:1-11.
Kim, et al. The Rut pathway for pyrimidine degradation: novel chemistry and toxicity problems. J Bacteriol. Aug. 2010;192(16):4089-102. Epub Apr. 16, 2010.
Kim, et al. Dihydrolipoamide dehydrogenase mutation alters the NADH sensitivity of pyruvate dehydrogenase complex of *Escherichia coli* K-12. J Bacteriol. Jun. 2008;190(11):3851-8. Epub Mar. 28, 2008.
Kim, et al. Effect of overexpression of *Actinobacillus succinogenes* phosphoenolpyruvate carboxykinase on succinate production in *Escherichia coli*. Appl Environ Microbiol. Feb. 2004;70(2):1238-41.
Kwon, et al. A physiology study of *Escherichia coli* overexpressing phosphoenolpyruvate carboxykinase. Biosci Biotechnol Biochem. Apr. 2008;72(4):1138-41.
Kwon, et al. Influence of Gluconeogenic Phosphoenolpyruvate Carboxykinase (PCK) Expression on Succinic Acid Fermentation in *Escherichia coli* Under High Bicarbonate Condition. Journal of Microbiology and Biotechnology. 2006; 16(9):1448-1452.
Lennen, et al. A process for microbial hydrocarbon synthesis: Overproduction of fatty acids in *Escherichia coli* and catalytic conversion to alkanes. Biotechnol Bioeng. Jun. 1, 2010;106(2):193-202.
Lipscomb, et al. Poster—Understanding production of 3-Hydroxypropionic Acid (3-HP) in a genomic context. OPX Biotechnologies. Metabolic Engineering. Sep. 17, 2008.
Lutke-Eversloh, et al. Feedback inhibition of chorismate mutase/prephenate dehydrogenase (TyrA) of *Escherichia coli*: generation and characterization of tyrosine-insensitive mutants. Appl Environ Microbiol. Nov. 2005;71(11):7224-8.
Lynch, et al. SCALEs: multiscale analysis of library enrichment. Nat Methods. Jan. 2007;4(1):87-93.
Lynch, M. Rapid optimization of microorganisms for the cost superior production of chemicals & fuels. OPX Biotechnologies. Sep. 15, 2008.
Magnuson et al. Regulation of fatty acid biosynthesis in *Escherichia coli*. Microbiol Rev. Sep. 1993;57(3):522-42.
Mehta, et al. Aminotransferases: demonstration of homology and division into evolutionary subgroups. Eur J Biochem. Jun. 1, 1993;214(2):549-61.
Mohan, et al. Effect of process parameters on 3-hydroxypropionic acid production from glycerol using a recombinant *Escherichia coli*. Appl Microbiol Biotechnol. Sep. 2009;84(4):649-57. Abstract only.
Moreau. Diversion of the metabolic flux from pyruvate dehydrogenase to pyruvate oxidase decreases oxidative stress during glucose metabolism in nongrowing *Escherichia coli* cells incubated under aerobic, phosphate starvation conditions. J Bacteriol. Nov. 2004;186(21):7364-8.
NCBI Reference Sequence: NP_414657.1 (Jan. 16, 1997).
NCBI Reference Sequence: NP_415792.1 (Jan. 16, 1997).
NCBI Reference Sequence: NP_416366.1 (Jan. 16, 1997).
NCBI Reference Sequence: NP_418812.1 (Jan. 16, 1997).
NCBI Reference Sequence: YP_001277512.1 (Jun. 6, 2007).
NCBI Reference Sequence: YP_001433009.1 (Sep. 4, 2007).
NCBI Reference Sequence: YP_001636209.1 (Dec. 21, 2007).
NCBI Reference Sequence: YP_002462600.1 (Dec. 29, 2008).
NCBI Reference Sequence: ZP_01039179.1 (Jan. 16, 2006).
NCBI Reference Sequence: ZP_01626393.1 (Dec. 15, 2006).
NCBI Reference Sequence: ZP_04957196.1 (Sep. 15, 2008).
NCBI Reference Sequence: ZP_05125944.1 (Sep. 15, 2008).
Nexant, Inc. Chemsystems Perp Program, Acrylic Acid, 08/09-3, Jul. 2010.
Office action dated Apr. 29, 2011 for U.S. Appl. No. 12/328,588.
Office action dated Jul. 4, 2011 for EP Applilcation No. 08727619.2.
Office action dated Sep. 17, 2010 for U.S. Appl. No. 12/328,588.
Okamura et al. Unprecedented acetoacetyl-coenzyme A synthesizing enzyme of the thiolase superfamily involved in the mevalonate pathway. Proc Natl Acad Sci U S A. Jun. 22, 2010;107(25):11265-70. Epub Jun. 7, 2010.
Ozcelik et al. Metabolic engineering of aromatic group amino acid pathway in *Bacillus subtilis* for L-phenylalanine production. Chemical Engineering Science. 2004;59(22-23):5019-5026.
Parikh, et al. Directed evolution of RuBisCO hypermorphs through genetic selection in engineered *E. coli*. Protein Eng Des Sel. Mar. 2006;19(3):113-9. Epub Jan. 19, 2006.
Ponce, et al. Cloning of the Two Pyruvate Kinase Isoenzyme StructuralGenes from *Escherichia coli*: the Relative Roles of These Enzymes in Pyruvate Biosynthesis. J Bacteriol. Oct. 1995;177(19):5719-22.

(56) References Cited

OTHER PUBLICATIONS

Raj, et al. Effect of process parameters on 3-hydroxypropionic acid production from glycerol using a recombinant *Escherichia coli*. Appl Microbiol Biotechnol. Sep. 2009;84(4):649-57. Epub Apr. 8, 2009.
Ray et al. Mutational analysis of the catalytic and feedback sites of the tryptophan-sensitive 3-deoxy-D-arabino-heptulosonate-7-phosphate synthase of *Escherichia coli*. J Bacteriol. Dec. 1988;170(12):5500-6.
Saier, et al. The catabolite repressor/activator (Cra) protein of enteric bacteria. J Bacteriol. Jun. 1996;178(12):3411-7.
Singh, et al. Genes restoring redox balance in fermentation-deficient *E. coli* NZN111. Metab Eng. Nov. 2009;11(6):347-54. Epub Jul. 21, 2009.
Straathoff, et al. Feasibility of acrylic acid production by fermentation. Appl Microbiol Biotechnol. Jun. 2005;67(6):727-34.
Strauss, et al. Enzymes of a novel autotrophic CO2 fixation pathway in the phototrophic bacterium *Chloroflexus aurantiacus*, the 3-hydroxypropionate cycle. Eur J Biochem. Aug. 1, 1993;215(3):633-43.
Tian, et al. *Mycobacterium tuberculosis* appears to lack an alpha-ketoglutarate dehydrogenase and encodes pyruvate dehydrogenase in widely separated genes. Mol Microbiol. Aug. 2005;57(3):859-68.
Tian, et al. Variant tricarboxylic acid cycle in *Mycobacterium tuberculosis*: Identification of alpha-ketoglutarate decarboxylase. Proc Natl Acad Sci U S A. Jul. 26, 2005;102(30):10670-5. Epub Jul. 18, 2005.
Vedantam, et al. Characterization of mutations contributing to sulfathiazole resistance in *Escherichia coli*. Antimicrob Agents Chemother. Jan. 1998;42(1):88-93.
Warnecke, et al. A genomics approach to improve the analysis and design of strain selections. Metab Eng. May-Jul. 2008;10(3-4):154-65.
Warnecke, et al. Organic acid toxicity, tolerance, and production in *Escherichia coli* biorefining applications. Microbial Cell Factories. 2005;4(25):1-8.
Warnecke, et al. Rapid dissection of a complex phenotype through genomic-scale mapping of fitness altering genes. Metab Eng. May 2010;12(3):241-50.
Wasewar, et al. Fermentation of Glucose to Lactic Acid Coupled with Reactive Extraction: A Review. Ind. Eng. Chem. Res. 2004; 43:5969-5982.
Werpy, et al. Pacific Northwest National Laboratory. Top Value Added Chemicals From Biomass, vol. 1—Results of Screening for Potential candidates From Sugars and Synthesis Gas, U.S. Department of Energy, Aug. 2004.
Yee, et al. On the role of helix 0 of the tryptophan synthetase alpha chain of *Escherichia coli*. J Biol Chem. Jun. 21, 1996;271(25):14754-63.
Yoshida, et al. Identification of PhoB binding sites of the yibD and ytfK promoter regions in *Escherichia coli*. J Microbiol. Apr. 2011;49(2):285-9. Epub May 3, 2011.
Zha, et al. Improving cellular malonyl-CoA level in *Escherichia coli* via metabolic engineering. Metab Eng. May 2009;11(3):192-8. Epub Feb. 5, 2009.
Zhao et al. Binding of two flaviolin substrate molecules, oxidative coupling, and crystal structure of *Streptomyces coelicolor* A3(2) cytochrome P450 158A2. J Biol Chem. Mar. 25, 2005;280(12):11599-607. Epub Jan. 19, 2005.
Zhou, et al. Interdomain communication between the thiolation and thioesterase domains of EntF explored by combinatorial mutagenesis and selection. Chem Biol. Aug. 2006;13(8):869-79.
U.S. Appl. No. 13/575,581, filed Jul. 26, 2012, Lynch.
Broun, et al. Catalytic plasticity of fatty acid modification enzymes underlying chemical diversity of plant lipids. Science. Nov. 13, 1998;282(5392):1315-7.
Chica, et al. Semi-rational approaches to engineering enzyme activity: combining the benefits of directed evolution and rational design. Curr Opin Biotechnol. Aug. 2005;16(4):378-84.

Cho, et al. Simultaneous synthesis of enantiomerically pure (S)-amino acids and (R)-amines using coupled transaminase reactions. Biotechnol Bioeng. Mar. 30, 2003;81(7):783-9.
Devos, et al. Practical limits of function prediction. Proteins. Oct. 1, 2000;41(1):98-107.
Ivanova, et al. Genome sequence of *Bacillus cereus* and comparative analysis with *Bacillus anthracis*. Nature. May 1, 2003;423(6935):87-91.
Kimchi-Sarfaty, et al. A "silent" polymorphism in the MDR1 gene changes substrate specificity. Science. Jan. 26, 2007;315(5811):525-8. Epub Dec. 21, 2006.
Kisselev. Polypeptide release factors in prokaryotes and eukaryotes: same function, different structure. Structure. Jan. 2002;10(1):8-9.
Nackley, et al. Human catechol-O-methyltransferase haplotypes modulate protein expression by altering mRNA secondary structure. Science. Dec. 22, 2006;314(5807):1930-3.
Office action dated Jul. 11, 2012 for U.S. Appl. No. 13/055,138.
Office action dated Aug. 29, 2012 for Chinese Application No. 200980137400.4 (in Chinese with English translation).
Office action dated Sep. 18, 2012 for U.S. Appl. No. 12/891,790.
Office action dated Sep. 19, 2012 for JP Application No. 2012-531103 (in Japanese with English translation).
Sauna, et al. Silent polymorphisms speak: how they affect pharmacogenomics and.The treatment of cancer. Cancer Res. Oct. 15, 2007;67(20):9609-12.
Seffernick, et al. Melamine deaminase and atrazine chlorohydrolase: 98 percent identical but functionally different. J Bacteriol. Apr. 2001;183(8):2405-10.
Sen, et al. Developments in directed evolution for improving enzyme functions. Appl Biochem Biotechnol. Dec. 2007;143(3):212-23.
Sousa, et al. The ARO4 gene of *Candida albicans* encodes a tyrosine-sensitive DAHP synthase: evolution, functional conservation and phenotype of Aro3p-, Aro4p-deficient mutants. Microbiology. May 2002;148(Pt 5):1291-303.
Whisstock, et al. Prediction of protein function from protein sequence and structure Q Rev Biophys. Aug. 2003;36(3):307-40.
Wishart, et al. A single mutation converts a novel phosphotyrosine binding domain into a dual-specificity phosphatase. J Biol Chem. Nov. 10, 1995;270(45):26782-5.
Witkowski, et al. Conversion of a beta-ketoacyl synthase to a malonyl decarboxylase by replacement of the active-site cysteine with glutamine. Biochemistry. Sep. 7, 1999;38(36):11643-50.
Cronk, et al. Cloning, crystallization and preliminary characterization of a beta-carbonic anhydrase from *Escherichia coli*. Acta Crystallogr D Biol Crystallogr. Sep. 2000;56(Pt 9):1176-9.
Diaz, et al. Characterization of the hca cluster encoding the dioxygenolytic pathway for initial catabolism of 3-phenylpropionic acid in *Escherichia coli* K-12. J Bacteriol. Jun. 1998;180(11):2915-23.
Figge, et al. Methionine biosynthesis is *Escherichia coli* and *Corynebacterium glutamicum*. Microbiol Monogro. 2007; 5:163-193.
Muday, et al. The tyrosine repressor negatively regulates aroH expression in *Escherichia coli*. Bacteriol. Jun. 1991;173(12):3930-2.
Office action dated Nov. 2, 2012 for U.S. Appl. No. 13/416,103.
Price-Carter, et al. Polyphosphate kinase protects *Salmonella enterica* from weak organic acid stress. Journal of Bacteriology. 2005; 187:3088-3099.
Ramey, et al. Poster—Translation of genomics data into useful metabolic engineering strategies: construction of a 3-hydroxypropionic acid tolerant *E. coli*. 2010.
Warnecke, et al. Engineering of Organic Acid Tolerance Genes in *E. coli* for Biorefinery Applications. 2006 AIChE Annual meeting in San Francisco, California, Nov. 12-17, 2006 https://aiche.confex.comlaiche/2006/techprogram/P67122.HTM.
European search report dated Jan. 3, 2013 for Application No. 09813810.0.
Office action dated Feb. 13, 2013 for U.S. Appl. No. 12/523,047.
Office action dated Feb. 20, 2013 for U.S. Appl. No. 12/891,760.
Ray, et al. Mutational analysis of the catalytic and feedback sites of the tryptophan-sensitive 3-deoxy-D-arabin-heptulosonate-7-phosphate synthase of *Escherichia coli*. J Bacteriol. Dec. 1988;170(12):5500-6.

(56) References Cited

OTHER PUBLICATIONS

U.S. Appl. No. 13/916,534, filed Jun. 12, 2013, Lynch.
Office action dated Jun. 3, 2013 for U.S. Appl. No. 13/416,103.
Office action dated Jun. 19, 2013 for U.S. Appl. No. 12/891,790.
Roe, et al. Inhibition of *Escherichia coli* growth by acetic acid: a problem with methionine biosynthesis and homocysteine toxicity. Microbiology. Jul. 2002;148(Pt 7):2215-22.
Welch, et al. Extensive mosaic structure revealed by the complete genome sequence of uropathogenic *Escherichia coli*. Proc Natl Acad Sci U S A. Dec. 24, 2002;99(26):17020-4. Epub Dec. 5, 2002.
Zhang, et al. Inhibiting bacterial fatty acid synthesis. J Biol Chem. Jun. 30, 2006;281(26):17541-4. Epub Apr. 28, 2006.
Anton, et al. Sequencing and overexpression of the *Escherichia coli* aroE gene encoding shikimate dehydrogenase. Biochem J. Jan. 15, 1998;249(2):319-26.
Dewick, P. Chapter 4. The Shikimate Pathway: Aromatic Amino Acids and Phenylpropanoids. Medicinal Natural Products: A Biosynthetic Approach, Second Edition (2002): 121-166.
Duncan, et al. The overexpression and complete amino acid sequence of *Escherichia coli* 3-dehydroquinase. Biochem J. Sep. 1, 1986;238(2):475-83.
Ginkel, et al. Identification and cloning of the *Mycobacterium avium* folA gene, required for dihydrofolate reductase activity. FEMS Microbiol Lett. Nov. 1, 1997;156(1):69-78.
Gray, et al. Monofunctional chorismate mutase from *Bacillus subtilis*: purification of the protein, molecular cloning of the gene, and overexpression of the gene product in *Escherichia coli*. Biochemistry. Jan. 16, 1990;29(2):376-83.
Jiang, et al. Cloning and Expression of aroG Gene of *E. coli* and Its Co-expression with pheA and tyrB Genes. Sheng Wu Hua Xue Yu Sheng Wu Wu Li Xue Bao (Shanghai). 1998;30(6):593-596. (In Chinese with English abstract).
Oliviera, et al. Cloning and overexpression in soluble form of functional shikimate kinase and 5-enolpyruvylshikimate 3-phosphate synthase enzymes from *Mycobacterium tuberculosis*. Protein Expr Purif. Aug. 2001;22(3):430-5.
White, et al. The overexpression, purification and complete amino acid sequence of chorismate synthase from *Escherichia coli* K12 and its comparison with the enzyme from *Neurospora crassa*. Biochem J. Apr. 15, 1988;251(2):313-22.
European search report and opinion dated Jul. 18, 2013 for EP Application No. 09801031.7.
Office action dated Sep. 19, 2013 for U.S. Appl. No. 13/055,138.

\* cited by examiner

FIG. 4B

| NUMBER | GENE |
|---|---|
| 1 | aroA |
| 2 | aroB |
| 3 | aroC |
| 4 | aroD |
| 5 | aroE |
| 6 | aroF |
| 7 | aroK |
| 8 | aroL |
| 9 | aspC |
| 10 | entC |
| 11 | entD |
| 12 | entE |
| 13 | folA |
| 14 | folD |
| 15 | menD |
| 16 | menE |
| 17 | menF |
| 18 | pabA |
| 19 | pabB |
| 20 | pheA |
| 21 | purN |
| 22 | trpA |
| 23 | trpD |
| 24 | tyrA |
| 25 | tyrB |
| 26 | ubiA |
| 27 | ubiB |
| 28 | ubiC |
| 29 | ubiE |
| 30 | ubiG |
| 31 | ubiH |
| 32 | ubiX |
| 33 | ydiB |

FIG. 10B

| | Minimal Media |
|---|---|
| E. coli AB354 | no growth |
| E. coli AB354 + gabT | no growth |
| E. coli AB354 + gabT + kgd | no growth |
| E. coli AB354 + gabT + mutant kgd pools | positive clones grow |

SEQUENCE LISTING

<160> NUMBER OF SEQ ID NOS: 23

<210> SEQ ID NO 1
<211> LENGTH: 3736
<212> TYPE: DNA
<213> ORGANISM: Artificial Sequence
<220> FEATURE:
<223> OTHER INFORMATION: Codon optimized kgd gene sequence with
      customized ends

<400> SEQUENCE: 1

```
ttgacggata tcaagcttct attaaccgaa cgcttcgtcc aagatttctt gctgctccac      60
ggcatgaacc ttcgaggaac cgctgctcgg cgcagacatc gcgcgacggg agatacgctt     120
gatgcccgcc aacttgtccg gcagcaactc cggcaactcc aaaccgaaac gcggccaggc     180
gccctggttc gctggttcct cctggaccca aaagaactct tgacattttt cgtaacgatc     240
cagggtttca cgcagacgac gacgcggcaa cggcgccagt tgctccagac gcacaattgc     300
cagatcatta cggttgtctt tcgccttgcg tgccgccaat tcataataca acttaccgga     360
ggtcaacaga atacggctaa ctttattgcg gtcgccgata ccatcctcgt aggtcggttc     420
ctccaggacg ctacggaatt taatctcggt aaaatcctta atctccgaaa ccgccgcctt     480
gtggcgcagc atggatttcg gggtaaacac gatcaacgga cgttggatgc cgtccaacgc     540
gtggcggcgc agcaagtgaa agtaattgga cggggtgctc ggcatcgcga tcgtcatgct     600
accctcagcc cacagctgca aaagcgctca atgcgcgcc gacgtgtggt ccgggccctg     660
accctcgtgg ccgtgtggca gcaacagaac aacgttggac agctgacccc atttcgcttc     720
gcccgagctg atgaactcgt caatgatcga ctgggcacca ttaacaaagt cgccgaattg     780
cgcctcccac agcacaaccg cgtctggatt gccaacggta taaccgtact caaaacccac     840
agccgcgtat tccgacaacg gcgaatcata aaccaggaac ttaccaccgg tcgggctgcc     900
gtcgctgtta gtcgccagca gctgcagcgg ggtgaactcc tcgccggtgt gacggtcgat     960
cagcacagaa tgacgctggc taaaggtgcc acgacgagag tcttgaccgc tcagacggac    1020
cagcttgccc tcagcaacca ggctgcccag cgccagcaac tcaccaaacg cccagtcaat    1080
cttaccctca tacgccatct cacgacgctt ttccagcacc ggctgaacgc gcgggtgtgc    1140
cgtgaaaccg ttaggcagcg ccaggaaggc atcaccgata cgtgccagca gggatttgtc    1200
aacagcggtc gccaggcccg ctgggatcat ttggtccgac tcgacgctct ccgacggttg    1260
gacgccgtgc ttctccagtt cgcgcacttc gttgaacaca cgctccagtt ggccctggta    1320
atcgcgcagc gcatcctccg cctctttcat gctgatgtcg ccacgaccga tcagagcctc    1380
ggtgtaggat ttacgggcgc cacgcttggt gtccacgacg tcatagacat acggattggt    1440
catagatgga tcgtcaccct cattatgacc acgacgacga tagcacagca tgtcaataac    1500
aacgtccttt ttaaagcgtt ggcggaagtc aactgccaaa cgcgcaaccc agacacacgc    1560
ttctggatcg tcgccgttca cgtggaagat tggcgcaccg atcatcttcg ccacatccgt    1620
gcagtactcg ctcgaacgag agtattccgg agcggtggtg aagccgattt ggttgttcac    1680
aatgatgtga atcgtaccac ccacacgata gccaggcaga tttgccagat tcagcgtctc    1740
cgcaacaacg ccttgacccg cgaaggccgc atcaccgtgc agcatcaacg aacgacgga    1800 gaatgcacgt tggccgtcgg agtcaatgga accgtggtcc agcaggtctt gcttcgcacg    1860
caccaaacct tccagcactg gatcgaccgc ttccaaatgg gacggatttg ccgtcaggga    1920
aacctgaata tcgttatcgc caaacatttg cagatacaga cccgtcgcac ccaggtggta    1980
```

-continued

```
cttgacatcg ccggaaccgt gagcctggga cgggttcaga ttgccttcaa actccgtaaa   2040
gatttgcgaa tacggtttgc ccacgatgtt cgccaggaca ttcaagcgac cacggtgcgg   2100
catgccaatg accacttcat ccaaaccatg ctcggcacat tggtcaatcg ccgcgtccat   2160
cattggaata acagattccg caccctccag gctaaaacgc ttttggccca catacttggt   2220
ttgcaggaag gtttcaaacg cctccgctgc gttcagtttc gacaagatgt acttttgttg   2280
agcaacggtc ggtttgacgt gcttcgtctc gacacgctgc tccagccact ccttttgttc   2340
cgggtccaga atgtgcgcgt actcaacacc gatgtgacgg cagtacgcgt cgcgcagcaa   2400
acccagcacg tcacgcagct tttgtattg agcacccgcg aaaccgtcaa ccttaaagac   2460
gcggtccagg tcccacagag tcaggccatg cgtcaacacc tccaaatccg gatgcgaacg   2520
aaagcgcgcc ttatccaagc gcaacgggtc ggtgtccgcc atcagatggc cgcggttgcg   2580
ataggccgcg atcaggttca tcacacgtgc gttcttgtca acgatcgagt ccggattatc   2640
ggtgctccaa cgcactggca ggtacgggat gctcagctcg cggaagacct catcccagaa   2700
gccatcagac aacagcagtt catgaatggt acgcaggaag tcaccgcttt ccgcaccttg   2760
aatgatacgg tggtcgtagg tagaagtcag ggtaatcagt ttgccaatac ccagctcagc   2820
gatgcgttcc tcggacgcgc cttggaactc cgccggatat tccatcgcac cgacaccgat   2880
gatagcacct tgacctggca tcaggcgtgg cacagagtgc accgtgccaa tcgtgcccgg   2940
attcgtcagc gaaatcgtaa cgccagcgaa gtcctcggtg gtcagtttac catcacgagc   3000
acgacggacg atgtcctcgt acgcggtaac gaactgcgcg aagcgcatcg tctcgcaacg   3060
tttgataccg gccaccacca gagagcgctt gccatcttta ccttgcaggt caatagccag   3120
acccagattg gtgtgcgcag gagtaaccgc cgtcggctta ccgtccacct ccgtgtagtg   3180
gcgattcata ttcgggaact tcttaaccgc ctgaaccaga gcataaccca gcaaatgggt   3240
aaagctgatt ttaccaccac gcgtgcgttt caactgatta ttgatcacga tacgattatc   3300
gatcaacaat ttcgctggca cagcacgcac cgaggtcgcc gtaggcactt ccagcgacgc   3360
gctcatgttc ttcacgacag cagccgccgc accacgcagg acagcaactt catcgccttc   3420
ggctggcgga ggcaccgcgg tcttggcggc cagagccgcc acgacaccgt tgcccgctgc   3480
ggccgtgtcg gccggtttcg gcggcgcttg cggagccgcc gctgccgcac gctcagcgac   3540
caaagggctg gtcacacgag tcggctcagc agccggttgg gaagtcggct ccgggctata   3600
gtccaccaga aactcatgcc agcttgggtc aacggaagac ggatcatcac gaaatttacg   3660
atacatacca acacgagacg ggtcctgagt caccatggat atatctcctt cttaaagaat   3720
tcgatatctc agcgac                                                    3736
```

<210> SEQ ID NO 2
<211> LENGTH: 1224
<212> TYPE: PRT
<213> ORGANISM: Mycobacterium tuberculosis

<400> SEQUENCE: 2

```
Met Val Thr Gln Asp Pro Ser Arg Val Gly Met Tyr Arg Lys Phe Arg
1               5                   10                  15

Asp Asp Pro Ser Ser Val Asp Pro Ser Trp His Glu Phe Leu Val Asp
            20                  25                  30

Tyr Ser Pro Glu Pro Thr Ser Gln Pro Ala Ala Glu Pro Thr Arg Val
        35                  40                  45

Thr Ser Pro Leu Val Ala Glu Arg Ala Ala Ala Ala Ala Pro Gln Ala
    50                  55                  60
```

-continued

```
Pro Pro Lys Pro Ala Asp Thr Ala Ala Gly Asn Gly Val Ala
65                  70                  75                  80

Ala Leu Ala Ala Lys Thr Ala Val Pro Pro Ala Glu Gly Asp Glu
                85                  90                  95

Val Ala Val Leu Arg Gly Ala Ala Ala Val Val Lys Asn Met Ser
            100                 105                 110

Ala Ser Leu Glu Val Pro Thr Ala Thr Ser Val Arg Ala Val Pro Ala
        115                 120                 125

Lys Leu Leu Ile Asp Asn Arg Ile Val Ile Asn Asn Gln Leu Lys Arg
130                 135                 140

Thr Arg Gly Gly Lys Ile Ser Phe Thr His Leu Leu Gly Tyr Ala Leu
145                 150                 155                 160

Val Gln Ala Val Lys Lys Phe Pro Asn Met Asn Arg His Tyr Thr Glu
                165                 170                 175

Val Asp Gly Lys Pro Thr Ala Val Thr Pro Ala His Thr Asn Leu Gly
            180                 185                 190

Leu Ala Ile Asp Leu Gln Gly Lys Asp Gly Lys Arg Ser Leu Val Val
        195                 200                 205

Ala Gly Ile Lys Arg Cys Glu Thr Met Arg Phe Ala Gln Phe Val Thr
210                 215                 220

Ala Tyr Glu Asp Ile Val Arg Arg Ala Arg Asp Gly Lys Leu Thr Thr
225                 230                 235                 240

Glu Asp Phe Ala Gly Val Thr Ile Ser Leu Thr Asn Pro Gly Thr Ile
                245                 250                 255

Gly Thr Val His Ser Val Pro Arg Leu Met Pro Gly Gln Gly Ala Ile
            260                 265                 270

Ile Gly Val Gly Ala Met Glu Tyr Pro Ala Glu Phe Gln Gly Ala Ser
        275                 280                 285

Glu Glu Arg Ile Ala Glu Leu Gly Ile Gly Lys Leu Ile Thr Leu Thr
290                 295                 300

Ser Thr Tyr Asp His Arg Ile Ile Gln Gly Ala Glu Ser Gly Asp Phe
305                 310                 315                 320

Leu Arg Thr Ile His Glu Leu Leu Leu Ser Asp Gly Phe Trp Asp Glu
                325                 330                 335

Val Phe Arg Glu Leu Ser Ile Pro Tyr Leu Pro Val Arg Trp Ser Thr
            340                 345                 350

Asp Asn Pro Asp Ser Ile Val Asp Lys Asn Ala Arg Val Met Asn Leu
        355                 360                 365

Ile Ala Ala Tyr Arg Asn Arg Gly His Leu Met Ala Asp Thr Asp Pro
370                 375                 380

Leu Arg Leu Asp Lys Ala Arg Phe Arg Ser His Pro Asp Leu Glu Val
385                 390                 395                 400

Leu Thr His Gly Leu Thr Leu Trp Asp Leu Asp Arg Val Phe Lys Val
                405                 410                 415

Asp Gly Phe Ala Gly Ala Gln Tyr Lys Lys Leu Arg Asp Val Leu Gly
            420                 425                 430

Leu Leu Arg Asp Ala Tyr Cys Arg His Ile Gly Val Glu Tyr Ala His
        435                 440                 445

Ile Leu Asp Pro Glu Gln Lys Glu Trp Leu Glu Gln Arg Val Glu Thr
450                 455                 460

Lys His Val Lys Pro Thr Val Ala Gln Gln Lys Tyr Ile Leu Ser Lys
465                 470                 475                 480

Leu Asn Ala Ala Glu Ala Phe Glu Thr Phe Leu Gln Thr Lys Tyr Val
```

```
                485                 490                 495
Gly Gln Lys Arg Phe Ser Leu Glu Gly Glu Ser Val Ile Pro Met
            500                 505                 510
Met Asp Ala Ala Ile Asp Gln Cys Ala Glu His Gly Leu Asp Glu Val
            515                 520                 525
Val Ile Gly Met Pro His Arg Gly Arg Leu Asn Val Leu Ala Asn Ile
            530                 535                 540
Val Gly Lys Pro Tyr Ser Gln Ile Phe Thr Glu Phe Glu Gly Asn Leu
545                 550                 555                 560
Asn Pro Ser Gln Ala His Gly Ser Gly Asp Val Lys Tyr His Leu Gly
                565                 570                 575
Ala Thr Gly Leu Tyr Leu Gln Met Phe Gly Asp Asn Asp Ile Gln Val
            580                 585                 590
Ser Leu Thr Ala Asn Pro Ser His Leu Glu Ala Val Asp Pro Val Leu
        595                 600                 605
Glu Gly Leu Val Arg Ala Lys Gln Asp Leu Leu Asp His Gly Ser Ile
    610                 615                 620
Asp Ser Asp Gly Gln Arg Ala Phe Ser Val Val Pro Leu Met Leu His
625                 630                 635                 640
Gly Asp Ala Ala Phe Ala Gly Gln Gly Val Val Ala Glu Thr Leu Asn
                645                 650                 655
Leu Ala Asn Leu Pro Gly Tyr Arg Val Gly Gly Thr Ile His Ile Ile
                660                 665                 670
Val Asn Asn Gln Ile Gly Phe Thr Thr Ala Pro Glu Tyr Ser Arg Ser
            675                 680                 685
Ser Glu Tyr Cys Thr Asp Val Ala Lys Met Ile Gly Ala Pro Ile Phe
            690                 695                 700
His Val Asn Gly Asp Asp Pro Glu Ala Cys Val Trp Val Ala Arg Leu
705                 710                 715                 720
Ala Val Asp Phe Arg Gln Arg Phe Lys Lys Asp Val Val Ile Asp Met
                725                 730                 735
Leu Cys Tyr Arg Arg Arg Gly His Asn Glu Gly Asp Asp Pro Ser Met
            740                 745                 750
Thr Asn Pro Tyr Val Tyr Asp Val Val Asp Thr Lys Arg Gly Ala Arg
        755                 760                 765
Lys Ser Tyr Thr Glu Ala Leu Ile Gly Arg Gly Asp Ile Ser Met Lys
    770                 775                 780
Glu Ala Glu Asp Ala Leu Arg Asp Tyr Gln Gly Gln Leu Glu Arg Val
785                 790                 795                 800
Phe Asn Glu Val Arg Glu Leu Glu Lys His Gly Val Gln Pro Ser Glu
                805                 810                 815
Ser Val Glu Ser Asp Gln Met Ile Pro Ala Gly Leu Ala Thr Ala Val
            820                 825                 830
Asp Lys Ser Leu Leu Ala Arg Ile Gly Asp Ala Phe Leu Ala Leu Pro
        835                 840                 845
Asn Gly Phe Thr Ala His Pro Arg Val Gln Pro Val Leu Glu Lys Arg
    850                 855                 860
Arg Glu Met Ala Tyr Glu Gly Lys Ile Asp Trp Ala Phe Gly Glu Leu
865                 870                 875                 880
Leu Ala Leu Gly Ser Leu Val Ala Glu Gly Lys Leu Val Arg Leu Ser
                885                 890                 895
Gly Gln Asp Ser Arg Arg Gly Thr Phe Ser Gln Arg His Ser Val Leu
            900                 905                 910
```

| | | | | | | | | | | | |
|---|---|---|---|---|---|---|---|---|---|---|---|
|Ile|Asp|Arg|His|Thr|Gly|Glu|Glu|Phe|Thr|Pro|Leu|Gln|Leu|Leu|Ala|
| |915| | | |920| | | |925| | | |

Ile Asp Arg His Thr Gly Glu Glu Phe Thr Pro Leu Gln Leu Leu Ala
    915                 920                 925

Thr Asn Ser Asp Gly Ser Pro Thr Gly Gly Lys Phe Leu Val Tyr Asp
930                 935                 940

Ser Pro Leu Ser Glu Tyr Ala Ala Val Gly Phe Glu Tyr Gly Tyr Thr
945                 950                 955                 960

Val Gly Asn Pro Asp Ala Val Val Leu Trp Glu Ala Gln Phe Gly Asp
                965                 970                 975

Phe Val Asn Gly Ala Gln Ser Ile Ile Asp Glu Phe Ile Ser Ser Gly
                980                 985                 990

Glu Ala Lys Trp Gly Gln Leu Ser Asn Val Val Leu Leu Leu Pro His
            995                1000                1005

Gly His Glu Gly Gln Gly Pro Asp His Thr Ser Ala Arg Ile Glu
   1010                1015                1020

Arg Phe Leu Gln Leu Trp Ala Glu Gly Ser Met Thr Ile Ala Met
   1025                1030                1035

Pro Ser Thr Pro Ser Asn Tyr Phe His Leu Leu Arg Arg His Ala
   1040                1045                1050

Leu Asp Gly Ile Gln Arg Pro Leu Ile Val Phe Thr Pro Lys Ser
   1055                1060                1065

Met Leu Arg His Lys Ala Ala Val Ser Glu Ile Lys Asp Phe Thr
   1070                1075                1080

Glu Ile Lys Phe Arg Ser Val Leu Glu Glu Pro Thr Tyr Glu Asp
   1085                1090                1095

Gly Ile Gly Asp Arg Asn Lys Val Ser Arg Ile Leu Leu Thr Ser
   1100                1105                1110

Gly Lys Leu Tyr Tyr Glu Leu Ala Ala Arg Lys Ala Lys Asp Asn
   1115                1120                1125

Arg Asn Asp Leu Ala Ile Val Arg Leu Glu Gln Leu Ala Pro Leu
   1130                1135                1140

Pro Arg Arg Arg Leu Arg Glu Thr Leu Asp Arg Tyr Glu Asn Val
   1145                1150                1155

Lys Glu Phe Phe Trp Val Gln Glu Glu Pro Ala Asn Gln Gly Ala
   1160                1165                1170

Trp Pro Arg Phe Gly Leu Glu Leu Pro Glu Leu Leu Pro Asp Lys
   1175                1180                1185

Leu Ala Gly Ile Lys Arg Ile Ser Arg Arg Ala Met Ser Ala Pro
   1190                1195                1200

Ser Ser Gly Ser Ser Lys Val His Ala Val Glu Gln Gln Glu Ile
   1205                1210                1215

Leu Asp Glu Ala Phe Gly
   1220

<210> SEQ ID NO 3
<211> LENGTH: 8621
<212> TYPE: DNA
<213> ORGANISM: Artificial Sequence
<220> FEATURE:
<223> OTHER INFORMATION: p206 plasmid with codon optimized kgd gene
      nucleic acid sequence and softag

<400> SEQUENCE: 3
ggtggcggta cttgggtcga tatcaaagtg catcacttct tcccgtatgc ccaactttgt      60
atagagagcc actgcgggat cgtcaccgta atctgcttgc acgtagatca cataagcacc     120
aagcgcgttg gcctcatgct tgaggagatt gatgagcgcg gtggcaatgc cctgcctccg     180

```
gtgctcgccg gagactgcga gatcatagat atagatctca ctacgcggct gctcaaactt    240
gggcagaacg taagccgcga gagcgccaac aaccgcttct tggtcgaagg cagcaagcgc    300
gatgaatgtc ttactacgga gcaagttccc gaggtaatcg gagtccggct gatgttggga    360
gtaggtggct acgtcaccga actcacgacc gaaaagatca agagcagccc gcatggattt    420
gacttggtca gggccgagcc tacatgtgcg aatgatgccc atacttgagc cacctaactt    480
tgttttaggg cgactgccct gctgcgtaac atcgttgctg ctccataaca tcaaacatcg    540
acccacggcg taacgcgctt gctgcttgga tgcccgaggc atagactgta caaaaaaaca    600
gtcataacaa gccatgaaaa ccgccactgc gccgttacca ccgctgcgtt cggtcaaggt    660
tctggaccag ttgcgtgagc gcatttttt ttcctcctcg gcgtttacgc cccgccctgc    720
cactcatcgc agtactgttg taattcatta agcattctgc cgacatggaa gccatcacag    780
acggcatgat gaacctgaat cgccagcggc atcagcacct tgtcgccttg cgtataatat    840
ttgcccatag tgaaaacggg ggcgaagaag ttgtccatat tggccacgtt taaatcaaaa    900
ctggtgaaac tcacccaggg attggcgctg acgaaaaaca tattctcaat aaacccttta    960
gggaaatagg ccaggttttc accgtaacac gccacatctt gcgaatatat gtgtagaaac   1020
tgccggaaat cgtcgtggta ttcactccag agcgatgaaa acgtttcagt ttgctcatgg   1080
aaaacggtgt aacaagggtg aacactatcc catatcacca gctcaccgtc tttcattgcc   1140
atacggaact ccggatgagc attcatcagg cgggcaagaa tgtgaataaa ggccggataa   1200
aacttgtgct tattttctt tacggtcttt aaaaaggccg taatatccag ctgaacggtc   1260
tggttatagg tacattgagc aactgactga aatgcctcaa aatgttcttt acgatgccat   1320
tgggatatat caacggtggt atatccagtg atttttttct ccatttttt ttcctccttt   1380 agaaaaactc atcgagcatc aaatgaaact gcaatttatt catatcagga ttatcaatac   1440 catattttg aaaaagccgt ttctgtaatg aaggagaaaa ctcaccgagg cagttccata   1500
ggatggcaag atcctggtat cggtctgcga ttccgactcg tccaacatca atacaaccta   1560
ttaatttccc ctcgtcaaaa ataaggttat caagtgagaa atcaccatga gtgacgactg   1620
aatccggtga gaatggcaaa agtttatgca tttctttcca gacttgttca acaggccagc   1680
cattacgctc gtcatcaaaa tcactcgcat caaccaaacc gttattcatt cgtgattgcg   1740
cctgagcgag gcgaaatacg cgatcgctgt taaaaggaca attacaaaca ggaatcgagt   1800
gcaaccggcg caggaacact gccagcgcat caacaatatt ttcacctgaa tcaggatatt   1860
cttctaatac ctggaacgct gttttttccgg ggatcgcagt ggtgagtaac catgcatcat   1920
caggagtacg gataaaatgc ttgatggtcg gaagtggcat aaattccgtc agccagttta   1980
gtctgaccat ctcatctgta acatcattgg caacgctacc tttgccatgt ttcagaaaca   2040
actctggcgc atcgggcttc ccatacaagc gatagattgt cgcacctgat tgcccgacat   2100
tatcgcgagc ccatttatac ccatataaat cagcatccat gttggaattt aatcgcggcc   2160
tcgacgtttc ccgttgaata tggctcattt ttttttcctc ctttaccaat gcttaatcag   2220
tgaggcacct atctcagcga tctgtctatt tcgttcatcc atagttgcct gactccccgt   2280
cgtgtagata actacgatac gggagggctt accatctggc cccagcgctg cgatgatacc   2340
gcgagaacca cgctcaccgg ctccggattt atcagcaata aaccagccag ccggaagggc   2400
cgagcgcaga agtggtcctg caactttatc cgcctccatc cagtctatta attgttgccg   2460
ggaagctaga gtaagtagtt cgccagttaa tagtttcgcg aacgttgttg ccatcgctac   2520
aggcatcgtg gtgtcacgct cgtcgtttgg tatggcttca ttcagctccg gttcccaacg   2580
```

```
atcaaggcga gttacatgat cccccatgtt gtgcaaaaaa gcggttagct ccttcggtcc      2640
tccgatcgtt gtcagaagta agttggccgc agtgttatca ctcatggtta tggcagcact      2700
gcataattct cttactgtca tgccatccgt aagatgcttt tctgtgactg gtgagtactc      2760
aaccaagtca ttctgagaat agtgtatgcg gcgaccgagt tgctcttgcc cggcgtcaat      2820
acgggataat accgcgccac atagcagaac tttaaaagtg ctcatcattg gaaaacgttc      2880
ttcggggcga aaactctcaa ggatcttacc gctgttgaga tccagttcga tgtaacccac      2940
tcgtgcaccc aactgatctt cagcatcttt tactttcacc agcgtttctg ggtgagcaaa      3000
aacaggaagg caaaatgccg caaaaaaggg aataagggcg acacggaaat gttgaatact      3060
catattcttc ctttttcaat attattgaag catttatcag ggttattgtc tcatgagcgg      3120
atacatattt gaatgtattt agaaaaataa acaataggg gtcagtgtta caaccaatta       3180
accaattctg aacattatcg cgagcccatt tatacctgaa tatggctcat aacacccctt      3240
gtttgcctgg cggcagtagc gcggtggtcc cacctgaccc catgccgaac tcagaagtga      3300
aacgccgtag cgccgatggt agtgtgggga ctccccatgc gagagtaggg aactgccagg      3360
catcaaataa aacgaaaggc tcagtcgaaa gactgggcct ttcgcccggg ctaattgagg      3420
ggtgtcgccc ttttgacgga tatcaagctt ctattaaccg aacgcttcgt ccaagatttc      3480
ttgctgctcc acggcatgaa ccttcgagga accgctgctc ggcgcagaca tcgcgcgacg      3540
ggagatacgc ttgatgcccg ccaacttgtc cggcagcaac tccggcaact ccaaaccgaa      3600
acgcggccag cgcccctggt tcgctggttc ctcctggacc caaaagaact ctttgacatt      3660
ttcgtaacga tccagggttt cacgcagacg acgacgcggc aacggcgcca gttgctccag      3720
acgcacaatt gccagatcat tacggttgtc tttcgccttg cgtgccgcca attcataata      3780
caacttaccg gaggtcaaca gaatacggct aactttattg cggtcgccga taccatcctc      3840
gtaggtcggt tcctccagga cgctacggaa tttaatctcg gtaaatcct taatctccga      3900
aaccgccgcc ttgtggcgca gcatggattt cggggtaaac acgatcaacg gacgttggat      3960
gccgtccaac gcgtggcggc gcagcaagtg aaagtaattg gacggggtgc tcggcatcgc      4020
gatcgtcatg ctaccctcag cccacagctg caaaaagcgc tcaatgcgcg ccgacgtgtg      4080
gtccgggccc tgaccctcgt ggccgtgtgg cagcaacaga acaacgttgg acagctgacc      4140
ccatttcgct tcgcccgagc tgatgaactc gtcaatgatc gactgggcac cattaacaaa      4200
gtcgccgaat tgcgcctccc acagcacaac cgcgtctgga ttgccaacgg tataaccgta      4260
ctcaaaaccc acagccgcgt attccgacaa cggcgaatca taaaccagga acttaccacc      4320
ggtcgggctg ccgtcgctgt tagtcgccag cagctgcagc ggggtgaact cctcgccggt      4380
gtgacgtcg atcagcacag aatgacgctg gctaaaggtg ccacgacgag agtcttgacc       4440
gctcagacgg accagcttgc cctcagcaac caggctgccc agcgccagca actcaccaaa      4500
cgcccagtca atcttacccct catacgccat ctcacgacgc ttttccagca ccggctgaac      4560
gcgcgggtgt gccgtgaaac cgttaggcag cgccaggaag gcatcaccga tacgtgccag      4620
cagggatttg tcaacagcgg tcgccaggcc cgctgggatc atttggtccg actcgacgct      4680
ctccgacggt tggacgccgt gcttctccag ttcgcgcact tcgttgaaca cacgctccag      4740
ttggccctgg taatcgcgca gcgcatcctc cgcctctttc atgctgatgt cgccacgacc      4800
gatcagagcc tcggtgtagg atttacgggc gccacgcttg gtgtccacga cgtcatagac      4860
atacggattg tcatagatg gatcgtcacc ctcattatga ccacgacgac gatagcacag       4920
catgtcaata acaacgtcct ttttaaagcg ttggcggaag tcaactgcca aacgcgcaac      4980
```

```
ccagacacac gcttctggat cgtcgccgtt cacgtggaag attggcgcac cgatcatctt    5040
cgccacatcc gtgcagtact cgctcgaacg agagtattcc ggagcggtgg tgaagccgat    5100
ttggttgttc acaatgatgt gaatcgtacc acccacacga tagccaggca gatttgccag    5160
attcagcgtc tccgcaacaa cgccttgacc cgcgaaggcc gcatcaccgt gcagcatcaa    5220
cggaacgacg gagaatgcac gttggccgtc ggagtcaatg gaaccgtggt ccagcaggtc    5280
ttgcttcgca cgcaccaaac cttccagcac tggatcgacc gcttccaaat gggacggatt    5340
tgccgtcagg gaaacctgaa tatcgttatc gccaaacatt gcagataca gacccgtcgc     5400
acccaggtgg tacttgacat cgccggaacc gtgagcctgg acgggttca gattgccttc     5460
aaactccgta agatttgcg aatacggttt gcccacgatg ttcgccagga cattcaagcg     5520
accacggtgc ggcatgccaa tgaccacttc atccaaacca tgctcggcac attggtcaat    5580
cgccgcgtcc atcattggaa taacagattc cgcaccctcc aggctaaaac gcttttggcc    5640
cacatacttg gtttgcagga aggtttcaaa cgcctccgct gcgttcagtt tcgacaagat    5700
gtacttttgt tgagcaacgg tcggtttgac gtgcttcgtc tcgacacgct gctccagcca    5760
ctccttttgt tccgggtcca gaatgtgcgc gtactcaaca ccgatgtgac ggcagtacgc    5820
gtcgcgcagc aaacccagca cgtcacgcag ctttttgtat tgagcacccg cgaaaccgtc    5880
aaccttaaag acgcggtcca ggtcccacag agtcaggcca tgcgtcaaca cctccaaatc    5940
cggatgcgaa cgaaagcgcg ccttatccaa gcgcaacggg tcggtgtccg ccatcagatg    6000
gccgcggttg cgataggccg cgatcaggtt catcacacgt gcgttcttgt caacgatcga    6060
gtccggatta tcggtgctcc aacgcactgg caggtacggg atgctcagct cgcggaagac    6120
ctcatcccag aagccatcag acaacagcag ttcatgaatg gtacgcagga agtcaccgct    6180
ttccgcacct tgaatgatac ggtggtcgta ggtagaagtc agggtaatca gtttgccaat    6240
acccagctca gcgatgcgtt cctcggacgc gccttggaac tccgccggat attccatcgc    6300
accgacaccg atgatagcac cttgacctgg catcaggcgt ggcacagagt gcaccgtgcc    6360
aatcgtgccc ggattcgtca gcgaaatcgt aacgccagcg aagtcctcgg tggtcagttt    6420
accatcacga gcacgacgga cgatgtcctc gtacgcggta acgaactgcg cgaagcgcat    6480
cgtctcgcaa cgtttgatac cggccaccac cagagagcgc ttgccatctt taccttgcag    6540
gtcaatagcc agacccagat tggtgtgcgc aggagtaacc gccgtcggct taccgtccac    6600
ctccgtgtag tggcgattca tattcgggaa cttcttaacc gcctgaacca gagcataacc    6660
cagcaaatgg gtaaagctga ttttaccacc acgcgtgcgt ttcaactgat tattgatcac    6720
gatacgatta tcgatcaaca atttcgctgg cacagcacgc accgaggtcg ccgtaggcac    6780
ttccagcgac gcgctcatgt tcttcacgac agcagccgcc gcaccacgca ggacagcaac    6840
ttcatcgcct tcggctggcg gaggcaccgc ggtcttggcg ccagagccg ccacgacacc     6900
gttgcccgct gcgccgtgt cggcggttt cggcggcgct gcggagccg ccgctgccgc       6960
acgctcagcg accaaagggc tggtcacacg agtcggctca gcagccggtt gggaagtcgg    7020
ctccgggcta tagtccacca gaaactcatg ccagcttggg tcaacggaag acggatcatc    7080
acgaaattta cgatacatac caacacgaga cgggtcctga gtcaccatgg atatatctcc    7140
ttcttaaaga attcgatatc tcagcgacaa gggcgcacac aaatttattc taaatgcata    7200
ataaatactg ataacatctt atagtttgta ttatattttg tattatcgtt gacatgtata    7260
attttgatat caaaaactga ttttcccttt attattttcg agatttattt tcttaattct    7320
ctttaacaaa ctagaaatat tgtatataca aaaaatcata aataatagat gaatagttta    7380
```

-continued

```
attataggtg ttcatcaatc gaaaaagcaa cgtatcttat ttaaagtgcg ttgctttttt    7440
ctcatttata aggttaaata attctcatat atcaagcaaa gtgacaggcg cccttaaata    7500
ttctgacaaa tgctctttcc ctaaactccc cccataaaaa aacccgccga agcgggtttt    7560
tacgttattt gcggattaac gattactcgt tatcagaacc gcccaggggg cccgagctta    7620
agactggccg tcgttttaca acacagaaag agtttgtaga aacgcaaaaa ggccatccgt    7680
caggggcctt ctgcttagtt tgatgcctgg cagttcccta ctctcgcctt ccgcttcctc    7740
gctcactgac tcgctgcgct cggtcgttcg gctgcggcga gcggtatcag ctcactcaaa    7800
ggcggtaata cggttatcca cagaatcagg ggataacgca ggaaagaaca tgtgagcaaa    7860
aggccagcaa aaggccagga accgtaaaaa ggccgcgttg ctggcgtttt tccataggct    7920
ccgcccccct gacgagcatc acaaaaatcg acgctcaagt cagaggtggc gaaacccgac    7980
aggactataa agataccagg cgtttccccc tggaagctcc ctcgtgcgct ctcctgttcc    8040
gaccctgccg cttaccggat acctgtccgc ctttctccct tcgggaagcg tggcgctttc    8100
tcatagctca cgctgtaggt atctcagttc ggtgtaggtc gttcgctcca agctgggctg    8160
tgtgcacgaa ccccccgttc agcccgaccg ctgcgcctta tccggtaact atcgtcttga    8220
gtccaacccg gtaagacacg acttatcgcc actggcagca gccactggta acaggattag    8280
cagagcgagg tatgtaggcg gtgctacaga gttcttgaag tggtgggcta actacggcta    8340
cactagaaga acagtatttg gtatctgcgc tctgctgaag ccagttacct tcggaaaaag    8400
agttggtagc tcttgatccg gcaaacaaac caccgctggt agcggtggtt ttttgtttg    8460 caagcagcag attacgcgca gaaaaaaagg atctcaagaa gatcctttga tcttttctac    8520
ggggtctgac gctcagtgga acgacgcgcg cgtaactcac gttaagggat tttggtcatg    8580
agcttgcgcc gtcccgtcaa gtcagcgtaa tgctctgctt a                       8621
```

<210> SEQ ID NO 4
<211> LENGTH: 39
<212> TYPE: DNA
<213> ORGANISM: Artificial Sequence
<220> FEATURE:
<223> OTHER INFORMATION: Forward primer for PCR amplification of codon
    optimized kgd nucleic acid sequence

<400> SEQUENCE: 4

```
tttttttgta taccatggat cgtaaatttc gtgatgatc                            39
```

<210> SEQ ID NO 5
<211> LENGTH: 42
<212> TYPE: DNA
<213> ORGANISM: Artificial Sequence
<220> FEATURE:
<223> OTHER INFORMATION: Reverse primer for PCR amplification of codon
    optimized kgd nucleic acid sequence

<400> SEQUENCE: 5

```
cccggtgaga tctagatccg aacgcttcgt ccaagatttc tt                        42
```

<210> SEQ ID NO 6
<211> LENGTH: 47
<212> TYPE: DNA
<213> ORGANISM: Artificial Sequence
<220> FEATURE:
<223> OTHER INFORMATION: Forward primer for PCR amplification of pKK223-
    3 template

<400> SEQUENCE: 6

```
cggatctaga tctcaccatc accaccatta gtcgacctgc agccaag                   47
```

<210> SEQ ID NO 7
<211> LENGTH: 44
<212> TYPE: DNA
<213> ORGANISM: Artificial Sequence
<220> FEATURE:
<223> OTHER INFORMATION: Reverse primer for PCR amplification of pKK223-
      3 template

<400> SEQUENCE: 7
tgagatctag atccgttatg tcccatggtt ctgtttcctg tgtg                44

<210> SEQ ID NO 8
<211> LENGTH: 4614
<212> TYPE: DNA
<213> ORGANISM: Artificial Sequence
<220> FEATURE:
<223> OTHER INFORMATION: pKK223-ct-his vector

<400> SEQUENCE: 8
ttgacaatta atcatcggct cgtataatgt gtggaattgt gagcggataa caatttcaca    60
caggaaacag aacctatggga cataacggat ctagatctca ccatcaccac cattagtcga   120
cctgcagcca agcttggctg ttttggcgga tgagagaaga ttttcagcct gatacagatt   180
aaatcagaac gcagaagcgg tctgataaaa cagaatttgc ctggcggcag tagcgcggtg   240
gtcccacctg accccatgcc gaactcagaa gtgaaacgcc gtagcgccga tggtagtgtg   300
gggtctcccc atgcgagagt agggaactgc caggcatcaa ataaaacgaa aggctcagtc   360
gaaagactgg gcctttcgtt ttatctgttg tttgtcggtg aacgctctcc tgagtaggac   420
aaatccgccg ggagcggatt tgaacgttgc gaagcaacgg cccggagggt ggcgggcagg   480
acgcccgcca taaactgcca ggcatcaaat taagcagaag gccatcctga cggatggcct   540
ttttgcgttt ctacaaactc ttttgtttat ttttctaaat acattcaaat atgtatccgc   600
tcatgagaca ataaccctga taaatgcttc aataatattg aaaaaggaag agtatgagta   660
ttcaacattt ccgtgtcgcc cttattccct tttttgcggc attttgcctt cctgtttttg   720
ctcacccaga aacgctggtg aaagtaaaag atgctgaaga tcagttgggt gcacgagtgg   780
gttacatcga actggatctc aacagcggta agatccttga gttttcgc cccgaagaac    840 gttttccaat gatgagcact tttaaagttc tgctatgtgg cgcggtatta tcccgtgttg   900
acgccgggca agagcaactc ggtcgccgca tacactattc tcagaatgac ttggttgagt   960
actcaccagt cacagaaaag catcttacgg atggcatgac agtaagagaa ttatgcagtg  1020
ctgccataac catgagtgat aacactgcgg ccaacttact tctgacaacg atcggaggac  1080
cgaaggagct aaccgctttt tgcacaacat ggggatca tgtaactcgc cttgatcgtt   1140
gggaaccgga gctgaatgaa gccataccaa acgacgagcg tgacaccacg atgctgtagc  1200
aatggcaaca acgttgcgca aactattaac tggcgaacta cttactctag cttcccggca  1260
acaattaata gactggatgg aggcggataa agttgcagga ccacttctgc gctcggccct  1320
tccggctggc tggtttattg ctgataaatc tggagccggt gagcgtgggt ctcgcggtat  1380
cattgcagca ctggggccag atggtaagcc ctcccgtatc gtagttatct acacgacggg  1440
gagtcaggca actatggatg aacgaaatag acagatcgct gagataggtg cctcactgat  1500
taagcattgg taactgtcag accaagttta ctcatatata ctttagattg atttaaaact  1560
tcatttttaa tttaaaagga tctaggtgaa gatcctttt gataatctca tgaccaaaat  1620
cccttaacgt gagttttcgt tccactgagc gtcagacccc gtagaaaaga tcaaaggatc  1680

```
ttcttgagat cctttttttc tgcgcgtaat ctgctgcttg caaacaaaaa aaccaccgct    1740
accagcggtg gtttgtttgc cggatcaaga gctaccaact cttttttccga aggtaactgg   1800
cttcagcaga gcgcagatac caaatactgt ccttctagtg tagccgtagt taggccacca   1860
cttcaagaac tctgtagcac cgcctacata cctcgctctg ctaatcctgt taccagtggc   1920
tgctgccagt ggcgataagt cgtgtcttac cgggttggac tcaagacgat agttaccgga   1980
taaggcgcag cggtcgggct gaacggggg ttcgtgcaca cagcccagct tggagcgaac    2040
gacctacacc gaactgagat acctacagcg tgagcattga gaaagcgcca cgcttcccga   2100
agggagaaag gcggacaggt atccggtaag cggcagggtc ggaacaggag agcgcacgag   2160
ggagcttcca gggggaaacg cctggtatct ttatagtcct gtcgggtttc gccacctctg   2220
acttgagcgt cgattttgt gatgctcgtc agggggcgg agcctatgga aaaacgccag    2280
caacgcggcc tttttacggt tcctggcctt ttgctggcct tttgctcaca tgttctttcc   2340
tgcgttatcc cctgattctg tggataaccg tattaccgcc tttgagtgag ctgataccgc   2400
tcgccgcagc cgaacgaccg agcgcagcga gtcagtgagc gaggaagcgg aagagcgcct   2460
gatgcggtat tttctcctta cgcatctgtg cggtatttca caccgcatat ggtgcactct   2520
cagtacaatc tgctctgatg ccgcatagtt aagccagtat acactccgct atcgctacgt   2580
gactgggtca tggctgcgcc ccgacacccg ccaacacccg ctgacgcgcc ctgacgggct   2640
tgtctgctcc cggcatccgc ttacagacaa gctgtgaccg tctccgggag ctgcatgtgt   2700
cagaggtttt caccgtcatc accgaaacgc gcgaggcagc tgcggtaaag ctcatcagcg   2760
tggtcgtgaa gcgattcaca gatgtctgcc tgttcatccg cgtccagctc gttgagtttc   2820
tccagaagcg ttaatgtctg gcttctgata aagcgggcca tgttaagggc ggttttttcc   2880
tgtttggtca ctgatgcctc cgtgtaaggg ggatttctgt tcatggggt aatgataccg    2940
atgaaacgag agaggatgct cacgatacgg gttactgatg atgaacatgc ccggttactg   3000
gaacgttgtg agggtaaaca actggcgta tggatgcggc gggaccagag aaaaatcact    3060
cagggtcaat gccagcgctt cgttaataca gatgtaggtg ttccacaggg tagccagcag   3120
catcctgcga tgcagatccg gaacataatg gtgcagggcg ctgacttccg cgtttccaga   3180
ctttacgaaa cacggaaacc gaagaccatt catgttgttg ctcaggtcgc agacgttttg   3240
cagcagcagt cgcttcacgt tcgctcgcgt atcggtgatt cattctgcta accagtaagg   3300
caaccccgcc agcctagccg ggtcctcaac gacaggagca cgatcatgcg cacccgtggc   3360
caggacccaa cgctgcccga gatgcgccgc gtgcggctgc tggagatggc ggacgcgatg   3420
gatatgttct gccaagggtt ggtttgcgca ttcacagttc tccgcaagaa ttgattggct   3480
ccaattcttg gagtggtgaa tccgttagcg aggtgccgcc ggcttccatt caggtcgagg   3540
tggcccggct ccatgcaccg cgacgcaacg cggggaggca gacaaggtat agggcggcgc   3600
ctacaatcca tgccaacccg ttccatgtgc tcgccgaggc ggcataaatc gccgtgacga   3660
tcagcggtcc agtgatcgaa gttaggctgg taagagccgc gagcgatcct tgaagctgtc   3720
cctgatggtc gtcatctacc tgcctggaca gcatggcctg caacgcgggc atcccgatgc   3780
cgccggaagc gagaagaatc ataatgggga aggccatcca gcctcgcgtc gcgaacgcca   3840
gcaagacgta gcccagcgcg tcggccgcca tgccggcgat aatggcctgc ttctcgccga   3900
aacgtttggt ggcgggacca gtgacgaagg cttgagcgag ggcgtgcaag attccgaata   3960
ccgcaagcga caggccgatc atcgtcgcgc tccagcgaaa gcggtcctcg ccgaaaatga   4020
cccagagcgc tgccggcacc tgtcctacga gttgcatgat aaagaagaca gtcataagtg   4080
```

```
cggcgacgat agtcatgccc cgcgcccacc ggaaggagct gactgggttg aaggctctca    4140
agggcatcgg tcgacgctct cccttatgcg actcctgcat taggaagcag cccagtagta    4200
ggttgaggcc gttgagcacc gccgccgcaa ggaatggtgc atgcaaggag atggcgccca    4260
acagtccccc ggccacgggg cctgccacca tacccacgcc gaaacaagcg ctcatgagcc    4320
cgaagtggcg agcccgatct tccccatcgg tgatgtcggc gatataggcg ccagcaaccg    4380
cacctgtggc gccggtgatg ccggccacga tgcgtccggc gtagaggatc cgggcttatc    4440
gactgcacgg tgcaccaatg cttctggcgt caggcagcca tcggaagctg tggtatggct    4500
gtgcaggtcg taaatcactg cataattcgt gtcgctcaag cgcactcccc gttctggata    4560 atgtttttg cgccgacatc ataacggttc tggcaaatat tctgaaatga gctg            4614
```

<210> SEQ ID NO 9
<211> LENGTH: 8
<212> TYPE: PRT
<213> ORGANISM: Artificial Sequence
<220> FEATURE:
<223> OTHER INFORMATION: Histidine tag polypeptide sequence

<400> SEQUENCE: 9

Ser Arg Ser His His His His His
1               5

<210> SEQ ID NO 10
<211> LENGTH: 8241
<212> TYPE: DNA
<213> ORGANISM: Artificial Sequence
<220> FEATURE:
<223> OTHER INFORMATION: pKK223-kgd plasmid with codon optimized kgd
      gene nucleic acid sequence

<400> SEQUENCE: 10

```
ttgacaatta atcatcggct cgtataatgt gtggaattgt gagcggataa caatttcaca      60
caggaaacag aaccatggat cgtaaatttc gtgatgatcc gtcttccgtt gacccaagct     120
ggcatgagtt tctggtggac tatagcccgg agccgacttc ccaaccggct gctgagccga     180
ctcgtgtgac cagcccttg gtcgctgagc gtgcggcagc ggcggctccg caagcgccgc     240
cgaaaccggc cgacacggcc gcagcgggca acggtgtcgt ggcggctctg ccgccaaga     300 ccgcggtgcc tccgccagcc gaaggcgatg aagttgctgt cctgcgtggt gcggcggctg     360
ctgtcgtgaa gaacatgagc gcgtcgctgg aagtgcctac ggcgacctcg gtgcgtgctg     420
tgccagcgaa attgttgatc gataatcgta tcgtgatcaa taatcagttg aaacgcacgc     480
gtggtggtaa aatcagcttt acccatttgc tgggttatgc tctggttcag gcggttaaga     540
agttcccgaa tatgaatcgc cactacacg aggtggacgg taagccgacg gcggttactc     600
ctgcgcacac caatctgggt ctggctattg acctgcaagg taaagatggc aagcgctctc     660
tggtggtggc cggtatcaaa cgttgcgaga cgatgcgctt cgcgcagttc gttaccgcgt     720
acgaggacat cgtccgtcgt gctcgtgatg gtaaactgac caccgaggac ttcgctggcg     780
ttacgatttc gctgacgaat ccgggcacga ttggcacggt gcactctgtg ccacgcctga     840
tgccaggtca aggtgctatc atcggtgtcg gtgcgatgga atatccggcg gagttccaag     900
gcgcgtccga ggaacgcatc gctgagctgg gtattggcaa actgattacc ctgacttcta     960
cctacgacca ccgtatcatt caaggtgcgg aaagcggtga cttcctgcgt accattcatg    1020
aactgctgtt gtctgatggc ttctgggatg aggtcttccg cgagctgagc atcccgtacc    1080
tgccagtgcg ttggagcacc gataatccgg actcgatcgt tgacaagaac gcacgtgtga    1140
```

```
tgaacctgat cgcggcctat cgcaaccgcg gccatctgat ggcggacacc gacccgttgc    1200
gcttggataa ggcgcgcttt cgttcgcatc cggatttgga ggtgttgacg catggcctga    1260
ctctgtggga cctggaccgc gtctttaagg ttgacggttt cgcgggtgct caatacaaaa    1320
agctgcgtga cgtgctgggt ttgctgcgcg acgcgtactg ccgtcacatc ggtgttgagt    1380
acgcgcacat tctggacccg gaacaaaagg agtggctgga gcagcgtgtc gagacgaagc    1440
acgtcaaacc gaccgttgct caacaaaagt acatcttgtc gaaactgaac gcagcggagg    1500
cgtttgaaac cttcctgcaa accaagtatg tgggccaaaa gcgttttagc ctggagggtg    1560
cggaatctgt tattccaatg atggacgcgc gattgacca atgtgccgag catggtttgg     1620
atgaagtggt cattggcatg ccgcaccgtg gtcgcttgaa tgtcctggcg aacatcgtgg    1680
gcaaaccgta ttcgcaaatc tttacggagt ttgaaggcaa tctgaacccg tcccaggctc    1740
acggttccgg cgatgtcaag taccacctgg gtgcgacggg tctgtatctg caaatgtttg    1800
gcgataacga tattcaggtt tccctgacgg caaatccgtc ccatttggaa gcggtcgatc    1860
cagtgctgga aggtttggtg cgtgcgaagc aagacctgct ggaccacggt tccattgact    1920
ccgacggcca acgtgcattc tccgtcgttc cgttgatgct gcacggtgat gcggccttcg    1980
cgggtcaagg cgttgttgcg gagacgctga atctggcaaa tctgcctggc tatcgtgtgg    2040
gtggtacgat tcacatcatt gtgaacaacc aaatcggctt caccaccgct ccggaatact    2100
ctcgttcgag cgagtactgc acggatgtgg cgaagatgat cggtgcgcca atcttccacg    2160
tgaacggcga cgatccagaa gcgtgtgtct gggttgcgcg tttggcagtt gacttccgcc    2220
aacgctttaa aaaggacgtt gttattgaca tgctgtgcta tcgtcgtcgt ggtcataatg    2280
agggtgacga tccatctatg accaatccgt atgtctatga cgtcgtggac accaagcgtg    2340
gcgcccgtaa atcctacacc gaggctctga tcggtcgtgg cgacatcagc atgaaagagg    2400
cggaggatgc gctgcgcgat taccagggcc aactggagcg tgtgttcaac gaagtgcgcg    2460
aactggagaa gcacggcgtc caaccgtcgg agagcgtcga gtcggaccaa atgatcccag    2520
cgggcctggc gaccgctgtt gacaaatccc tgctggcacg tatcggtgat gccttcctgg    2580
cgctgcctaa cggtttcacg gcacacccgc gcgttcagcc ggtgctggaa aagcgtcgtg    2640
agatggcgta tgagggtaag attgactggg cgtttggtga gttgctggcg ctgggcagcc    2700
tggttgctga gggcaagctg gtccgtctga gcggtcaaga ctctcgtcgt ggcacccttta   2760 gccagcgtca ttctgtgctg atcgaccgtc acaccggcga ggagttcacc ccgctgcagc    2820
tgctggcgac taacagcgac ggcagcccga ccggtgtaa gttcctggtt tatgattcgc     2880
cgttgtcgga atacgcggct gtgggttttg agtacggtta taccgttggc aatccagacg    2940
cggttgtgct gtgggaggcg caattcggcg actttgttaa tggtgcccag tcgatcattg    3000
acgagttcat cagctcgggc gaagcgaaat ggggtcagct gtccaacgtt gttctgttgc    3060
tgccacacgg ccacgagggt cagggcccgg accacgtcgg cgcgcatt gagcgctttt      3120 tgcagctgtg ggctgagggt agcatgacga tcgcgatgcc gagcacccccg tccaattact   3180 ttcacttgct gcgccgccac gcgttggacg gcatccaacg tccgttgatc gtgtttaccc    3240
cgaaatccat gctgcgccac aaggcggcgg tttcggagat taaggatttt accgagatta    3300
aattccgtag cgtcctggag gaaccgacct acgaggatgg tatcggcgac cgcaataaag    3360
ttagccgtat tctgtgacc tccggtaagt tgtattatga attggcggca cgcaaggcga    3420
aagacaaccg taatgatctg gcaattgtgc gtctggagca actggcgccg ttgccgcgtc    3480
gtcgtctgcg tgaaaccctg gatcgttacg aaaatgtcaa agagttctt tgggtccagg     3540
```

```
aggaaccagc gaaccagggc gcctggccgc gtttcggttt ggagttgccg gagttgctgc    3600
cggacaagtt ggcgggcatc aagcgtatct cccgtcgcgc gatgtctgcg ccgagcagcg    3660
gttcctcgaa ggttcatgcc gtggagcagc aagaaatctt ggacgaagcg ttcggatcta    3720
gatctcacca tcaccaccat tagtcgacct gcagccaagc ttggctgttt tggcggatga    3780
gagaagattt tcagcctgat acagattaaa tcagaacgca gaagcggtct gataaaacag    3840
aatttgcctg gcggcagtag cgcggtggtc ccacctgacc ccatgccgaa ctcagaagtg    3900
aaacgccgta gcgccgatgg tagtgtgggg tctccccatg cgagagtagg gaactgccag    3960
gcatcaaata aaacgaaagg ctcagtcgaa agactgggcc tttcgtttta tctgttgttt    4020
gtcggtgaac gctctcctga gtaggacaaa tccgccggga gcggatttga acgttgcgaa    4080
gcaacggccc ggagggtggc gggcaggacg cccgccataa actgccaggc atcaaattaa    4140
gcagaaggcc atcctgacgg atggcctttt tgcgtttcta caaactcttt tgtttatttt    4200
tctaaataca ttcaaatatg tatccgctca tgagacaata accctgataa atgcttcaat    4260
aatattgaaa aaggaagagt atgagtattc aacatttccg tgtcgccctt attccctttt    4320
ttgcggcatt ttgccttcct gttttgctc acccagaaac gctggtgaaa gtaaaagatg    4380
ctgaagatca gttgggtgca cgagtgggtt acatcgaact ggatctcaac agcggtaaga    4440
tccttgagag ttttcgcccc gaagaacgtt ttccaatgat gagcactttt aaagttctgc    4500
tatgtggcgc ggtattatcc cgtgttgacg ccgggcaaga gcaactcggt cgccgcatac    4560
actattctca gaatgacttg gttgagtact caccagtcac agaaaagcat cttacggatg    4620
gcatgacagt aagagaatta tgcagtgctg ccataaccat gagtgataac actgcggcca    4680
acttacttct gacaacgatc ggaggaccga aggagctaac cgcttttttg cacaacatgg    4740
gggatcatgt aactcgcctt gatcgttggg aaccggagct gaatgaagcc ataccaaacg    4800
acgagcgtga caccacgatg ctgtagcaat ggcaacaacg ttgcgcaaac tattaactgg    4860
cgaactactt actctagctt cccggcaaca attaatagac tggatggagg cggataaagt    4920
tgcaggacca cttctgcgct cggcccttcc ggctggctgg tttattgctg ataaatctgg    4980
agccggtgag cgtgggtctc gcggtatcat tgcagcactg gggccagatg gtaagccctc    5040
ccgtatcgta gttatctaca cgacggggag tcaggcaact atggatgaac gaaatagaca    5100
gatcgctgag ataggtgcct cactgattaa gcattggtaa ctgtcagacc aagtttactc    5160
atatatactt tagattgatt taaaacttca ttttaatttt aaaaggatct aggtgaagat    5220 ccttttgat aatctcatga ccaaaatccc ttaacgtgag ttttcgttcc actgagcgtc    5280
agaccccgta gaaaagatca aaggatcttc ttgagatcct ttttttctgc gcgtaatctg    5340
ctgcttgcaa acaaaaaaac caccgctacc agcggtggtt tgtttgccgg atcaagagct    5400
accaactctt tttccgaagg taactggctt cagcagagcg cagataccaa atactgtcct    5460
tctagtgtag ccgtagttag gccaccactt caagaactct gtagcaccgc ctacatacct    5520
cgctctgcta atcctgttac cagtggctgc tgccagtggc gataagtcgt gtcttaccgg    5580
gttggactca agacgatagt taccggataa ggcgcagcgg tcgggctgaa cggggggttc    5640
gtgcacacag cccagcttgg agcgaacgac ctacaccgaa ctgagatacc tacagcgtga    5700
gcattgagaa agcgccacgc ttcccgaagg agaaaggcg gacaggtatc cggtaagcgg    5760
cagggtcgga acaggagagc gcacgaggga gcttccaggg ggaaacgcct ggtatcttta    5820
tagtcctgtc gggtttcgcc acctctgact tgagcgtcga ttttgtgat gctcgtcagg    5880 ggggcggagc ctatggaaaa acgccagcaa cgcggccttt ttacggttcc tggccttttg    5940
```

```
ctggcctttt gctcacatgt tctttcctgc gttatcccct gattctgtgg ataaccgtat    6000
taccgccttt gagtgagctg ataccgctcg ccgcagccga acgaccgagc gcagcgagtc    6060
agtgagcgag gaagcggaag agcgcctgat gcggtatttt ctccttacgc atctgtgcgg    6120
tatttcacac cgcatatggt gcactctcag tacaatctgc tctgatgccg catagttaag    6180
ccagtataca ctccgctatc gctacgtgac tgggtcatgg ctgcgccccg acacccgcca    6240
acacccgctg acgcgccctg acgggcttgt ctgctcccgg catccgctta cagacaagct    6300
gtgaccgtct ccgggagctg catgtgtcag aggttttcac cgtcatcacc gaaacgcgcg    6360
aggcagctgc ggtaaagctc atcagcgtgg tcgtgaagcg attcacagat gtctgcctgt    6420
tcatccgcgt ccagctcgtt gagtttctcc agaagcgtta atgtctggct tctgataaag    6480
cgggccatgt taagggcggt ttttcctgt ttggtcactg atgcctccgt gtaaggggga    6540
tttctgttca tgggggtaat gataccgatg aaacgagaga ggatgctcac gatacgggtt    6600
actgatgatg aacatgcccg gttactggaa cgttgtgagg gtaaacaact ggcggtatgg    6660
atgcggcggg accagagaaa aatcactcag ggtcaatgcc agcgcttcgt taatacagat    6720
gtaggtgttc cacagggtag ccagcagcat cctgcgatgc agatccggaa cataatggtg    6780
cagggcgctg acttccgcgt ttccagactt tacgaaacac ggaaaccgaa gaccattcat    6840
gttgttgctc aggtcgcaga cgttttgcag cagcagtcgc ttcacgttcg ctcgcgtatc    6900
ggtgattcat tctgctaacc agtaaggcaa ccccgccagc ctagccgggt cctcaacgac    6960
aggagcacga tcatgcgcac ccgtggccag gacccaacgc tgcccgagat gcgccgcgtg    7020
cggctgctgg agatggcgga cgcgatggat atgttctgcc aagggttggt ttgcgcattc    7080
acagttctcc gcaagaattg attggctcca attcttggag tggtgaatcc gttagcgagg    7140
tgccgccggc ttccattcag gtcgaggtgg cccggctcca tgcaccgcga cgcaacgcgg    7200
ggaggcagac aaggtatagg gcggcgccta caatccatgc caacccgttc catgtgctcg    7260
ccgaggcggc ataaatcgcc gtgacgatca gcggtccagt gatcgaagtt aggctggtaa    7320
gagccgcgag cgatccttga agctgtccct gatggtcgtc atctacctgc ctggacagca    7380
tggcctgcaa cgcgggcatc ccgatgccgc cggaagcgag aagaatcata atggggaagg    7440
ccatccagcc tcgcgtcgcg aacgccagca agacgtagcc cagcgcgtcg gccgccatgc    7500
cggcgataat ggcctgcttc tcgccgaaac gtttggtggc gggaccagtg acgaaggctt    7560
gagcgagggc gtgcaagatt ccgaataccg caagcgacag gccgatcatc gtcgcgctcc    7620
agcgaaagcg gtcctcgccg aaaatgaccc agagcgctgc cggcacctgt cctacgagtt    7680
gcatgataaa gaagacagtc ataagtgcgg cgacgatagt catgccccgc gcccaccgga    7740
aggagctgac tgggttgaag gctctcaagg gcatcggtcg acgctctccc ttatgcgact    7800
cctgcattag gaagcagccc agtagtaggt tgaggccgtt gagcaccgcc gccgcaagga    7860
atggtgcatg caaggagatg cgcccaaca gtcccccgc cacggggcct gccaccatac    7920
ccacgccgaa acaagcgctc atgagcccga agtggcgagc ccgatcttcc ccatcggtga    7980
tgtcggcgat ataggcgcca gcaaccgcac ctgtggcgcc ggtgatgccg gccacgatgc    8040
gtccggcgta gaggatccgg gcttatcgac tgcacggtgc accaatgctt ctggcgtcag    8100
gcagccatcg gaagctgtgg tatggctgtg caggtcgtaa atcactgcat aattcgtgtc    8160
gctcaaggcg cactcccgtt ctggataatg ttttttgcgc cgacatcata acggttctgg    8220
caaatattct gaaatgagct g                                              8241
```

<210> SEQ ID NO 11

<211> LENGTH: 3716
<212> TYPE: DNA
<213> ORGANISM: Artificial Sequence
<220> FEATURE:
<223> OTHER INFORMATION: Codon-optimized mcr nucleic acid sequence

<400> SEQUENCE: 11

```
gatatcgaat tccgctagca ggagctaagg aagctaaaat gtccggtacg ggtcgtttgg       60
ctggtaaaat tgcattgatc accggtggtg ctggtaacat tggttccgag ctgacccgcc      120
gttttctggc cgagggtgcg acggttatta tcagcggccg taaccgtgcg aagctgaccg      180
cgctggccga cgcatgcaa gccgaggccg gcgtgccggc caagcgcatt gatttggagg      240
tgatggatgg ttccgaccct gtggctgtcc gtgccggtat cgaggcaatc gtcgctcgcc      300
acggtcagat tgacattctg gttaacaacg cgggctccgc cggtgcccaa cgtcgcttgg      360
cggaaattcc gctgacggag gcagaattgg gtccgggtgc ggaggagact ttgcacgctt      420
cgatcgcgaa tctgttgggc atgggttggc acctgatgcg tattgcggct ccgcacatgc      480
cagttggctc cgcagttatc aacgtttcga ctattttctc gcgcgcagag tactatggtc      540
gcattccgta cgttaccccg aaggcagcgc tgaacgcttt gtcccagctg gctgcccgcg      600
agctgggcgc tcgtggcatc cgcgttaaca ctattttccc aggtcctatt gagtccgacc      660
gcatccgtac cgtgtttcaa cgtatggatc aactgaaggg tcgcccggag ggcgacaccg      720
cccatcactt tttgaacacc atgcgcctgt gccgcgcaaa cgaccaaggc gctttggaac      780
gccgctttcc gtccgttggc gatgttgctg atgcggctgt gtttctggct ctgctgaga      840
gcgcggcact gtcgggtgag acgattgagg tcacccacgg tatggaactg ccggcgtgta      900
gcgaaacctc cttgttggcg cgtaccgatc tgcgtaccat cgacgcgagc ggtcgcacta      960
ccctgatttg cgctggcgat caaattgaag aagttatggc cctgacgggc atgctgcgta     1020
cgtgcggtag cgaagtgatt atcggcttcc gttctgcggc tgccctggcg caatttgagc     1080
aggcagtgaa tgaatctcgc cgtctggcag gtgcggattt caccccgccg atcgctttgc     1140
cgttggaccc acgtgacccg gccaccattg atgcggtttt cgattggggc gcaggcgaga     1200
atacgggtgg catccatgcg gcggtcattc tgccggcaac ctcccacgaa ccggctccgt     1260
gcgtgattga agtcgatgac gaacgcgtcc tgaatttcct ggccgatgaa attaccggca     1320
ccatcgttat tgcgagccgt ttggcgcgct attggcaatc ccaacgcctg accccgggtg     1380
cccgtgcccg cggtccgcgt gttatctttc tgagcaacgg tgccgatcaa aatggtaatg     1440
tttacggtcg tattcaatct gcggcgatcg gtcaattgat tcgcgtttgg cgtcacgagg     1500
cggagttgga ctatcaacgt gcatccgccg caggcgatca cgttctgccg ccggtttggg     1560
cgaaccagat tgtccgtttc gctaaccgct ccctggaagg tctggagttc gcgtgcgcgt     1620
ggaccgcaca gctgctgcac agccaacgtc atattaacga aattacgctg aacattccag     1680
ccaatattag cgcgaccacg ggcgcacgtt ccgccagcgt cggctgggcc gagtccttga     1740
ttggtctgca cctgggcaag gtggctctga ttaccggtgg ttcggcgggc atcggtggtc     1800
aaatcggtcg tctgctggcc ttgtctgcg cgcgtgtgat gctggccgct cgcgatcgcc     1860
ataaattgga acagatgcaa gccatgattc aaagcgaatt ggcggaggtt ggttataccg     1920
atgtggagga ccgtgtgcac atcgctccgg gttgcgatgt gagcagcgag gcgcagctgg     1980
cagatctggt ggaacgtacg ctgtccgcat tcggtaccgt ggattatttg attaataacg     2040
ccggtattgc gggcgtggag gagatggtga tcgacatgcc ggtggaaggc tggcgtcaca     2100
ccctgtttgc caacctgatt tcgaattatt cgctgatgcg caagttggcg ccgctgatga     2160
```

| | |
|---|---|
| agaagcaagg tagcggttac atcctgaacg tttcttccta ttttggcggt gagaaggacg | 2220 |
| cggcgattcc ttatccgaac cgcgccgact acgccgtctc caaggctggc caacgcgcga | 2280 |
| tggcggaagt gttcgctcgt ttcctgggtc cagagattca gatcaatgct attgccccag | 2340 |
| gtccggttga aggcgaccgc ctgcgtggta ccggtgagcg tccggccctg tttgctcgtc | 2400 |
| gcgcccgtct gatcttggag aataaacgcc tgaacgaatt gcacgcggct ttgattgctg | 2460 |
| cggcccgcac cgatgagcgc tcgatgcacg agttggttga attgttgctg ccgaacgacg | 2520 |
| tggccgcgtt ggagcagaac ccagcggccc ctaccgcgct gcgtgagctg cacgccgct | 2580 |
| tccgtagcga aggtgatccg gcggcaagct cctcgtccgc cttgctgaat cgctccatcg | 2640 |
| ctgccaagct gttggctcgc ttgcataacg gtggctatgt gctgccggcg gatatttttg | 2700 |
| caaatctgcc taatccgccg gacccgttct tacccgtgc gcaaattgac cgcgaagctc | 2760 |
| gcaaggtgcg tgatggtatt atgggtatgc tgtatctgca gcgtatgcca accgagtttg | 2820 |
| acgtcgctat ggcaaccgtg tactatctgg ccgatcgtaa cgtgagcggc gaaactttcc | 2880 |
| atccgtctgg tggtttgcgc tacgagcgta ccccgaccgg tggcgagctg ttcggcctgc | 2940 |
| catcgccgga acgtctggcg gagctggttg gtagcacggt gtacctgatc ggtgaacacc | 3000 |
| tgaccgagca cctgaacctg ctggctcgtg cctatttgga gcgctacggt gcccgtcaag | 3060 |
| tggtgatgat tgttgagacg gaaaccggtg cggaaaccat gcgtcgtctg ttgcatgatc | 3120 |
| acgtcgaggc aggtcgcctg atgactattg tggcaggtga tcagattgag gcagcgattg | 3180 |
| accaagcgat cacgcgctat ggccgtccgg gtccggtggt gtgcactcca ttccgtccac | 3240 |
| tgccaaccgt tccgctggtc ggtcgtaaag actccgattg gagcaccgtt ttgagcgagg | 3300 |
| cggaatttgc ggaactgtgt gagcatcagc tgacccacca tttccgtgtt gctcgtaaga | 3360 |
| tcgccttgtc ggatggcgcg tcgctggcgt tggttacccc ggaaacgact gcgactagca | 3420 |
| ccacggagca atttgctctg gcgaacttca tcaagaccac cctgcacgcg ttcaccgcga | 3480 |
| ccatcggtgt tgagtcggag cgcaccgcgc aacgtattct gattaaccag gttgatctga | 3540 |
| cgcgccgcgc ccgtgcggaa gagccgcgtg acccgcacga gcgtcagcag gaattggaac | 3600 |
| gcttcattga agccgttctg ctggttaccg ctccgctgcc tcctgaggca gacacgcgct | 3660 |
| acgcaggccg tattcaccgc ggtcgtgcga ttaccgtcta atagaagctt gatatc | 3716 |

<210> SEQ ID NO 12
<211> LENGTH: 45
<212> TYPE: DNA
<213> ORGANISM: Artificial Sequence
<220> FEATURE:
<223> OTHER INFORMATION: PCR primer

<400> SEQUENCE: 12
tcgtaccaac catggccggt acgggtcgtt tggctggtaa aattg                45

<210> SEQ ID NO 13
<211> LENGTH: 42
<212> TYPE: DNA
<213> ORGANISM: Artificial Sequence
<220> FEATURE:
<223> OTHER INFORMATION: PCR primer

<400> SEQUENCE: 13
cggtgtgaga tctagatccg acggtaatcg cacgaccgcg gt                42

<210> SEQ ID NO 14
<211> LENGTH: 8262
<212> TYPE: DNA

<213> ORGANISM: Artificial Sequence
<220> FEATURE:
<223> OTHER INFORMATION: pkk223 plasmid comprising codon-optimized mcr
      nucleic acid sequence

<400> SEQUENCE: 14

| | | | | | |
|---|---|---|---|---|---|
| ttgacaatta | atcatcggct | cgtataatgt | gtggaattgt | gagcggataa | caatttcaca | 60 |
| caggaaacag | aaccatggcc | ggtacgggtc | gtttggctgg | taaaattgca | ttgatcaccg | 120 |
| gtggtgctgg | taacattggt | tccgagctga | cccgccgttt | tctggccgag | ggtgcgacgg | 180 |
| ttattatcag | cggccgtaac | cgtgcgaagc | tgaccgcgct | ggccgagcgc | atgcaagccg | 240 |
| aggccggcgt | gccggccaag | cgcattgatt | tggaggtgat | ggatggttcc | gaccctgtgg | 300 |
| ctgtccgtgc | cggtatcgag | gcaatcgtcg | ctcgccacgg | tcagattgac | attctggtta | 360 |
| acaacgcggg | ctccgccggt | gcccaacgtc | gcttggcgga | aattccgctg | acggaggcag | 420 |
| aattgggtcc | gggtgcggag | gagactttgc | acgcttcgat | cgcgaatctg | ttgggcatgg | 480 |
| gttggcacct | gatgcgtatt | gcggctccgc | acatgccagt | tggctccgca | gttatcaacg | 540 |
| tttcgactat | tttctcgcgc | gcagagtact | atggtcgcat | tccgtacgtt | accccgaagg | 600 |
| cagcgctgaa | cgctttgtcc | cagctggctg | cccgcgagct | gggcgctcgt | ggcatccgcg | 660 |
| ttaacactat | tttcccaggt | cctattgagt | ccgaccgcat | ccgtaccgtg | tttcaacgta | 720 |
| tggatcaact | gaagggtcgc | ccggagggcg | acaccgccca | tcactttttg | aacaccatgc | 780 |
| gcctgtgccg | cgcaaacgac | caaggcgctt | ggaacgccg | ctttccgtcc | gttggcgatg | 840 |
| ttgctgatgc | ggctgtgttt | ctggcttctg | ctgagagcgc | ggcactgtcg | ggtgagacga | 900 |
| ttgaggtcac | ccacggtatg | gaactgccgg | cgtgtagcga | aacctccttg | ttggcgcgta | 960 |
| ccgatctgcg | taccatcgac | gcgagcggtc | gcactaccct | gatttgcgct | ggcgatcaaa | 1020 |
| ttgaagaagt | tatggccctg | acgggcatgc | tgcgtacgtg | cggtagcgaa | gtgattatcg | 1080 |
| gcttccgttc | tgcggctgcc | ctggcgcaat | ttgagcaggc | agtgaatgaa | tctcgccgtc | 1140 |
| tggcaggtgc | ggatttcacc | ccgccgatcg | ctttgccgtt | ggacccacgt | gacccggcca | 1200 |
| ccattgatgc | ggttttcgat | tggggcgcag | gcgagaatac | gggtggcatc | catgcggcgg | 1260 |
| tcattctgcc | ggcaacctcc | cacgaaccgg | ctccgtgcgt | gattgaagtc | gatgacgaac | 1320 |
| gcgtcctgaa | tttcctggcc | gatgaaatta | ccggcaccat | cgttattgcg | agccgtttgg | 1380 |
| cgcgctattg | gcaatcccaa | cgcctgaccc | cgggtgcccg | tgcccgcggt | ccgcgtgtta | 1440 |
| tctttctgag | caacggtgcc | gatcaaaatg | gtaatgttta | cggtcgtatt | caatctgcgg | 1500 |
| cgatcggtca | attgattcgc | gtttggcgtc | acgaggcgga | gttggactat | caacgtgcat | 1560 |
| ccgccgcagg | cgatcacgtt | ctgccgccgg | tttgggcgaa | ccagattgtc | cgtttcgcta | 1620 |
| accgctccct | ggaaggtctg | gagttcgcgt | gcgcgtggac | cgcacagctg | ctgcacagcc | 1680 |
| aacgtcatat | taacgaaatt | acgctgaaca | ttccagccaa | tattagcgcg | accacgggcg | 1740 |
| cacgttccgc | cagcgtcggc | tgggccgagt | ccttgattgg | tctgcacctg | gcaaggtgg | 1800 |
| ctctgattac | cggtggttcg | gcgggcatcg | gtggtcaaat | cggtcgtctg | ctggccttgt | 1860 |
| ctggcgcgcg | tgtgatgctg | gccgctcgcg | atcgccataa | attggaacag | atgcaagcca | 1920 |
| tgattcaaag | cgaattggcg | gaggttggtt | ataccgatgt | ggaggaccgt | gtgcacatcg | 1980 |
| ctccgggttg | cgatgtgagc | agcgaggcgc | agctggcaga | tctggtggaa | cgtacgctgt | 2040 |
| ccgcattcgg | taccgtggat | tatttgatta | ataaccgcgg | tattgcgggc | gtggaggaga | 2100 |
| tggtgatcga | catgccggtg | aaggctggc | gtcacaccct | gtttgccaac | ctgatttcga | 2160 |
| attattcgct | gatgcgcaag | ttggcgccgc | tgatgaagaa | gcaaggtagc | ggttacatcc | 2220 |

```
tgaacgtttc ttcctatttt ggcggtgaga aggacgcggc gattccttat ccgaaccgcg    2280
ccgactacgc cgtctccaag gctggccaac gcgcgatggc ggaagtgttc gctcgtttcc    2340
tgggtccaga gattcagatc aatgctattg ccccaggtcc ggttgaaggc gaccgcctgc    2400
gtggtaccgg tgagcgtccg ggcctgtttg ctcgtcgcgc ccgtctgatc ttggagaata    2460
aacgcctgaa cgaattgcac gcggctttga ttgctgcggc ccgcaccgat gagcgctcga    2520
tgcacgagtt ggttgaattg ttgctgccga acgacgtggc cgcgttggag cagaacccag    2580
cggcccctac cgcgctgcgt gagctggcac gccgcttccg tagcgaaggt gatccggcgg    2640
caagctcctc gtccgccttg ctgaatcgct ccatcgctgc caagctgttg gctcgcttgc    2700
ataacggtgg ctatgtgctg ccggcggata ttttttgcaaa tctgcctaat ccgccggacc    2760
cgttctttac ccgtgcgcaa attgaccgcg aagctcgcaa ggtgcgtgat ggtattatgg    2820
gtatgctgta tctgcagcgt atgccaaccg agtttgacgt cgctatggca accgtgtact    2880
atctggccga tcgtaacgtg agcggcgaaa ctttccatcc gtctggtggt ttgcgctacg    2940
agcgtacccc gaccggtggc gagctgttcg gcctgccatc gccggaacgt ctggcggagc    3000
tggttggtag cacggtgtac ctgatcggtg aacacctgac cgagcacctg aacctgctgg    3060
ctcgtgccta tttggagcgc tacggtgccc gtcaagtggt gatgattgtt gagacggaaa    3120
ccggtgcgga aaccatgcgt cgtctgttgc atgatcacgt cgaggcaggt cgcctgatga    3180
ctattgtggc aggtgatcag attgaggcag cgattgacca agcgatcacg cgctatggcc    3240
gtccgggtcc ggtggtgtgc actccattcc gtccactgcc aaccgttccg ctggtcggtc    3300
gtaaagactc cgattggagc accgttttga gcgaggcgga atttgcggaa ctgtgtgagc    3360
atcagctgac ccaccatttc cgtgttgctc gtaagatcgc cttgtcggat ggcgcgtcgc    3420
tggcgttggt tacccccggaa acgactgcga ctagcaccac ggagcaattt gctctggcga    3480
acttcatcaa gaccaccctg cacgcgttca ccgcgaccat cggtgttgag tcggagcgca    3540
ccgcgcaacg tattctgatt aaccaggttg atctgacgcg ccgcgcccgt gcggaagagc    3600
cgcgtgaccc gcacgagcgt cagcaggaat tggaacgctt cattgaagcc gttctgctgg    3660
ttaccgctcc gctgcctcct gaggcagaca cgcgctacgc aggccgtatt caccgcggtc    3720
gtgcgattac cgtcggatct agatctcacc atcaccacca ttagtcgacc tgcagccaag    3780
cttggctgtt ttggcggatg agagaagatt ttcagcctga tacagattaa atcagaacgc    3840
agaagcggtc tgataaaaca gaatttgcct ggcggcagta gcgcggtggt cccacctgac    3900
cccatgccga actcagaagt gaaacgccgt agcgccgatg gtagtgtggg gtctccccat    3960
gcgagagtag ggaactgcca ggcatcaaat aaaacgaaag gctcagtcga aagactgggc    4020
ctttcgtttt atctgttgtt tgtcggtgaa cgctctcctg agtaggacaa atccgccggg    4080
agcggatttg aacgttgcga agcaacggcc cggagggtgg cgggcaggac gcccgccata    4140
aactgccagg catcaaatta agcagaaggc catcctgacg gatggccttt ttgcgtttct    4200
acaaactctt ttgtttattt ttctaaatac attcaaatat gtatccgctc atgagacaat    4260
aaccctgata aatgcttcaa taatattgaa aaaggaagag tatgagtatt caacatttcc    4320
gtgtcgccct tattccctttt tttgcggcat tttgccttcc tgttttttgct cacccagaaa    4380 cgctggtgaa agtaaaagat gctgaagatc agttgggtgc acgagtgggt tacatcgaac    4440
tggatctcaa cagcggtaag atccttgaga gttttcgccc cgaagaacgt tttccaatga    4500
tgagcacttt taaagttctg ctatgtggcg cggtattatc ccgtgttgac gccgggcaag    4560
agcaactcgg tcgccgcata cactattctc agaatgactt ggttgagtac tcaccagtca    4620
```

```
cagaaaagca tcttacggat ggcatgacag taagagaatt atgcagtgct gccataacca    4680
tgagtgataa cactgcggcc aacttacttc tgacaacgat cggaggaccg aaggagctaa    4740 ccgcttttt  gcacaacatg ggggatcatg taactcgcct tgatcgttgg gaaccggagc    4800
tgaatgaagc cataccaaac gacgagcgtg acaccacgat gctgtagcaa tggcaacaac    4860
gttgcgcaaa ctattaactg gcgaactact tactctagct tcccggcaac aattaataga    4920
ctggatggag gcggataaag ttgcaggacc acttctgcgc tcggcccttc cggctggctg    4980
gtttattgct gataaatctg gagccggtga gcgtgggtct cgcggtatca ttgcagcact    5040
ggggccagat ggtaagccct cccgtatcgt agttatctac acgacgggga gtcaggcaac    5100
tatggatgaa cgaaatagac agatcgctga gataggtgcc tcactgatta agcattggta    5160
actgtcagac caagtttact catatatact ttagattgat ttaaaacttc attttaatt    5220 taaaaggatc taggtgaaga tcctttttga taatctcatg accaaaatcc cttaacgtga    5280
gttttcgttc cactgagcgt cagaccccgt agaaaagatc aaaggatctt cttgagatcc    5340
tttttttctg cgcgtaatct gctgcttgca acaaaaaaa  ccaccgctac cagcggtggt    5400
ttgtttgccg gatcaagagc taccaactct ttttccgaag gtaactggct tcagcagagc    5460
gcagatacca aatactgtcc ttctagtgta gccgtagtta ggccaccact tcaagaactc    5520
tgtagcaccg cctacatacc tcgctctgct aatcctgtta ccagtggctg ctgccagtgg    5580
cgataagtcg tgtcttaccg ggttggactc aagacgatag ttaccggata aggcgcagcg    5640
gtcgggctga acggggggtt cgtgcacaca gcccagcttg gagcgaacga cctacaccga    5700
actgagatac ctacagcgtg agcattgaga aagcgccacg cttcccgaag ggagaaaggc    5760
ggacaggtat ccggtaagcg gcagggtcgg aacaggagag cgcacgaggg agcttccagg    5820
gggaaacgcc tggtatcttt atagtcctgt cgggtttcgc cacctctgac ttgagcgtcg    5880
atttttgtga tgctcgtcag ggggcggag  cctatggaaa aacgccagca acgcggcctt    5940
tttacggttc ctggcctttt gctggccttt tgctcacatg ttctttcctg cgttatcccc    6000
tgattctgtg gataaccgta ttaccgcctt tgagtgagct gataccgctc gccgcagccg    6060
aacgaccgag cgcagcgagt cagtgagcga ggaagcggaa gagcgcctga tgcggtattt    6120
tctccttacg catctgtgcg gtatttcaca ccgcatatgg tgcactctca gtacaatctg    6180
ctctgatgcc gcatagttaa gccagtatac actccgctat cgctacgtga ctgggtcatg    6240
gctgcgcccc gacacccgcc aacacccgct gacgcgccct gacgggcttg tctgctcccg    6300
gcatccgctt acagacaagc tgtgaccgtc tccgggagct gcatgtgtca gaggttttca    6360
ccgtcatcac cgaaacgcgc gaggcagctg cggtaaagct catcagcgtg gtcgtgaagc    6420
gattcacaga tgtctgcctg ttcatccgcg tccagctcgt tgagtttctc cagaagcgtt    6480
aatgtctggc ttctgataaa gcgggccatg ttaagggcgg ttttttcctg tttggtcact    6540
gatgcctccg tgtaagggg  atttctgttc atgggggtaa tgataccgat gaaacgagag    6600
aggatgctca cgatacgggt tactgatgat gaacatgccc ggttactgga acgttgtgag    6660
ggtaaacaac tggcggtatg gatgcggcgg gaccagagaa aaatcactca gggtcaatgc    6720
cagcgcttcg ttaatacaga tgtaggtgtt ccacagggta gccagcagca tcctgcgatg    6780
cagatccgga acataatggt gcagggcgct gacttccgcg tttccagact ttacgaaaca    6840
cggaaaccga agaccattca tgttgttgct caggtcgcag acgttttgca gcagcagtcg    6900
cttcacgttc gctcgcgtat cggtgattca ttctgctaac cagtaaggca accccgccag    6960
cctagccggg tcctcaacga caggagcacg atcatgcgca cccgtggcca ggacccaacg    7020
```

-continued

```
ctgcccgaga tgcgccgcgt gcggctgctg gagatggcgg acgcgatgga tatgttctgc    7080
caagggttgg tttgcgcatt cacagttctc cgcaagaatt gattggctcc aattcttgga    7140
gtggtgaatc cgttagcgag gtgccgccgg cttccattca ggtcgaggtg gcccggctcc    7200
atgcaccgcg acgcaacgcg gggaggcaga caaggtatag ggcggcgcct acaatccatg    7260
ccaacccgtt ccatgtgctc gccgaggcgg cataaatcgc cgtgacgatc agcggtccag    7320
tgatcgaagt taggctggta agagccgcga gcgatccttg aagctgtccc tgatggtcgt    7380
catctacctg cctggacagc atggcctgca acgcgggcat cccgatgccg ccggaagcga    7440
gaagaatcat aatggggaag gccatccagc ctcgcgtcgc gaacgccagc aagacgtagc    7500
ccagcgcgtc ggccgccatg ccggcgataa tggcctgctt ctcgccgaaa cgtttggtgg    7560
cgggaccagt gacgaaggct tgagcgaggg cgtgcaagat tccgaatacc gcaagcgaca    7620
ggccgatcat cgtcgcgctc cagcgaaagc ggtcctcgcc gaaaatgacc cagagcgctg    7680
ccggcacctg tcctacgagt tgcatgataa agaagacagt cataagtgcg gcgacgatag    7740
tcatgccccg cgcccaccgg aaggagctga ctgggttgaa ggctctcaag ggcatcggtc    7800
gacgctctcc cttatgcgac tcctgcatta ggaagcagcc cagtagtagg ttgaggccgt    7860
tgagcaccgc cgccgcaagg aatggtgcat gcaaggagat ggcgcccaac agtcccccgg    7920
ccacggggcc tgccaccata cccacgccga acaagcgct catgagcccg aagtggcgag    7980
cccgatcttc cccatcggtg atgtcggcga tataggcgcc agcaaccgca cctgtggcgc    8040
cggtgatgcc ggccacgatg cgtccggcgt agaggatccg ggcttatcga ctgcacggtg    8100
caccaatgct tctggcgtca ggcagccatc ggaagctgtg gtatggctgt gcaggtcgta    8160
aatcactgca taattcgtgt cgctcaaggc gcactcccgt tctggataat gttttttgcg    8220
ccgacatcat aacggttctg gcaaatattc tgaaatgagc tg                      8262
```

<210> SEQ ID NO 15
<211> LENGTH: 30
<212> TYPE: DNA
<213> ORGANISM: Artificial Sequence
<220> FEATURE:
<223> OTHER INFORMATION: PCR primer

<400> SEQUENCE: 15
gggtttccat ggaccagccg ctcaacgtgg                                      30

<210> SEQ ID NO 16
<211> LENGTH: 33
<212> TYPE: DNA
<213> ORGANISM: Artificial Sequence
<220> FEATURE:
<223> OTHER INFORMATION: PCR primer

<400> SEQUENCE: 16
gggttttcag gcgatgccgt tgagcgcttc gcc                                  33

<210> SEQ ID NO 17
<211> LENGTH: 26
<212> TYPE: DNA
<213> ORGANISM: Artificial Sequence
<220> FEATURE:
<223> OTHER INFORMATION: PCR primer

<400> SEQUENCE: 17
gggaacggcg gggaaaaaca aacgtt                                          26

<210> SEQ ID NO 18
<211> LENGTH: 30
<212> TYPE: DNA
<213> ORGANISM: Artificial Sequence
<220> FEATURE:
<223> OTHER INFORMATION: PCR primer

<400> SEQUENCE: 18

```
ggtccatggt aattctccac gcttataagc                                   30
```

<210> SEQ ID NO 19
<211> LENGTH: 85
<212> TYPE: DNA
<213> ORGANISM: E. coli

<400> SEQUENCE: 19

```
ggtttgaata aatgacaaaa agcaaagcct ttgtgccgat gaatctctat actgtttcac   60
agacctgctg ccctgcgggg cggcc                                        85
```

<210> SEQ ID NO 20
<211> LENGTH: 26
<212> TYPE: DNA
<213> ORGANISM: Artificial Sequence
<220> FEATURE:
<223> OTHER INFORMATION: PCR primer

<400> SEQUENCE: 20

```
gggaacggcg gggaaaaaca aacgtt                                       26
```

<210> SEQ ID NO 21
<211> LENGTH: 33
<212> TYPE: DNA
<213> ORGANISM: Artificial Sequence
<220> FEATURE:
<223> OTHER INFORMATION: PCR primer

<400> SEQUENCE: 21

```
gggttttcag gcgatgccgt tgagcgcttc gcc                               33
```

<210> SEQ ID NO 22
<211> LENGTH: 1754
<212> TYPE: DNA
<213> ORGANISM: Artificial Sequence
<220> FEATURE:
<223> OTHER INFORMATION: Codon-optimized pyruvate decarboxylase DNA
       sequence based on gene of Zymomonas mobilis.

<400> SEQUENCE: 22

```
catatgtcct acactgttgg tacttatctg gctgaacgtc tggttcaaat tggtctgaag   60
catcactttg cggtagcggg cgattacaac ctggtgctgc tggataatct gctgctgaac  120
aaaaacatgg aacaggtcta ctgttgtaac gaactgaact gcggcttctc tgctgaaggt  180
tatgcccggg ccaaaggcgc agctgcggcc gtagtgacct actccgttgg tgctctgtcc  240
gcatttgatg caattggtgg cgcctacgca gaaaacctgc cggtaattct gatctctggc  300
gctccgaaca caacgatca cgcagctggt cacgtgctgc accatgcgct gggcaaaact  360
gattatcatt accagctgga aatggcgaag aacatcactg ccgcagcaga agctatctat  420
actccagaag aagcgccggc aaaaatcgat catgtaatca aaacggccct gcgtgagaag  480
aaaccggtgt atctggaaat tgcttgtaat atcgcgtcta tgccgtgtgc ggccccaggc  540
ccagcatctg ctctgtttaa cgatgaagct agcgatgaag cctctctgaa cgcagctgtg  600
gaagaaaccc tgaaattcat tgcaaaccgt gacaaagttg cggtactggt tggctctaaa  660
```

-continued

```
ctgcgtgccg cgggtgcaga agaagcggcg gttaaattcg ctgacgccct gggtggtgct    720
gtggccacca tggctgcggc taaatccttt ttcccggaag aaaatccgca ttacatcggt    780
acttcctggg gcgaggtttc ttacccaggt gtcgagaaaa ccatgaagga agctgacgcg    840
gtgatcgccc tggccccggt tttcaatgac tactccacta ctggttggac cgacatcccg    900
gacccaaaga aactggttct ggcagagccg cgctccgttg ttgttaacgg tattcgcttt    960
ccgtccgtac acctgaagga ttatctgact cgtctggcgc agaaagtgag caagaaaacc   1020
ggcgctctgg atttctttaa atctctgaat gcgggtgagc tgaagaaagc cgcaccggcg   1080
gacccttctg ctccgctggt taacgccgaa attgcgcgcc aggtagaagc gctgctgact   1140
ccgaatacta ccgtaattgc ggagactggc gattcctggt caacgcacag acgtatgaag   1200
ctgcctaacg gcgctcgagt tgaatacgaa atgcagtggg gccacatcgg ctggtctgtt   1260
cctgcagcct tcggctacgc cgtaggtgct ccggaacgtc gtaacatcct gatggtcggt   1320
gacggtcttt tccaactgac cgcgcaggaa gtagcacaga tggttcgtct gaaactgccg   1380
gtaatcatct tcctgattaa caactacggc tataccattg aggtcatgat tcatgatggt   1440
ccgtataata acatcaaaaa ctgggattat gctggtctga tggaagtttt caacggcaac   1500
ggcggctacg attctggtgc tggtaaaggc ctgaaagcaa agacgggtgg cgagctcgca   1560
gaagcgatca aggttgctct ggctaacacc gatggtccga ctctgatcga atgttttatc   1620
ggtcgtgaag attgcactga ggaactggtg aagtggggta agcgtgtggc tgccgcgaat   1680
tcccgtaaac cggtaaataa gcttctcggc catcaccatc accatcacta gaagcttctc   1740
tagagaacta tttc                                                     1754
```

<210> SEQ ID NO 23
<211> LENGTH: 575
<212> TYPE: PRT
<213> ORGANISM: Zymomonas mobilis

<400> SEQUENCE: 23

```
Met Ser Tyr Thr Val Gly Thr Tyr Leu Ala Glu Arg Leu Val Gln Ile
1               5                   10                  15

Gly Leu Lys His His Phe Ala Val Ala Gly Asp Tyr Asn Leu Val Leu
            20                  25                  30

Leu Asp Asn Leu Leu Leu Asn Lys Asn Met Glu Gln Val Tyr Cys Cys
        35                  40                  45

Asn Glu Leu Asn Cys Gly Phe Ser Ala Glu Gly Tyr Ala Arg Ala Lys
    50                  55                  60

Gly Ala Ala Ala Ala Val Val Thr Tyr Ser Val Gly Ala Leu Ser Ala
65                  70                  75                  80

Phe Asp Ala Ile Gly Gly Ala Tyr Ala Glu Asn Leu Pro Val Ile Leu
                85                  90                  95

Ile Ser Gly Ala Pro Asn Asn Asn Asp His Ala Ala Gly His Val Leu
            100                 105                 110

His His Ala Leu Gly Lys Thr Asp Tyr His Tyr Gln Leu Glu Met Ala
        115                 120                 125

Lys Asn Ile Thr Ala Ala Ala Glu Ala Ile Tyr Thr Pro Glu Glu Ala
    130                 135                 140

Pro Ala Lys Ile Asp His Val Ile Lys Thr Ala Leu Arg Glu Lys Lys
145                 150                 155                 160

Pro Val Tyr Leu Glu Ile Ala Cys Asn Ile Ala Ser Met Pro Cys Ala
                165                 170                 175

Ala Pro Gly Pro Ala Ser Ala Leu Phe Asn Asp Glu Ala Ser Asp Glu
```

```
                    180              185              190
Ala Ser Leu Asn Ala Ala Val Glu Glu Thr Leu Lys Phe Ile Ala Asn
        195                  200              205

Arg Asp Lys Val Ala Val Leu Val Gly Ser Lys Leu Arg Ala Ala Gly
        210              215              220

Ala Glu Glu Ala Ala Val Lys Phe Ala Asp Ala Leu Gly Gly Ala Val
225              230              235              240

Ala Thr Met Ala Ala Lys Ser Phe Phe Pro Glu Asn Pro His
                245              250              255

Tyr Ile Gly Thr Ser Trp Gly Glu Val Ser Tyr Pro Gly Val Glu Lys
            260              265              270

Thr Met Lys Glu Ala Asp Ala Val Ile Ala Leu Ala Pro Val Phe Asn
            275              280              285

Asp Tyr Ser Thr Thr Gly Trp Thr Asp Ile Pro Asp Pro Lys Lys Leu
        290              295              300

Val Leu Ala Glu Pro Arg Ser Val Val Asn Gly Ile Arg Phe Pro
305              310              315              320

Ser Val His Leu Lys Asp Tyr Leu Thr Arg Leu Ala Gln Lys Val Ser
                325              330              335

Lys Lys Thr Gly Ala Leu Asp Phe Phe Lys Ser Leu Asn Ala Gly Glu
            340              345              350

Leu Lys Lys Ala Ala Pro Ala Asp Pro Ser Ala Pro Leu Val Asn Ala
        355              360              365

Glu Ile Ala Arg Gln Val Glu Ala Leu Leu Thr Pro Asn Thr Thr Val
370              375              380

Ile Ala Glu Thr Gly Asp Ser Trp Phe Asn Ala Gln Arg Met Lys Leu
385              390              395              400

Pro Asn Gly Ala Arg Val Glu Tyr Glu Met Gln Trp Gly His Ile Gly
                405              410              415

Trp Ser Val Pro Ala Ala Phe Gly Tyr Ala Val Gly Ala Pro Glu Arg
            420              425              430

Arg Asn Ile Leu Met Val Gly Asp Gly Ser Phe Gln Leu Thr Ala Gln
            435              440              445

Glu Val Ala Gln Met Val Arg Leu Lys Leu Pro Val Ile Ile Phe Leu
        450              455              460

Ile Asn Asn Tyr Gly Tyr Thr Ile Glu Val Met Ile His Asp Gly Pro
465              470              475              480

Tyr Asn Asn Ile Lys Asn Trp Asp Tyr Ala Gly Leu Met Glu Val Phe
                485              490              495

Asn Gly Asn Gly Gly Tyr Asp Ser Gly Ala Gly Lys Gly Leu Lys Ala
            500              505              510

Lys Thr Gly Gly Glu Leu Ala Glu Ala Ile Lys Val Ala Leu Ala Asn
            515              520              525

Thr Asp Gly Pro Thr Leu Ile Glu Cys Phe Ile Gly Arg Glu Asp Cys
        530              535              540

Thr Glu Glu Leu Val Lys Trp Gly Lys Arg Val Ala Ala Ala Asn Ser
545              550              555              560

Arg Lys Pro Val Asn Lys Leu Leu Gly His His His His His
                565              570              575
```

COMPOSITIONS AND METHODS FOR 3-HYDROXYPROPIONATE BIO-PRODUCTION FROM BIOMASS

RELATED APPLICATIONS

This application is a continuation application which claims priority under 35 USC 120 to U.S. Pat. No. 8,048,624 filed Dec. 4, 2008, and this application also claims priority under 35 USC 119 to U.S. Provisional Patent Application No. 60/992,290, filed Dec. 4, 2007. Both referenced patent applications are incorporated by reference in their respective entireties herewith.

STATEMENT REGARDING FEDERALLY SPONSORED DEVELOPMENT

N/A

REFERENCE TO A SEQUENCE LISTING

An electronically filed sequence listing is provided herewith.

FIELD OF THE INVENTION

The present invention relates to methods, systems and compositions, including genetically modified microorganisms, i.e., recombinant microorganisms, adapted to exhibit elevated oxaloacetate alpha-oxo decarboxylase activity (also referred to herein as oxaloacetate alpha-decarboxylase activity).

BACKGROUND OF THE INVENTION 3-hydroxypropionate ("3-HP", CAS No. 503-66-2) has been identified as a highly attractive potential chemical feedstock for the production of many large market commodity chemicals that are currently derived from petroleum derivatives. For example, commodity products that can be readily produced using 3-HP include acrylic acid, 1,3-propanediol, methyl-acrylate, and acrylamide, as shown in FIG. 1. The sum value of these commodity chemicals is currently estimated to exceed several billions of dollars annually in the US. However, the current petrochemical manufacturing techniques for these commodities adverse impact the environment via the pollutants generated and the energy used in their production. Manufacture of these same commodities via the clean, cost-effective, production of 3-HP from biomass will simultaneously reduce toxic waste and substitute renewable feed stocks for non-renewable resources. In addition to the environmental benefits associated with bio-based production of 3-HP, if the production cost of the derived commodities is substantially reduced relative to petroleum-based production, this would make a biorefining industry not only environmentally beneficial but also a very attractive investment.

Previous attempts to produce 3-HP via biological pathways provide product titers which have been low and these processes have required the use of expensive, rich media. Both of these factors limit commercial feasibility and profitability. The use of rich media was necessary due to the toxicity of 3-HP when fermented with the more economical minimal media. For example, in wild type *E. coli*, metabolic activity is significantly inhibited at levels of 3-HP that are 5-10 times lower than the approximate 100 g/L titer needed for economic feasibility using the more economical minimal media. In fact, toxic effects have also been observed in rich media at product titers which are approximately two times lower than desired titers for commercial feasibility (Refer to FIG. 2). Further, the fermentative pathways reported by other investigators have not addressed and resolved the toxicity mechanisms of 3-HP to the host organisms.

Further to issues related to commodity chemical production, which largely relies on petroleum-based starting materials, there is an increasing need to reduce the domestic usage of petroleum and natural gas. The numerous motivating factors for this increasing need include, but are not limited to: pollutant reduction (such as greenhouse gases), environmental protection, and reducing the dependence on foreign oil. These issues not only impact fuel markets, but also the markets of numerous other products that are currently derived from oil. Biorefining promises the development of efficient biological processes allowing for the conversion of renewable sources of carbon and energy into large volume commodity chemicals.

A biosynthetic route to 3-HP as a platform chemical would be of benefit to the public, not only in terms of reduced dependence on petroleum, but also by a reduction in the amount of pollutants that are generated by current non-biosynthetic processes. Because 3-HP is not currently used as a building block for the aforementioned commodity chemicals, technical hurdles must be surmounted to achieve low cost biological routes to 3-HP. These hurdles include the development of a new organism that not only has a metabolic pathway enabling the production of 3-HP, but is also tolerant to the toxic effects of 3-HP thus enabling the sustained production of 3-HP at economically desired levels.

There are numerous motivating factors to reduce the domestic usage of petroleum. These factors include, but are not limited to: 1) the negative environmental impacts of petroleum refining such as production of greenhouse gases and the emission of a wide variety of pollutants; 2) the national security issues that are associated with the current dependence on foreign oil such as price instability and future availability; and 3) the long term economic concerns with the ever-increasing price of crude oil. These issues not only impact fuel markets, but also the multi-billion dollar commodity petro-chemical market One potential method to alleviate these issues is the implementation of bioprocessing for the conversion of renewable feed stocks (e.g. agricultural wastes) to large volume commodity chemicals. It has been estimated that such bioprocesses already account for 5% of the 1.2 trillion dollar US chemical market. Furthermore, some experts are projecting that up to 50% of the total US chemical market will ultimately be generated through biological means.

While the attractiveness of such bioprocesses has been recognized for some time, recent advances in biological engineering, including several bio-refining success stories, have accelerated interest in the large scale production of chemicals through biological routes. However, many challenges still remain for the economical bio-production of commodity chemicals. These challenges include the need to convert biomass into usable feed stocks, the engineering of microbes to produce relevant chemicals at high titers and productivities, the improvement of the microbes' tolerance to the desired product, and the need to minimize the generation of byproducts that might affect downstream processes. Finally, the product must be economically competitive in the marketplace.

The contributions of bioprocessing are expected to grow in the future as existing biological methods become more efficient and as new bioprocesses are developed. A recent analysis by the U.S. Department of Energy identified a list of the Top Value Added Chemicals from Biomass that are good candidates for biosynthetic production. Eight of the top value added chemicals were organic acids, including 3-hydroxypropionic acid (3-HP). As depicted in FIG. 1, 3-HP is considered to be a platform chemical, capable of yielding valuable derivative commodity chemicals including acrylic acid and acrylic acid polymers, acrylate esters, acrylate polymers (plastics), acrylamide, and 1,3-propanediol. Presently, these high value chemicals are produced from petroleum.

One method to efficiently generate 3-HP by a bioprocess approach would be the microbial biosynthesis of renewable biomass sugars to 3-HP. According to the DOE Report (Werpy, T.; Petersen, G. Volume 1: Results of Screening for Potential Candidates from Sugars and Synthetic Gas. Oak Ridge, Tenn., *U.S. Department of Energy;* 2004. *Top Value Added Chemicals from Biomass*), a number of factors will need to be addressed, including: identifying the appropriate biosynthetic pathway, improving the reactions to reduce other acid co-products, increasing microbial yields and productivities, reducing the unwanted salts, and scale-up and integration of the system. Additionally, as noted above, it is critical to engineer the microbial organism to be tolerant to the potential toxicity of the desired product at commercially significant concentrations.

The production of acrylic acid from 3-HP is of particular interest because of the high market value of acrylic acid and its numerous derivatives. In 2005, the estimated annual production capacity for acrylic acid was approximately 4.2 million metric tons, which places it among the top 25 organic chemical products. Also, this figure is increasing annually. The demand for acrylic acid may exceed $2 billion by 2010. The primary application of acrylic acid is the synthesis of acrylic esters, such as methyl, butyl or ethyl acrylate. When polymerized, these acrylates are ingredients in numerous consumer products, such as paints, coatings, plastics, adhesives, dispersives and binders for paper, textiles and leather. Acrylates account for 55% of the world demand for acrylic acid products, with butyl acrylate and ethyl acrylate having the highest production volumes. The other key use of the acrylic acid is through polymerization to polyacrylic acid, which is used in hygiene products, detergents, and waste water treatment chemicals. Acrylic acid polymers can also be converted into super absorbent materials (which account for 32% of worldwide acrylic acid demand) or developed into replacement materials for phosphates in detergents. Both of these are fast growing applications for acrylic acid. Today, acrylic acid is made in a two step catalytic oxidation of propylene (a petroleum product) to acrolein, and acrolein to acrylic acid, using a molybdenum/vanadium based catalyst, with optimized yields of approximately 90%. It should be noted that several commercial manufacturers of acrylic acid are exploring the use of propane instead of propylene. The use of propane is projected to be more environmentally friendly by reducing energy consumption during production. However, propane is petroleum based, and while its use is a step in the right direction from an energy consumption standpoint, it does not offer the benefits afforded by the bioprocessing route.

In addition to acrylic acid, acrylates, and acrylic acid polymers, another emerging high value derivative of 3-HP is 1,3-propanediol (1,3-PD). 1,3-PD has recently been used in carpet fiber production for carpets. Further applications of 1,3-PD are expected to include cosmetics, liquid detergents, and anti-freeze. The market for 1,3-PD is expected to grow rapidly as it becomes more routinely used in commercial products.

Pursuing a cleaner, renewable carbon source route to commodity chemicals through 3-HP will require downstream optimization of the chemical reactions, depending on the desired end product. 3-HP production through bioprocesses directly, or through reaction routes to the high-value chemical derivatives of 3-HP will provide for large scale manufacture of acrylic acid, as well reduction of environmental pollution, the reduction in dependence on foreign oil, and the improvement in the domestic usage of clean methods of manufacturing. Furthermore, the products produced will be of the same quality but at a competitive cost and purity compared to the current petroleum based product.

Thus, notwithstanding various advances in the art, there remains a need for methods that identify and/or provide, and compositions directed to recombinant microorganisms that have improved 3-HP production capabilities, so that increased 3-HP titers are achieved.

BRIEF DESCRIPTION OF THE DRAWINGS

FIGS. 4A-4C-1-2 depict the SCALEs data identifying the chorismate superpathway as a 3-HP target. (A) Fitness data for positions and scales conferring increased fitness of *E. coli* in the presence of 3-HP. Genomic position correlates to position around the circle and scale is represented by color (red=500-1000 bp, yellow=1000-2000 bp, green=4000-8000 bp, blue=8000-10000 bp). The height of the peak above the circle correlates to the fitness of a given scale at a given position. Peaks corresponding to genes involved in the chorismate superpathway are numbered. (B) List of genes in the chorismate superpathway identified in (A). (C1-2) The fitness of each gene identified in (A) is color coded and identified in the chorismate superpathway.

FIG. 10B depicts the anticipated Selection Results of mutant colonies expressing the desired oxaloacetate alpha-decarboxylase will grow on the minimal media when expressed in *E. coli* AB354 expressing gabT. No growth will be observed under these conditions in the *E. coli* AB354, *E. coli* AB354+gabT controls, or in kgd mutants not expressing the desired activity.

DETAILED DESCRIPTION OF EMBODIMENTS OF THE INVENTION

Figure 1:
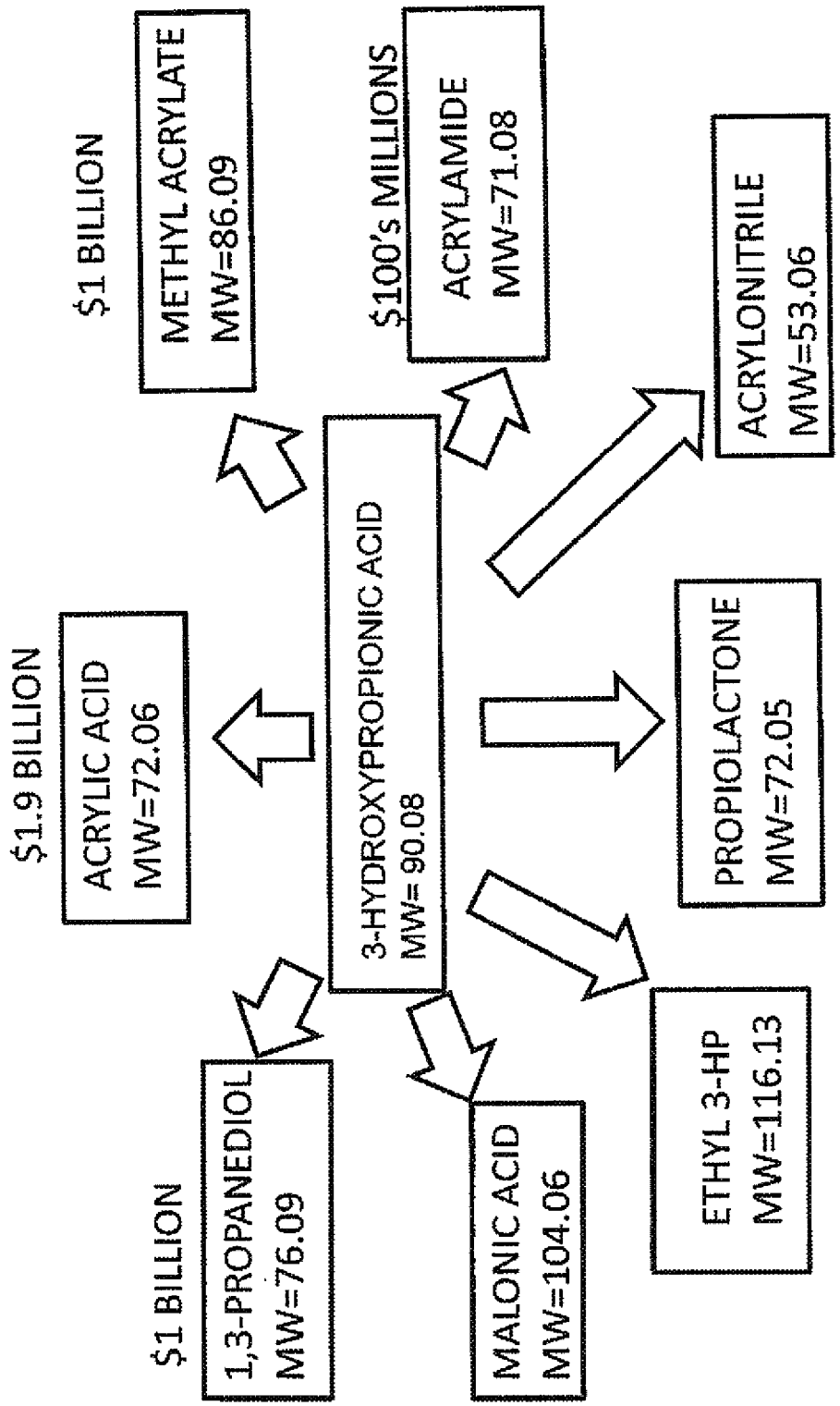
FIG. 1 depicts how biomass derived 3-HP can serve as a chemical feedstock to many major chemical commodities worth billions of dollars. (Adapted from Werpy et al. US Dept. Energy, 2004).

Generally the invention is directed to compositions and methods for production of target chemical compounds in an organism. Various aspects of the invention are directed to providing altered/modified proteins having different enzymatic activity/function as compared to the unaltered protein. Further aspects, of the invention are directed to recombinant organisms comprising altered/modified pathways which are enhanced for production of a target compound (e.g., 3-HP). In some embodiments, a recombinant organism of the invention is a microorganism or algae. In further embodiments, a recombinant organism is a bacterium (e.g., *E. coli*).

In one aspect of the invention, an organism is modified to include one or more genes encoding a protein involved in biosynthesis to enhance production of a target chemical compound (e.g., 3-HP). In further embodiments, such one or more genes encode one or more proteins which enhance the capability of the organism to produce a target chemical compound in culture. In one embodiment, such a chemical compound is 3-HP. In yet a further embodiment, the organism comprises at least one recombinant gene resulting in pyruvate, oxalocetate and acetyl-coA production without committed formate production.

In another embodiment, the recombinant organism comprises acetyl-coA that is produced via the intermediate malonate semialdehyde. In yet another embodiment, acetyl-coA is produced via the intermediate pyruvate through pyruvate synthase.

Another aspect of the invention is directed to a method for producing 3-HP comprising growing a recombinant organism of the invention, where the organism comprises an enzyme which converts oxaloacetate to malonate semialdehyde. In further embodiments, the recombinant organism is engineered to delete or substantially reduce activity of one or more genes, where the gene(s) include but are not limited to pfkA, pfkB, ldhA, pta, poxB, pflB or a combination thereof. In yet a further embodiment, the recombinant organism is modified to enhance the activity (such as by increasing expression or improving the relevant functioning) of one or more enzymes including but not limited to pck, mmsA, mmsB, oad-2, homologs thereof, or any combination thereof.

In one embodiment, a method is provided for producing 3-HP comprising growing an organism under a condition which enhance said 3-HP production, wherein said condition is selected from acetyl-coA production via malonate semialdehyde, acetyal-coA production via pyruvate by pyrvuate synthase, without committed production of formate, homologs thereof and any combination thereof.

In a further aspect of the invention a recombinant microorganism is provided capable of producing 3-HP at quantities greater than about 10, 15, 20, 30, 40, 50, 60, 65, 70, 75, 80, 85, 90, 95, 100, 105, 110, 115, 120, 125, 130, 135, 140 145 or 150 g/L. In one embodiment, the recombinant organism is capable of producing 3-HP from about 30 to about 100 g/L of biomass/culture.

In a further aspect of the invention, a bio-production mixture is provided for producing 3HP, said mixture comprising a recombinant microorganism; one or more products selected from a group consisting tyrosine, phenylalanine, para-aminobenzoate, para-hydroxy-benzoate, 2,3,-dihydrobenzoate and shikimate.

In further embodiments, the mixture comprises a microorganism which is engineered to produce pck, mmsA, mmsB, oad-2, homologs thereof, or a combination thereof. In further embodiments, the microorganism does not produce enzymes selected from a group consisting of pfkA, pfkB, ldhA, pta, poxB, pflB, homologs thereof and a combination thereof. In various embodiments, the microorganism is $E.\ coli$.

In one aspect of the invention, an isolated polypeptide is provided possessing oxaloacetate alpha oxo-decarboxylase activity, converting oxaloacetate to malonate semialdehyde. Furthermore, a nucleic acid encoding the polypeptide is provided. In yet a further embodiments, a functional variant for the polypeptide or nucleic acid sequence is provided which is homologous to the reference polypeptide and/or nucleic acid and functions as an oxaloacetate alpha oxo-decarboxylase. In some embodiments such a functional variant has at least about 50%, 55%, 60%, 65%, 70%, 75%, 80%, 85%, 90%, 95%, 96, 97, 98, or 99% identity with alpha-ketoglutarate decarboxylase.

Accordingly, in various aspects of the invention improved methods for biomass production of 3-HP at higher concentrations are disclosed. With this development, it is feasible to construct $E.\ coli$ strains that are highly tolerant to 3-HP and that will maintain robust metabolic activity in the presence of higher concentrations of 3-HP. In various embodiments, metabolic pathways which support the bio-production of 3-HP are manipulated to increase 3-HP production. In some embodiments, such metabolic pathways do not rely upon or are not affected by metabolic processes that are themselves inhibited by 3-HP.

Utilizing processes for identification of a 3-HP insensitive bio-production pathway (infra, under "Metabolic Toxicity of 3-HP"), in various embodiments of the invention a bio-production pathway is characterized for the synthesis of 3-HP in $E.\ coli$. In a further embodiment, an altered 2-oxo acid decarboxylase is utilized in a bio-production pathway to produce 3-HP. In yet further embodiments, a bio-production pathway is utilized incorporating previously characterized and sequenced enzymes that have been reported in the literature, as discussed below under "Previously Characterized Enzymes".

In various embodiments, a bio-production pathway (shown in FIG. 6) relies directly or indirectly on the metabolite oxaloacetate through the intermediate malonate semialdehyde. The desired enzymatic activity carries out the conversion of oxaloacetate to malonate semialdehyde. This can be accomplished via a decarboxylation reaction not previously reported by a particular enzyme. More specifically, the decarboxylation of 2-oxo acids, such as oxaloacetate, is accomplished by a well understood set of thiamine pyrophosphate dependant decarboxylases, including pyruvate decarboxylases and branched chain 2-oxo acid decarboxylases. A more recently characterized enzyme from $M.\ tuberculosis$, alpha ketoglutarate decarboxylase, coded by the kgd gene, possesses catalytic activity with a primary substrate very similar to oxaloacetate, decarboxylating the metabolite alpha-ketoglutarate to succinate semialdehyde. As described in greater detail below, an alpha-ketoglutarate decarboxylase from $M.\ tuberculosis$ is modified into an oxaloacetate alpha-oxo-decarboxylase or a functional variant thereof. In various embodiments, any 2-oxo acid decarboxylase including but not limited to pyruvate decarboxylases form various sources or branched chain 2-oxo acid decarboxylases are modified into an oxaloacetate alpha-oxo decarboxylase or a functional variant thereof. In various embodiments, a "functional variant" is a protein encoded by a sequence having about 50, 55, 60, 65, 70, 75, 80, 85, 90, 95, 96, 97, 98, or 99 percent identity with the nucleic acid sequence encoding the modified/altered oxaloacetate alpha-oxo-decarboxylase. In further embodiments, sequence identity can be on the amino acid sequence level, where a functional variant has a sequence identity with the reference sequence of about 50, 55, 60, 65, 70, 75, 80, 85, 90, 95, 96, 97, 98, or 99. For example, a functional variant can have sequence identity that is 90 percent, or 95 percent, but where the enzyme still functions as an oxaloacetate alpha-oxo-decarboxylase when expressed in an organism (e.g., microorganism, algae, plant), such as $E.\ coli$.

In other embodiments, a microorganism or algae is engineered to follow a preferred 3-HP bio-production pathway and also to enhance tolerance to 3-HP production at commercially viable levels. In some such embodiments, the microorganism is a bacterium, such as $E.\ coli$. Thus, as one example an $E.\ coli$ strain is constructed and optimized for a desired pathway as discussed herein, wherein enhanced tolerance to 3-HP also is established so as to produce commercially viable titers of product. Accordingly, it is within the conception of the present invention that its teachings, methods and compositions may be combined with other teachings, methods and compositions more specifically directed to 3-HP tolerance improvement, including co-owned and/or licensed inventions.

Metabolic Toxicity of 3-HP

Figure 2:
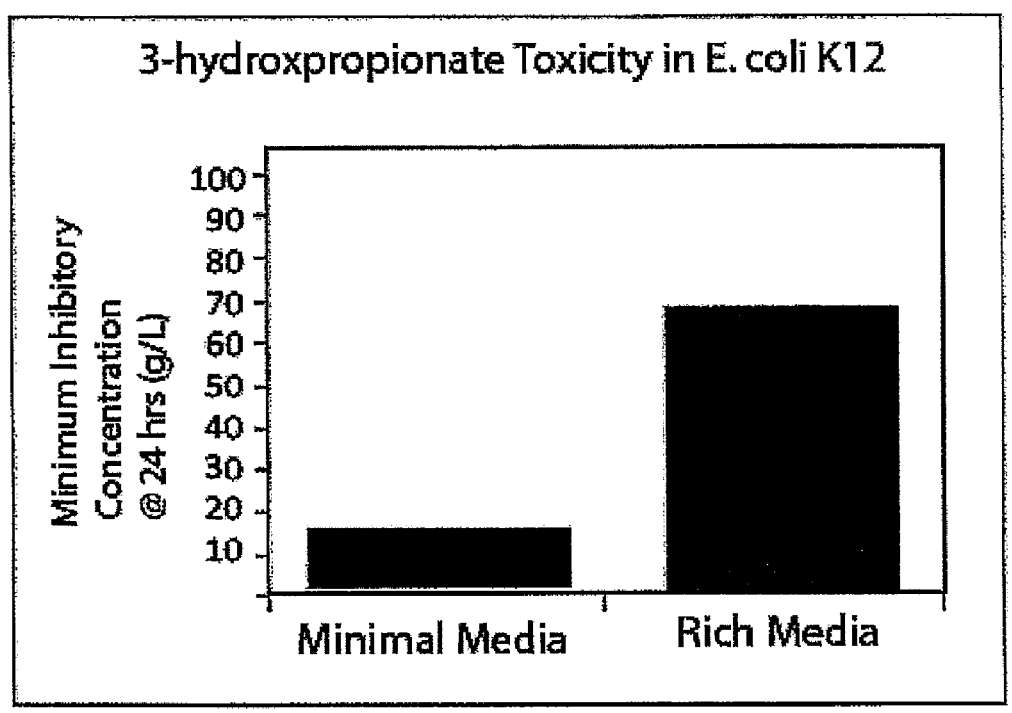
FIG. 2 depicts 3-hydroxpropionate toxicity in *E. coli* K12. The minimum concentration of 3-HP that is required to inhibit visible growth after 24 hrs in minimal media is shown for wild type *E. coli* K12 grown in both minimal media and rich media which contains more complex nutrients.

Severe growth inhibition has been observed for extracellular 3-HP levels as low as 10 g/L in minimal media (pH 7.0), which limits the economic feasibility of 3-HP production as a platform chemical. FIG. 2 demonstrates the toxic affects of 3-HP on $E.\ coli$ when grown in minimal media. These toxic effects have been observed to be far greater when the strains are grown in minimal media as compared to growth in rich media (containing a mixture of all nutrients, amino acids and vitamins). However toxicity at levels below required titers (100 g/L) are still observed in rich media. These data alone indicate that 3-HP may be exerting toxic effects by suppressing central metabolic pathways essential to amino acid metabolism.

Diagnosis of 3-HP Toxicity Mechanisms

Figure 3:
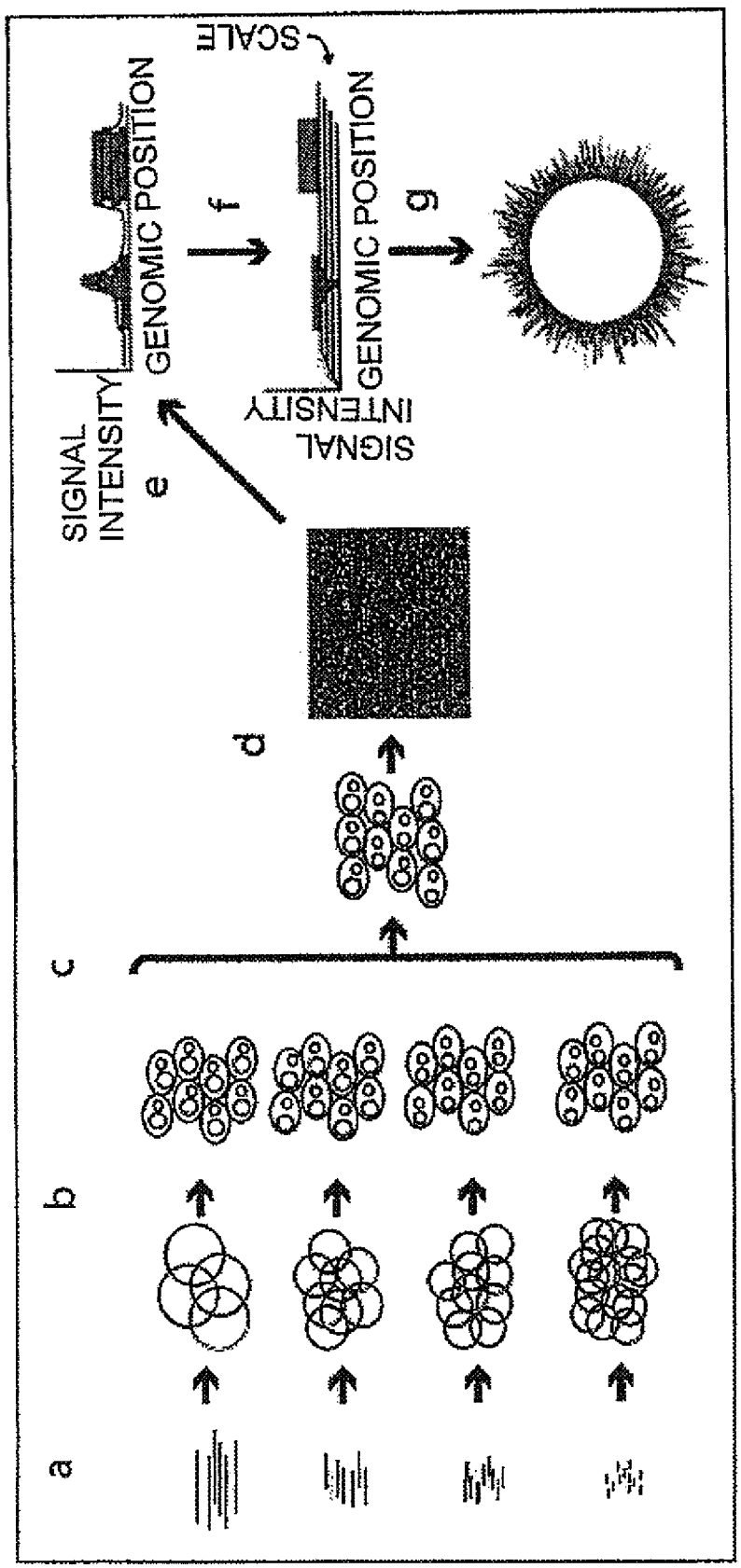
FIG. 3 is an overview of SCALEs. (a) Genomic DNA is fragmented to several specific sizes and ligated into vectors creating libraries with defined insert sizes. (b) These libraries are individually transformed into the host cell line used for selections. (c) The pools of transformants are mixed and subjected to selection. Clones bearing inserts with increasing fitness in a given selection have a growth advantage. (d) Enriched plasmids are purified from the selected population, prepared for hybridization, and applied to a microarray. (e) The processed microarray signal is analyzed as a function of genomic sequence position. (f) A nonlinear multi-scale analysis decomposition gives signal not only as a function of position but as a function of scale or library size. (g) Data are visualized and analyzed as a function of genomic position and scale. (for the circular chromosome of *E. coli* shown, genomic position correlates to position around the circle and scale is represented by color. The height of the peak above the circle correlates to population frequency or fitness of a given scale at a given position.)

To better understand the toxic effects of 3-HP on $E.\ coli$, a genome-wide technology is used (multi-Scale Analysis of Library Enrichments (SCALEs)), such as disclosed in U.S. Patent Application Publication No. 20060084098, with related inventions described in U.S. Patent Application Publication Nos. 20080103060 and 200702185333 (the latter entitled "Enhanced Alcohol Tolerant Microorganism and Methods of Use Thereof,) published Sep. 20, 2007), which are incorporated by reference herein in their entirety for their respective teachings of methods that provide important information which may be analyzed to make a discovery of previously unappreciated metabolic relationships. An overview of the SCALES approach as well as sample data are depicted in FIG. 3.

This genome-wide approach allows identification of numerous genetic changes that can reduce the toxic effects of 3-HP. The results of our studies (shown in FIG. 4) identified hundreds of genes and other genetic elements that when at increased copy confer varying levels of tolerance to the presence of 3-HP in E. coli. When applied alone, these genetic changes may allow for small increases in tolerance; but when applied together they allow for insight into the 3-HP toxicity mechanisms. By grouping genetic elements that confer tolerance by their metabolic roles key metabolic pathways that are inhibited by 3-HP were identified.

Figure 4A:
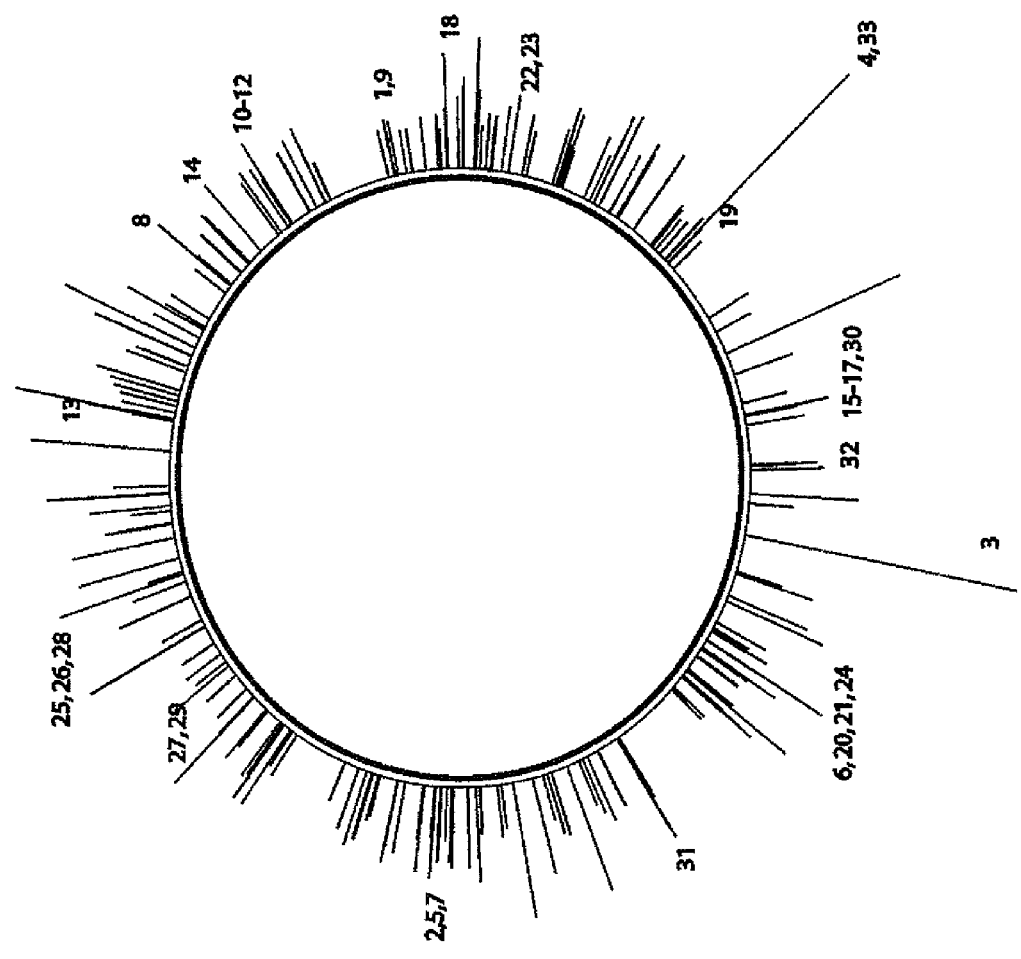
Figures 1, 4C:
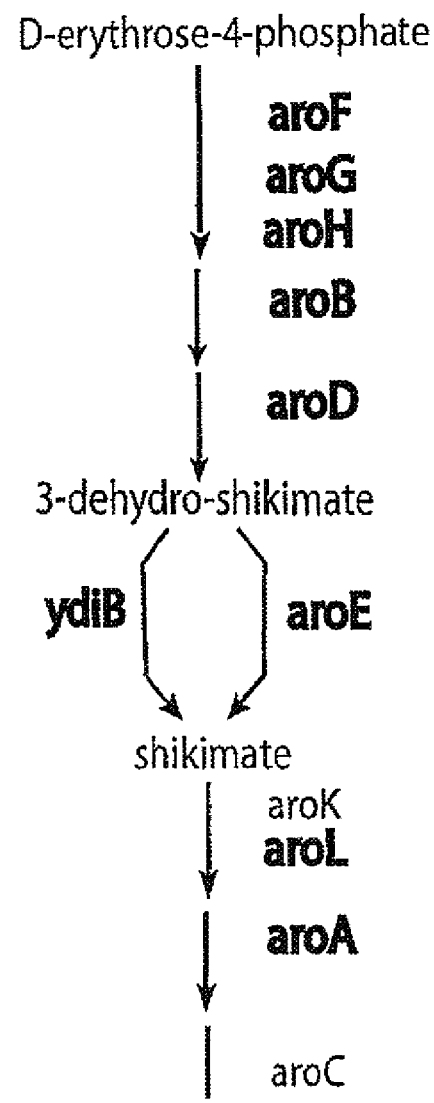
Figures 2, 4C:
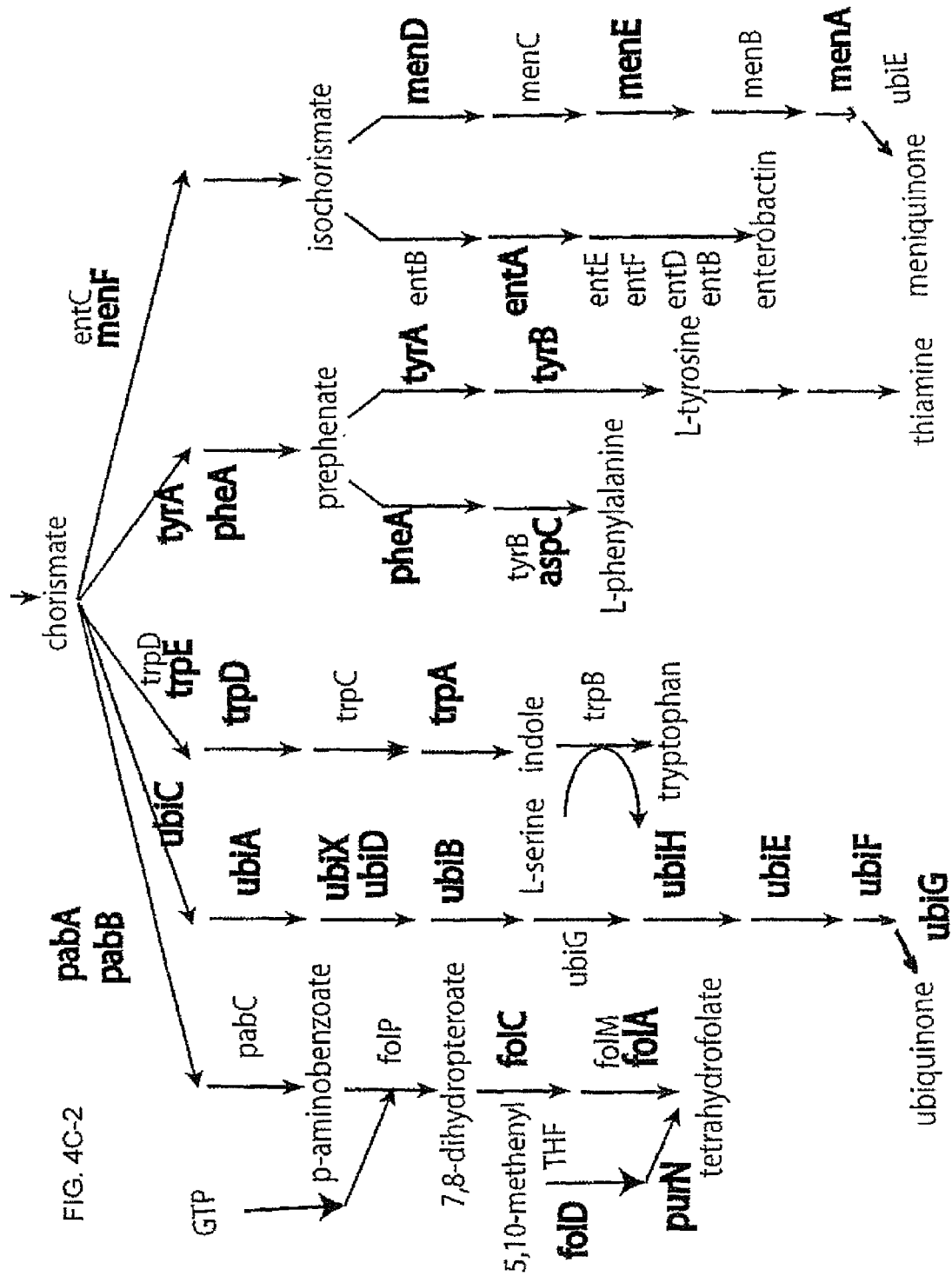

The data shown in FIG. 4 depict identification of the chorismate superpathway as a target of 3-HP toxicity. In some embodiments, toxicity is alleviated by several processes. For example, the addition of the downstream products of branches of the chorismate superpathway, tyrosine, phenylalanine, para-aminobenzoate (a tetrahydrofolate precursor), para-hydroxy-benzoate (a precursor of ubiquinone) and 2,3-dihydroxybenzoate (an enterobactin precursor) all alleviate toxicity to a degree.

A 3-HP Bio Production Pathway

Figure 5A:
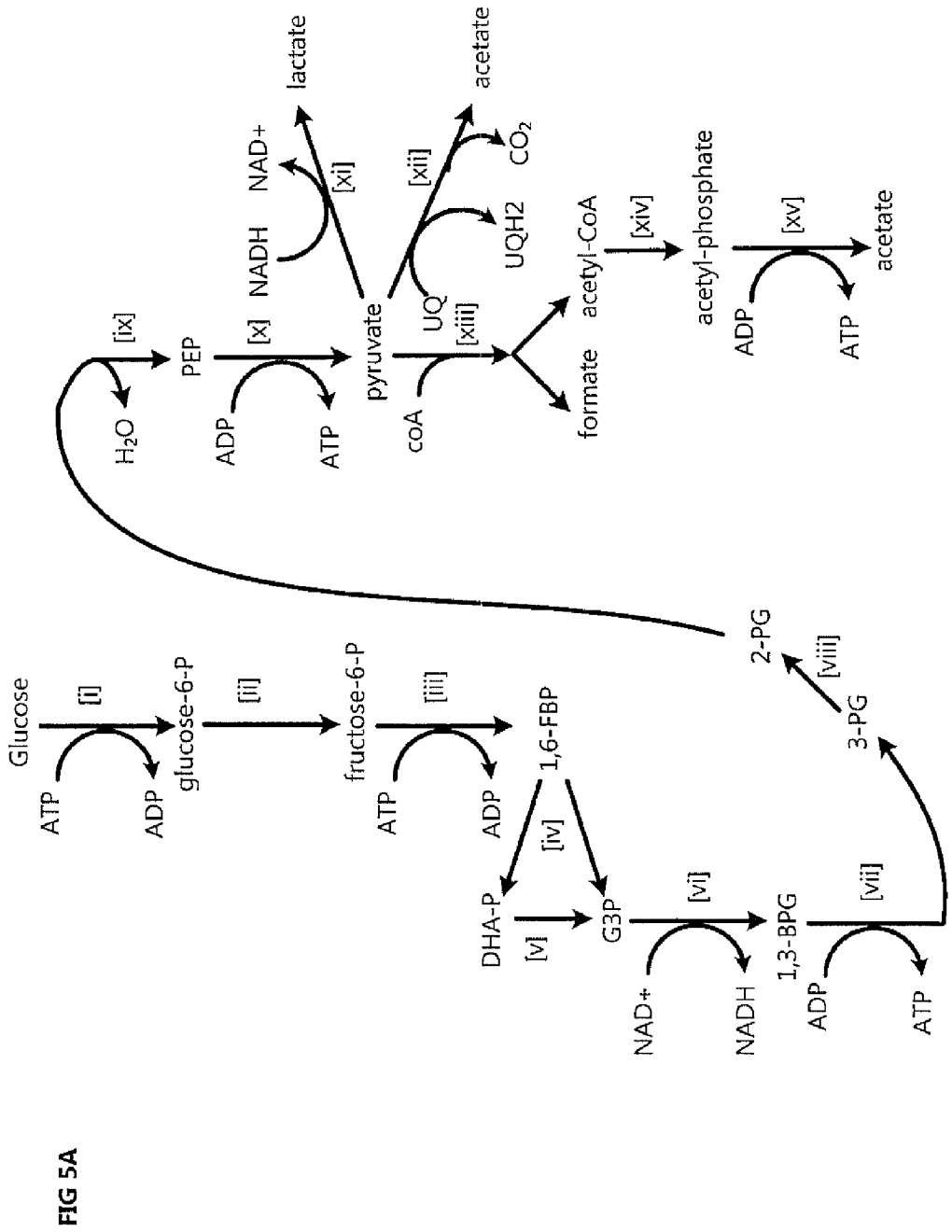
FIG. 5A This figure depicts the natural metabolic pathways utilize by *E. coli* during bio-production which results in the natural products lactate, formate and acetate FIG. 5B. The proposed metabolic pathway to produce 3-HP as a bio-production product. Arrows represent enzymatic activities. The non natural enzymatic function to be evolved in this Phase I project is colored in red. Enzyme activities are as follows [i] glucokinase, [ii] phosphoglucose isomerase, [iii] 6-phosphofructose kinase, [iv] fructose bisphosphate aldolase, [v] triose-phosphate isomerase, [vi] glyceraldehydes 3-phosphate dehydrogenase, [vii] phosphoglycerate kinase, [viii] phosphoglycerate mutase, [ix] enolase, [xi] pyruvate kinase, [xi] lactate dehydrogenase, [xii] pyruvate oxidase, [xiii] pyruvate-formate lyase, [xiv] phosphate acetyltransferase, [xv] acetate kinase, [xvi] phosphoenolpyruvate carboxykinase [xvii] the proposed oxaloacetate alpha-oxo decarboxylase, [xviii] 3-hydropxypropionate dehydrogenase and [xix] malonate semialdehyde dehydrogenase FIG. 6 This figure depicts the chemical reaction performed by 2-oxo acid decarboxylases. R can be any group.
Figure 5B:
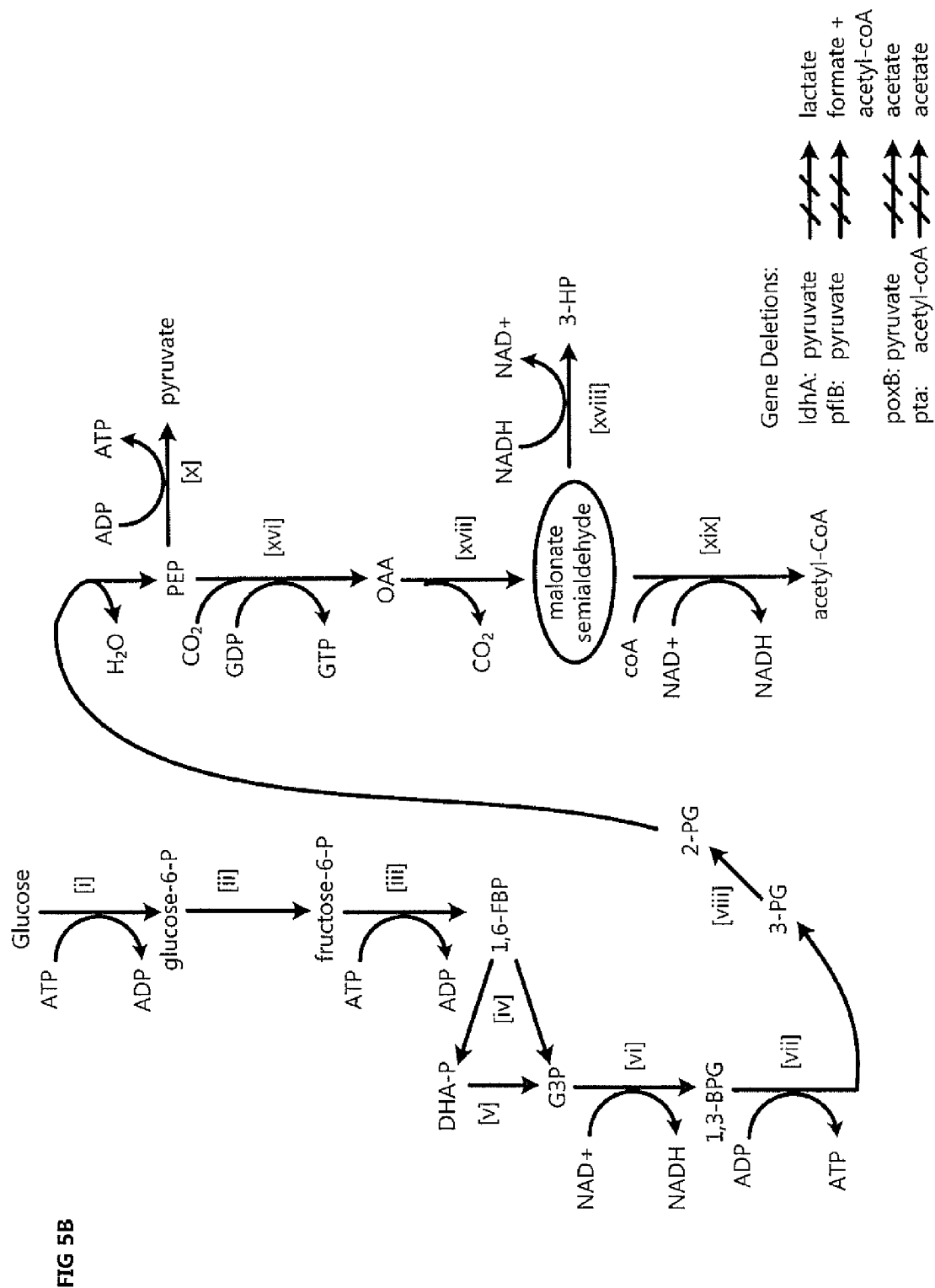

The genetic modifications conferring a 3-HP tolerant phenotype can enhance a 3-HP bio-production process utilizing E. coli. In addition, the mechanisms identified indicate that several current pathways under consideration for the production of 3-HP may not be viable routes at high levels of production In various embodiments, a bio-production pathway is utilized which uses one or more metabolic pathways not negatively affected by 3-HP. Therefore, in some embodiments one or more traditional fermentation pathways in E. coli as well as pathways involving amino acid intermediates that are currently being explored by others [9,10] are bypassed in order to enhance production. In certain embodiments, a pathway to produce 3-HP is that depicted in FIG. 5. Also, one or more gene deletions in E. coli are effectuated as well as the expression of several enzymatic functions new to E. coli. In some embodiments, the one or more gene deletions are selected genes including but not limited to gene(s) encoding pyruvate kinase (pfkA and pfkB), lactate dehydrogenase (ldhA), phosphate acetyltransferase (pta), pyruvate oxidase (poxB) and pyruvate-formate lyase (pflB) enzymes. In further embodiments, any of the one or more deletions in the preceding are combined with one or more enzyme modifications, where the enzymes include but are not limited to phosphoenolpyruvate carboxykinase (pck), malonate semialdehyde dehydrogenase A (mmsA), malonate semialdehyde dehydrogenase B (mmsB) and oxaloacetate alpha-oxo-decarboxylase (oad-2) enzymes are expressed. It should be understood that the term "deletion" in this context does not necessarily require an entire gene deletion, but rather, a modification sufficient to knock out or effectively reduce function.

The enzymatic activity (oxaloacetate alpha-oxo-decarboxylase) utilized in the proposed pathway has not been reported in the known scientific literature. The enzyme oxaloacetate alpha-oxo-decarboxylase enhances 3-HP production.

In various embodiments, a pathway having features valuable for bio-production of organic acids in general and can be viewed as a metabolic starting point for numerous other products and in various different organisms (e.g., bacteria, yeast, algae). In various embodiments, such a pathway enhancer allows intracellular production of the key intermediate acetyl-coA without the committed production of the fermentative byproduct formate normally produced in microorganisms (e.g., E. coli) with acetyl-coA under fermentative conditions.

Previously Characterized Enzymes

In various embodiments, an engineered pathway of the invention comprises several genetic modifications to wild type microorganisms (e.g., E. coli), in addition to the expression of the oxaloacetate alpha-oxo decarboxylase. For example, one or more mutations in a microorganism (e.g., E. coli) can include but not limited to genes: pykA, pykF, ldhA, pflB, pta and poxB genes. Standard methodologies can be used to generate these gene deletions and such methods are routine in the art (See, for example, Sambrook and Russell, Molecular Cloning: A Laboratory Manual, Third Edition 2001 (volumes 1-3), Cold Spring Harbor Laboratory Press, Cold Spring Harbor, N.Y., hereinafter "Sambrook and Russell").

In addition to these one or more genetic deletions, the following enzymatic activities can be expressed to enhance 3-HP production (e.g., in E. coli): phosphoenolpyruvate carboxykinase and malonate semialdehyde dehydrogenase. In a further embodiment, the mmsA gene is expressed (e.g., mmsA from Rattus norvegicus which has been shown to possess malonate semialdehyde dehydrogenase activity and converts malonate semialdehyde to acetyl-coA). In yet a further embodiment, the mmsB gene is expressed (e.g., mmsB gene from Pseudomonas aeruginosa which has been shown to have 3-hydropxypropionate dehydrogenase activity). In another further embodiment, a GDP dependant phosphoenolpyruvate carboxykinase is expressed (e.g., gene from Alcaligenes eutrophus which has been characterized with kinetics favoring the desired direction producing oxaloacetate). Any genes disclosed herein can be readily synthesized using standard methodologies.

2-oxo Acid Decarboxylases.

Figure 6:
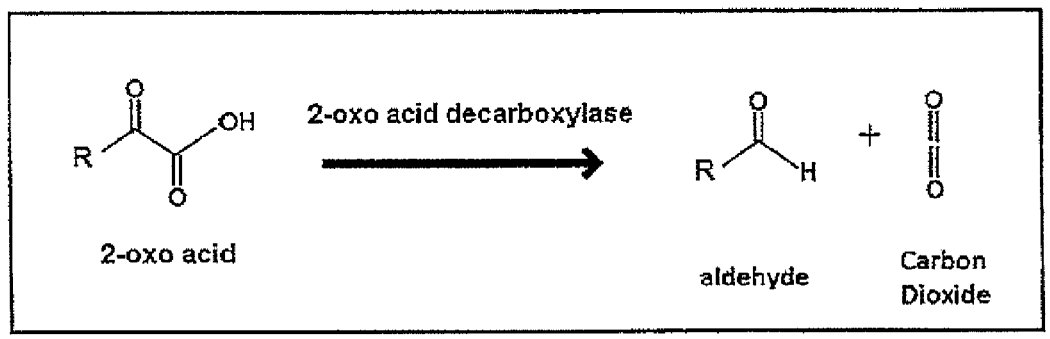
Figures 7A, 7B:
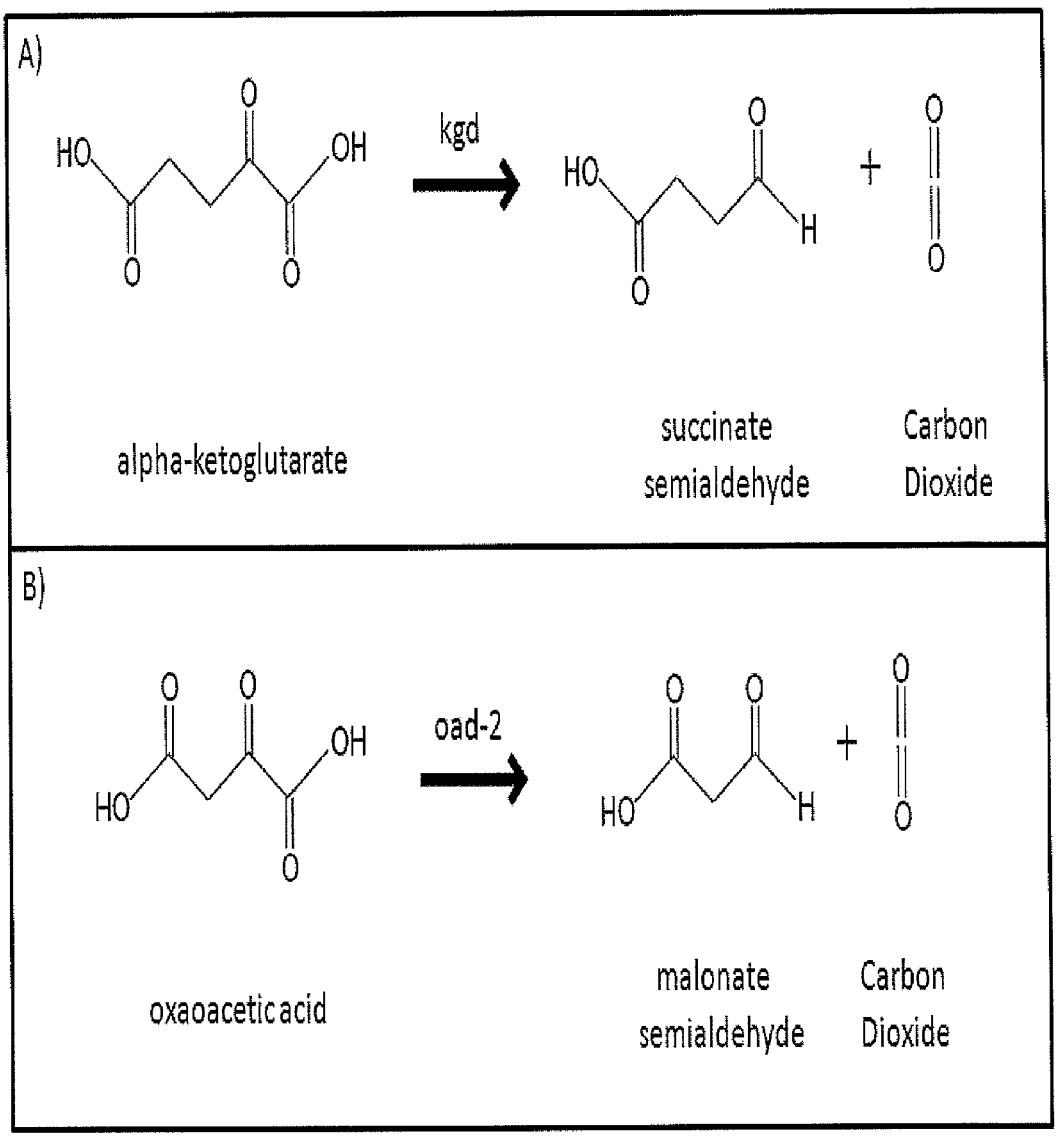
FIG. 7A This figure depicts the chemical reaction performed by alpha-ketoglutarate decarboxylase encoded by the kgd gene from *M. tuberculosis*.
FIG. 7B depicts the proposed reaction performed by the newly evolved enzyme, oxaloacetate alpha-oxo-decarboxylase. The proposed enzyme will be encoded by the oad-2 gene which will be evolved by mutation from the kgd gene.
Figure 8:
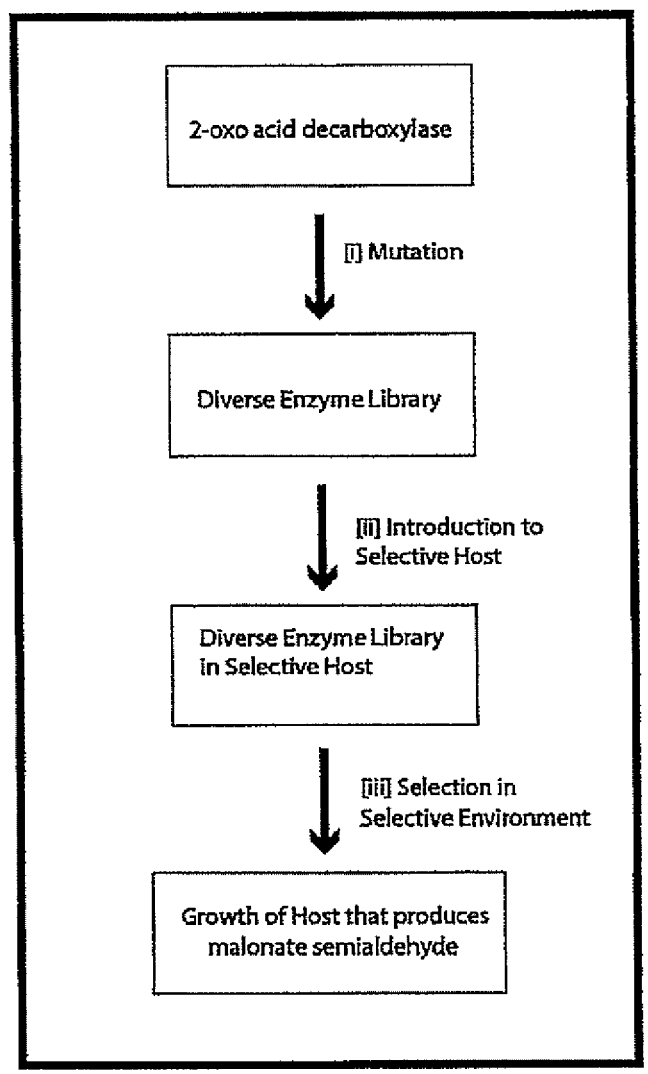
FIG. 8 This figure depicts an overview of the methods to select a diverse library of 2-oxo acid decarboxylases for oxaloacetate alpha-oxo-decarboxylase activity. [i] A natural 2-oxo acid decarboxylase is mutated to create a variant library, [ii] this library is introduced into a microbial host that will not survive in a given environment without the presence of the product of the alpha-oxo-decarboxylase, malonate semialdehyde. [iii]. Positive mutants are identified by growth under selective conditions.

Several 2-oxo decarboxylases (also referred to as 2-keto acid decarboxylases, alpha-oxo decarboxylases, or alpha-keto acid decarboxylases) with a broad substrate range have been previously characterized, including several pyruvate and branched chain 2-keto-acid decarboxylases. In various embodiments, enzymes from this class of decarboxylases are utilized. The reaction carried out by these enzymes is depicted in FIG. 6. Of additional interest is that a convenient colorimetric method has been developed to assay this enzymatic activity by detection of the products of this enzyme class which are all aldehydes. In one embodiment, a previously characterized enzyme, alpha ketoglutarate decarboxylase, encoded by the kgd gene from Mycobacterium tuberculosis is used. The enzymatic reaction performed by this enzyme is depicted in FIG. 7A, which is very similar to the desired enzymatic activity, the decarboxylation of oxaloacetate to malonate semialdehyde depicted in FIG. 7B.

Altered Enzyme Activity

In one embodiment, clones comprising enhanced oxaloacetate alpha-oxo-decarboxylase activity are obtained by mutation of a gene encoding an enzyme having a similar catalytic activity, namely 2-oxo acid decarboxylases. For example, mutant libraries of a 2-oxo acid decarboxylase gene are constructed. Oxaloacetate alpha-oxo-decarboxylase activity is selected from a mutant library of a 2-oxo acid decarboxylase genes and in one embodiment from a mutant library of the kgd gene encoding an alpha-ketoglutarate decarboxylase. In further embodiments, mutant genes encoding enzymes that modulate or enhance the desired activity are identified.

Overview

To obtain the desired altered enzyme, a mutant library of a 2-oxo acid decarboxylase gene is constructed, which will be used for selections. In various embodiments, various 2-oxo acid decarboxylase genes are cloned into an appropriate expression system for *E. coli*. Several 2-keto acid decarboxylases with a broad substrate range have been previously characterized (Pohl, M., Sprenger, G. A., Muller, M., A new perspective on thiamine catalysis. Current Opinion in Biotechnology, 15(4), 335-342 (2004)). Of particular interest is an enzyme from *M. tuberculosis*, alpha-ketoglutarate decarboxylase, kgd, which has been purified and characterized (Tian, J., Bryk, R. Itoh, M., Suematsu, M., and Carl Nathan, C. Variant tricarboxylic acid cycle in *Mycobacterium tuberculosis*: Identification of alpha-ketoglutarate decarboxylase. PNAS. Jul. 26, 2005 vol. 102(30): 10670-10677; Stephanopoulos, G., Challenges in engineering microbes for biofuels production. Science, 2007. 315(5813):801-804). Numerous 2-oxo acid decarboxylase genes are known in the art, including but limited to pyruvate decarboxylases from several sources, branched-chain 2-keto acid decarboxylases from various sources, benzylformate decarboxylases from various sources and phenylpyruvate decarboxylases from several sources (refer to www.metacyc.org for a more complete list). In one embodiment, the kgd gene, encoding and alpha-ketoglutarate decarboxylase from *M. tuberculosis* is cloned into an appropriate expression system for *E. coli*. Subsequently, this expression clone is mutated to create a library of mutant clones.

Cloning an 2-oxo Acid Decarboxylase Gene

Cloning and expression of any 2 oxo-acid decarboxylase gene including but not limited to the kgd gene is performed via gene synthesis supplied from a commercial supplier using standard or conventional techniques. Therefore, no culturing or manipulating of *M. tuberculosis* is required in the case of kgd. In addition, gene synthesis allows for codon optimization for a particular host. Once obtained using standard methodology, the gene is cloned into an expression system using standard techniques.

Construction of a 2-oxo Acid Decarboxylase Gene Library

The plasmid containing the cloned 2-oxo acid decarboxylase gene, including but not limited to the kgd gene is mutated by standard methods resulting in a large library of mutants. Generally, any of a number of well-known standard methods may be used (See, for example, chapters 1-19 of Directed Evolution Library Creation Methods and Protocols, F. H. Arnold & G. Georgiou, Eds., Methods in Molecular Biology, Vol. 231, Humana Press (2003)). The mutant sequences are introduced into a new host cell line, generating a final library for subsequent selection.

Selection of Altered Activity

Figure 9A:
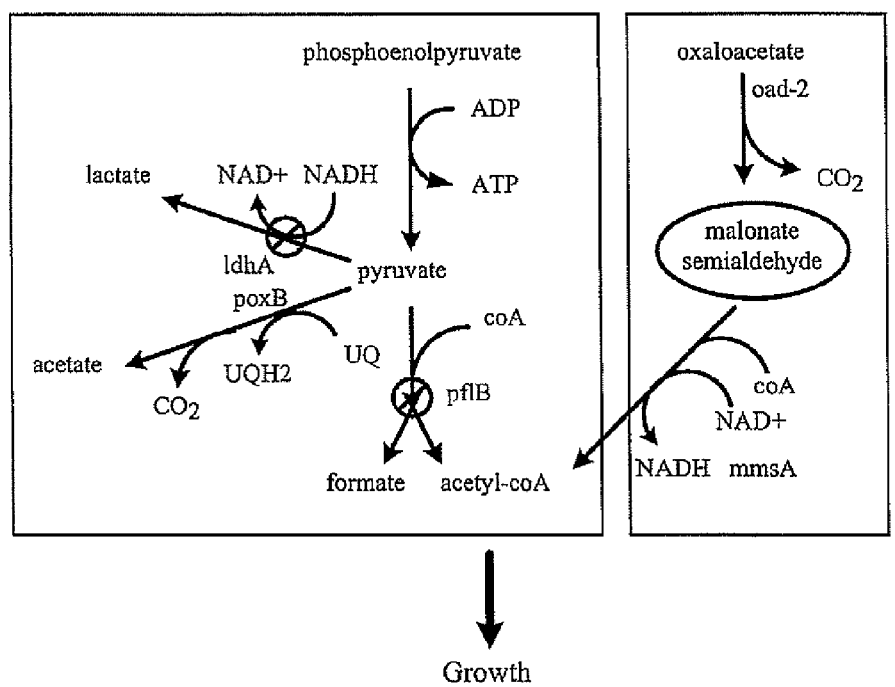
FIG. 9A depicts the proposed selection of the metabolism of *E. coli* strain NZN111 is shown in the left box. The pflB gene is disrupted blocking the formation of acetyl-coA in anaerobic conditions. The lack of acetyl-coA formation severely inhibits growth. The proposed additional enzymatic path to acetyl-coA is outlined in the right box. The characterized mmsA gene can supply acetyl-coA under anaerobic conditions if it is supplied with malonate semialdehyde by an oxaloacetate alpha-oxo decarboxylase. Kgd mutants with this activity will allow the strain to grow under anaerobic conditions.
Figure 10A:
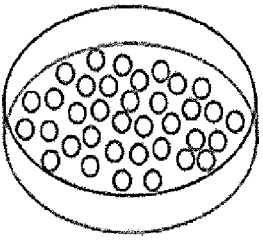
FIG. 10A depicts the anticipated Selection Results of mutant colonies expressing the desired oxaloacetate alpha-oxo-decarboxylase will grow under anaerobic conditions when expressed in *E. coli* NZN111 expressing mmsA. No growth will be observed under these conditions in the *E. coli* NZN111, *E. coli* NZN111+mmsA controls. Or in mutants not expressing the desired activity.

A selection based approach such as described herein can result in the rapid identification of a 2-oxo acid decarboxylase mutant with oxaloacetate alpha-oxo-decarboxylase activity. In one example, an available strain of *E. coli*, strain NZN111 is utilized as a host for the selection. This *E. coli* strain has deletions in both the ldhA and pflB genes resulting in severely limited growth (~10 hr doubling time) under anaerobic conditions (See right side of FIG. 5). This growth limitation is due in part to the inability to produce the necessary metabolite acetyl-coA under these conditions. (See FIG. 9A below.) A strain of *E. coli* NZN111 expressing mmsA (*E. coli* NZN111+mmsA) in addition to a mutant 2-oxo acid decarboxylase gene, including but not limited to the kgd gene, having oxaloacetate alpha-oxo-decarboxylase activity is capable of producing the metabolite acetyl-coA from the metabolic intermediate malonate semialdehyde in media supplemented with tartrate (tartate can be used as a supplement and is readily converted to oxaloacetate in *E. coli*.). This proposed strain has increased growth under anaerobic conditions when compared to both *E. coli* NZN111 and *E. coli* NZN11+ mmsA, controls. For example, such a selection is depicted in FIG. 10A. In one embodiment, *E. coli* NZN111 is constructed to express an acetylating malonate semialdehyde dehydrogenase.

Similar to the 2-oxo acid decarboxylase gene, an acetylating malonate semialdehyde dehydrogenase gene, including but not limited to mmsA, from *Pseudomonas aeruginosa* PAO1, is obtained via gene synthesis from the commercial provider. It is subsequently be cloned into an expression plasmid.

Figure 9B:
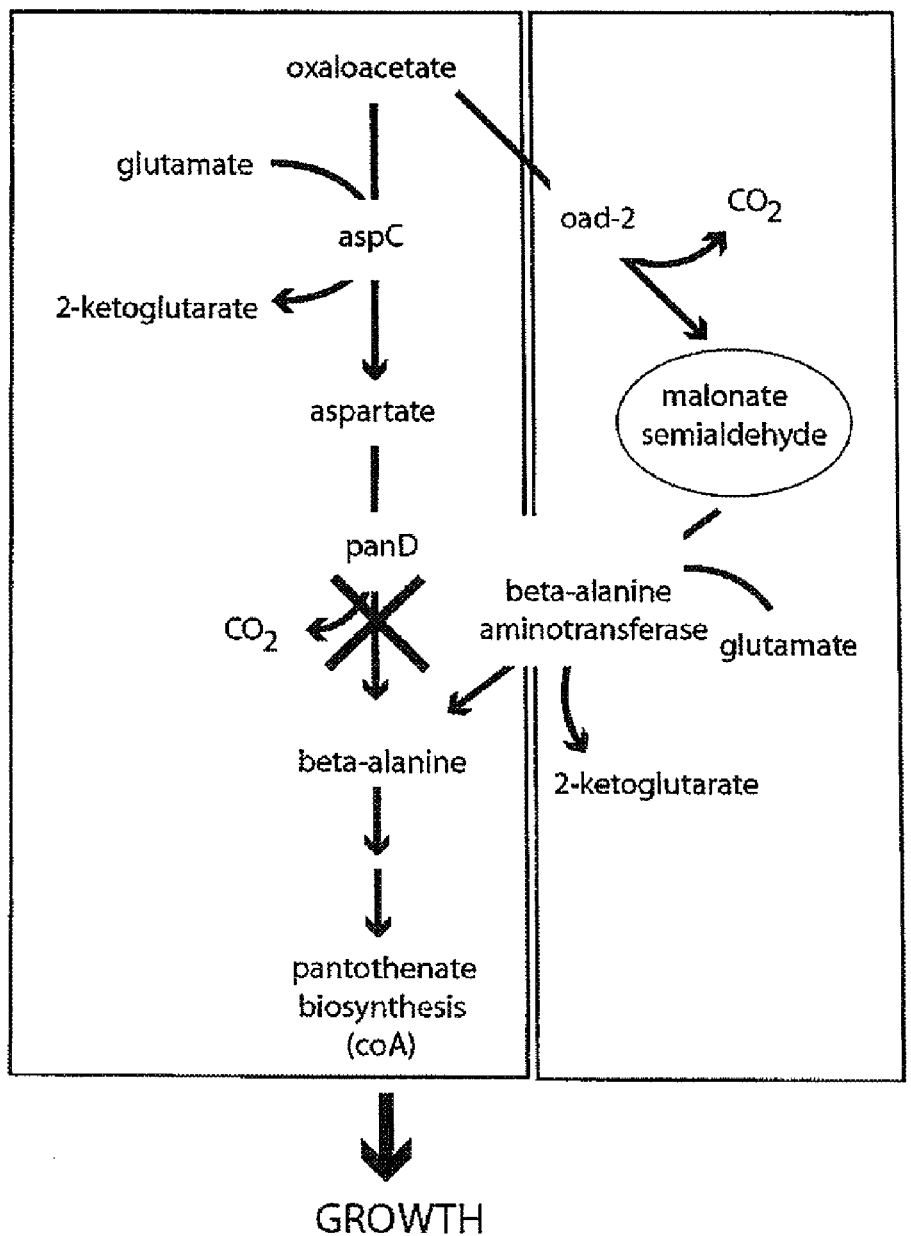
FIG. 9B depicts the proposed selection of the relevant metabolism of *E. coli* strain AB354 is summarized in the left box. The panD gene is mutated blocking the synthesis of beta-alanine, an essential precursor for pantothenate (coA). The lack of pantothenate formation abolishes growth on minimal media. The proposed additional enzymatic path to beta-alanine is outlined in the right box. The characterized *R. norvegicus* beta-alanine aminotransferase gene (gabT) can supply beta-alanine if it is supplied with malonate semialdehyde as a substrate. An active oxaloacetate alpha-decarboxylase will supply this substrate and enable growth on minimal media. Kgd mutants with this activity will allow the strain to grow on minimal media.

In another example, an available strain of *E. coli*, strain AB354 is utilized as a host for the selection. This *E. coli* strain has a mutation in the panD genes resulting in severely limited growth in minimal media conditions, without the supplementation of beta-alanine (See right side of FIG. 5). This growth limitation is due to the inability to produce beta-alanine under these conditions. (See FIG. 9B below.) A strain of *E. coli* AB354 expressing a beta alanine aminotransferase (*E. coli* AB354+beta alanine aminotransferase) in addition to a mutant 2-oxo acid decarboxylase gene, including but limited to the kgd gene, having oxaloacetate alpha-oxo-decarboxylase activity is capable of producing the metabolite beta-alanine from the metabolic intermediate malonate semialdehyde in minimal media. This proposed strain has a recovered ability to grow in minimal media with supplementation of beta-alanine. For example, such a selection is depicted in FIG. 10B. In one embodiment, *E. coli* AB354 is constructed to express a beta-alanine pyruvate aminotransferase.

Similar to the 2-oxo acid decarboxylase gene, a beta-alanine pyruvate aminotransferase gene, including but not limited to PAO132 from *Pseudomonas aeruginosa* PAO1, is obtained via gene synthesis from the commercial provider. It is subsequently be cloned into an expression plasmid.

Selection of Oxaloacetate alpha-oxo-decarboxylase Activity

The mutant library of kgd genes is introduced into *E. coli* strain NZN111 expressing the mmsA gene. This population is grown under anaerobic conditions in media supplemented with oxaloacetate. Individual mutants expressing the desired oxaloacetate alpha-oxo-decarboxylase activity show increased growth rates compared to the control strains. These clones are isolated and the mutant protein they express subsequently screened for oxaloacetate alpha-oxo-decarboxylase activity as described above.

Colorimetric Confirmation of Decarboxylase Activity

A colorimetric approach is taken from current standard methodologies. This approach necessitates the expression and purification of the mutant enzymes and reaction with the purified enzyme, its cofactor (thiamin pyrophosphate) and the appropriate substrate. Protein expression and purification are performed with standard methodologies.

The above description of an approach using NZN111 is meant to be exemplary and not limiting. Its teachings may be applied to other microorganism systems to achieve the desired results. For example, and also not meant to be limiting, use of metabolic features of another *E. coli* strain, AB354, is explained in some of the examples below.

EXAMPLES SECTION

The following examples disclose specific methods for providing an *E. coli* cell with heterologous nucleic acid sequences that encode for enzymes or other polypeptides that confer increased tolerance to 3-HP. Where there is a method to achieve a certain result that is commonly practiced in two or more specific examples (or for other reasons), that method may be provided in a separate Common Methods section that follows the examples. Each such common method is incorporated by reference into the respective specific example that so refers to it. Also, where supplier information is not complete in a particular example, additional manufacturer information may be found in a separate Summary of Suppliers section that may also include product code, catalog number, or other information. This information is intended to be incorporated in respective specific examples that refer to such supplier and/or product. In the following examples, efforts have been made to ensure accuracy with respect to numbers used (e.g., amounts, temperatures, etc.), but some experimental error and deviation should be accounted for. Unless indicated otherwise, temperature is in degrees Celsius and pressure is at or near atmospheric pressure at approximately 5340 feet (1628 meters) above sea level. It is noted that work done at external analytical and synthetic facilities was not conducted at or near atmospheric pressure at approximately 5340 feet (1628 meters) above sea level. All reagents, unless otherwise indicated, were obtained commercially.

The meaning of abbreviations is as follows: "C" means Celsius or degrees Celsius, as is clear from its usage, "s" means second(s), "min" means minute(s), "h," "hr," or "hrs" means hour(s), "psi" means pounds per square inch, "nm" means nanometers, "d" means day(s), "μL" or "uL" or "ul" means microliter(s), "mL" means milliliter(s), "L" means liter(s), "mm" means millimeter(s), "nm" means nanometers, "mM" means millimolar, "μM" or "uM" means micromolar, "M" means molar, "mmol" means millimole(s), "μmol" or "uMol" means micromole(s)", "g" means gram(s), "μg" or "ug" means microgram(s) and "ng" means nanogram(s), "PCR" means polymerase chain reaction, "OD" means optical density, "$OD_{600}$" means the optical density measured at a wavelength of 600 nm, "kDa" means kilodaltons, "g" means the gravitation constant, "bp" means base pair(s), "kbp" means kilobase pair(s), "% w/v" means weight/volume percent, % v/v" means volume/volume percent, "IPTG" means isopropyl-β-D-thiogalactopyranoiside, "RBS" means ribosome binding site, "rpm" means revolutions per minute, "HPLC" means high performance liquid chromatography, and "GC" means gas chromatography. Also, 10^5 and the like are taken to mean $10^5$ and the like.

Example 1

Development of a Plasmid Comprising kgd

The nucleic acid sequence for the alpha-ketoglutarate decarboxylase (kgd) from *M. tuberculosis* was codon optimized for *E. coli* according to a service from DNA 2.0 (Menlo Park, Calif. USA), a commercial DNA gene synthesis provider. The nucleic acid sequence was synthesized with an eight amino acid N-terminal tag to enable affinity based protein purification. This nucleic acid sequence incorporated an NcoI restriction site overlapping the gene start codon and was followed by a HindIII restriction site. In addition a Shine Delgarno sequence (i.e., a ribosomal binding site) was placed in front of the start codon preceded by an Ecor1 restriction site. This codon optimized kgd nucleic acid sequence construct (SEQ ID NO:001), which is designed to encode for the native kgd protein (SEQ ID NO:002) was synthesized by DNA 2.0 and then provided in a pJ206 vector backbone (SEQ ID NO:003).

A circular plasmid based cloning vector termed pKK223-kgd for expression of the alpha-ketoglutarate decarboxylase in *E. coli* was constructed as follows. The kgd gene in the pJ206 vector was amplified via a polymerase chain reaction with the forward primer being TTTTTTTGTATACCATGGATCGTAAATTTCGTGATGATC (SEQ ID NO:004) containing a NcoI site that incorporates the start methionine for the protein sequence, and the reverse primer being CCCGGTGAGATCTAGATCCGAACGCTTCGTCCAAGATTTCTT (SEQ ID NO:005) containing a XbaI site and a BglII site that replaces the stop codon of the kgd gene with an in-frame protein linker sequence SRS. Also, these primers effectively removed the eight amino acid N-terminal tag. The amplified kgd nucleic acid sequence was subjected to enzymatic restriction digestion with the enzymes NcoI and BglII obtained from New England BioLabs (Ipswich, Mass. USA) according to manufacturer's instructions. The digestion mixture was separated by agarose gel electrophoresis, and visualized under UV transillumination as described in Subsection II of the Common Methods Section. An agarose gel slice containing a DNA piece corresponding to the amplified kgd nucleic acid sequence was cut from the gel and the DNA recovered with a standard gel extraction protocol and components from Qiagen according to manufacturer's instructions.

An *E. coli* cloning strain bearing pKK223-3 was grown by standard methodologies and plasmid DNA was prepared by a commercial miniprep column from Qiagen.

A new DNA vector was created by amplifying a pKK223-3 template by polymerase chain reaction with a forward primer being CGGATCTAGATCTCACCATCACCACCATTAGTCGACCTGCAGCCAAG (SEQ ID NO:006) and a reverse primer being TGAGATCTAGATCCGTTATGTCCCATGGTTCTGTTTCCTGTGTG (SEQ ID NO:007). The product was prepared by a commercial PCR-purification column from Qiagen. Both primers contain XbaI restriction sites that allowed for the linear polymerase chain reaction product to be circularized after restriction digestion with XbaI with enzymes obtained from New England BioLabs (Ipswich, Mass. USA) according to manufacturer's instructions, and subsequent self-ligation. The new vector, named pKK223-ct-his (SEQ ID NO:008), contained a multiple cloning region containing the a protein coding cassette under control of a IPTG-inducible promoter with an NcoI site that incorporate the start methionine and with a XbaI site and a BglII site that code for the in-frame protein sequence SRSHHHHH (SEQ ID NO:009), a multi-histidine tag that allows for metal-affinity protein purification of the expressed protein.

To insert the gene of interest, kgd, this vector was prepared by restriction digestion with the enzymes NcoI and BglII obtained from New England BioLabs (Ipswich, Mass. USA) according to manufacturer's instructions. The digestion mixture was separated by agarose gel electrophoresis, and visualized under UV transillumination as described under Subsection II of the Common Methods Section. An agarose gel slice containing a DNA piece corresponding to the amplified kgd gene product was cut from the gel and the DNA recovered with a standard gel extraction protocol and components from Qiagen according to manufacturer's instructions.

Pieces of purified DNA corresponding to the amplified kgd gene product and the pKK223-cterm-5×his vector backbone were ligated and the ligation product was transformed and electroporated according to manufacturer's instructions. The sequence of the resulting vector, termed pKK223-cterm-5×his-kgd (SEQ ID NO:010, and simply pKK223-kgd such as in the electronic sequence listing), was confirmed by routine sequencing performed by the commercial service provided by Macrogen (USA). pKK223-cterm-5×his-kgd confers resistance to beta-lactamase and contains the kgd gene of *M. tuberculosis* under control of a ptac promoter inducible in *E. coli* hosts by IPTG.

Example 2

Development of a Plasmid Comprising mcr (Partial Prophetic)

The nucleic acid sequence for the malonyl-coA reductase gene (mcr) from *Chloroflexus auranticus* was codon optimized for *E. coli* according to a service from DNA 2.0 (Menlo Park, Calif. USA), a commercial DNA gene synthesis provider. Attached and extending beyond the ends of this codon optimized mcr nucleic acid sequence (SEQ ID NO:011) were an EcoRI restriction site before the start codon and a HindIII restriction site. In addition a Shine Delgarno sequence (i.e., a ribosomal binding site) was placed in front of the start codon preceded by an EcoRI restriction site. This gene construct was synthesized by DNA 2.0 and provided in a pJ206 vector backbone.

A circular plasmid based cloning vector termed pKK223-mcr for expression of the malonyl-CoA reductase in *E. coli* was constructed as follows. The mcr gene in the pJ206 vector was amplified via a polymerase chain reaction with the forward primer being TCGTACCAACCATGGCCGG-TACGGGTCGTTTGGCTGGTAAAATTG (SEQ ID NO:012) containing a NcoI site that incorporates the start methionine for the protein sequence, and the reverse primer being CGGTGTGAGATCTAGATCCGACGG-TAATCGCACGACCGCGGT (SEQ ID NO:013) containing a XbaI site and a BglII site that replaces the stop codon of the mcr gene with an in-frame protein linker sequence SRS. The amplified mcr nucleic acid sequence was subjected to enzymatic restriction digestion with the enzymes NcoI and XbaI obtained from New England BioLabs (Ipswich, Mass. USA) according to manufacturer's instructions. The digestion mixture was separated by agarose gel electrophoresis, and visualized under UV transillumination as described under Subsection II of the Common Methods Section. An agarose gel slice containing a DNA piece corresponding to the amplified mcr nucleic acid sequence was cut from the gel and the DNA recovered with a standard gel extraction protocol and components from Qiagen according to manufacturer's instructions.

An *E. coli* cloning strain bearing pKK223-3 was grown by standard methodologies and plasmid DNA was prepared by a commercial miniprep column from Qiagen.

As described in Example 1 above, a new DNA vector was created by amplifying a pKK223-3 template by polymerase chain reaction with a forward primer being CGGATCTA-GATCTCACCATCACCACCATTAGTCGAC-CTGCAGCCAAG (SEQ ID NO:006) and a reverse primer being TGAGATCTAGATCCGTTATGTCCCATG-GTTCTGTTTCCTGTGTG (SEQ ID NO:007). The product was prepared by a commercial PCR-purification column from Qiagen. Both primers contain XbaI restriction sites that allowed for the linear polymerase chain reaction product to be circularized after restriction digestion with XbaI and subsequent self-ligation with enzymes obtained from New England BioLabs (Ipswich, Mass. USA) according to manufacturer's instructions. The vector, named pKK223-ct-his (SEQ ID NO:008), contained a multiple cloning region containing the a protein coding cassette under control of a IPTG-inducible promoter with an NcoI site that incorporates the start methionine and with a XbaI site and a BglII site that codes for the in-frame protein sequence SRSHHHHH (SEQ ID NO:009). The latter multi-histidine sequence allows for metal-affinity protein purification of the expressed protein.

To insert the gene of interest, mcr, this vector was prepared by restriction digestion with the enzymes NcoI and XbaI obtained from New England BioLabs (Ipswich, Mass. USA) according to manufacturer's instructions. The digestion mixture was separated by agarose gel electrophoresis, and visualized under UV transillumination as described under Subsection II of the Common Methods Section.

Pieces of purified DNA corresponding to the amplified codon optimized mcr nucleic acid sequence and the pKK223-ct-his vector backbone were ligated and the ligation product was transformed and electroporated according to manufacturer's instructions. The sequence of the resulting vector termed pKK223-mcr (SEQ ID NO:014) is confirmed by routine sequencing performed by the commercial service provided by Macrogen(USA). pKK223-mcr confers resistance to beta-lactamase and contains the mcr gene of *M. tuberculosis* under control of a ptac promoter inducible in *E. coli* hosts by IPTG.

Example 3

Development of a Plasmid Comprising a Beta Alanine-Pyruvate Aminotransferase Gene. (Prophetic)

Introduction of a gene, such as the beta alanine pyruvate aminotransferase gene, into bacterial cells requires the addition of transcriptional (promoters) and translational (ribosome binding site) elements for controlled expression and production of proteins encoded by the gene. A nucleic acid sequence for a gene, whether obtained by gene synthesis or by amplification by polymerase chain reaction from genomic sources, can be ligated to nucleic acid sequences defining these transcriptional and translational elements. The present example discloses the addition of an *E. coli* minimal promoter and ribosome binding site properly oriented in the nucleic acid sequence before a gene of interest.

The beta alanine pyruvate aminotransferase gene from *Pseudomonas aeruginosa* PAO1 (locus_tag="PA0132") is amplified by polymerase chain reaction from a genomic DNA template with the forward primer being GGGTTTCCATG-GACCAGCCGCTCAACGTGG (SEQ ID NO:015) and the reverse primer being GGGTTTTCAGGCGATGCCGT-TGAGCGCTTCGCC (SEQ ID NO:016). The forward primer incorporates an NcoI restriction site at the start methionine codon of the gene and the reverse primer includes a stop codon for the gene. The amplified nucleic acid sequence is subjected to enzymatic restriction digestion with the restriction enzyme NcoI from New England BioLabs (Ipswich, Mass. USA) according to manufacturer's instructions. The digestion mixture is separated by agarose gel electrophoresis, and is visualized under UV transillumination as described under Subsection II of the Common Methods Section. An agarose gel slice containing a DNA piece corresponding to the restricted nucleic acid sequence is cut from the gel and the DNA is recovered with a standard gel extraction protocol and components from Qiagen according to manufacturer's instructions. An *E. coli* tpiA promoter and ribosome binding site is produced by polymerase chain reaction using a forward primer GGGAACGGCGGGGAAAAA-CAAACGTT (SEQ ID NO:017) and a reverse primer GGTC-CATGGTAATTCTCCACGCTTATAAGC (SEQ ID NO:018). Using genomic *E. Coli* K12 DNA as the template, a PCR reaction was conducted using these primers.

The forward primer is complimentary to the nucleic acid sequence upstream of the minimal tpiA promoter region (SEQ ID NO:019), which is the minimal promoter sequence of the *E. coli* K12 tpi gene. The reverse primer is located just downstream of the minimal promoter region and includes an NcoI restriction site at the location of the start methionine and also includes a ribosome binding site. The PCR-amplified nucleic acid sequence is subjected to enzymatic restriction digestion with the restriction enzyme NcoI from New England BioLabs (Ipswich, Mass. USA) according to manufacturer's instructions. The digestion mixture is separated by agarose gel electrophoresis, and is visualized under UV transillumination as described in Subsection II of the Common Methods Section. An agarose gel slice containing a DNA piece corresponding to the restricted nucleic acid sequence is cut from the gel and the DNA is recovered with a standard gel extraction protocol and components from Qiagen according to manufacturer's instructions. The restricted, purified nucleic acid piece containing the transcriptional and translational elements is ligated to the recovered DNA containing the gene of interest. The ligation product is used as a template for a subsequent polymerase chain reaction using the forward primer GGGAACGGCGGGGAAAAACAAACGTT (SEQ ID NO:020). Alternatively, any other forward primer may be use so long as it includes sufficient nucleic acid sequences upstream of the minimal tpiA promoter sequence (SEQ ID NO:019). In the present specific example, the reverse primer is GGGTTTTCAGGCGATGCCGTTGAGCGCTTCGCC (SEQ ID NO:021). The amplified nucleic acid product is separated by agarose gel electrophoresis, and is visualized under UV transillumination as described in Subsection II of the Common Methods Section. An agarose gel slice containing a DNA piece corresponding to the restricted nucleic acid sequence is cut from the gel and the DNA is recovered with a standard gel extraction protocol and components from Qiagen according to manufacturer's instructions.

The resulting nucleic acid piece then is ligated into a suitable plasmid or other vector or transposon or other system, for example pSMART (Lucigen Corp, Middleton, Wis., USA), StrataClone (Stratagene, La Jolla, Calif., USA) or pCR2.1-TOPO TA (Invitrogen Corp, Carlsbad, Calif., USA) according to manufacturer's instructions. These methods also are described in the Subsection II of the Common Methods Section. Accordingly, the resulting nucleic acid piece can be restriction digested and purified and re-ligated into any other vector as is standard in the art. A similar method can be used to combine any gene with any transcriptional and translational elements with variation of restriction sites and primers.

The resulting nucleic acid is cloned using standard methodologies into the multiple cloning site of plasmid pBT-3, resulting in pBT-3-BAAT. This plasmid expresses the beta-alanine aminotransferase has a replicon compatible with pKK223 based vectors and confers chloramphenicol resistance.

Example 4: Development of a plasmid comprising an acetylating malonate semialdehyde dehydrogenase (Prophetic)

Introduction of a gene, such as an acetylating malonate semialdehyde dehydrogenase gene, into bacterial cells requires the addition of transcriptional (promoters) and translational (ribosome binding site) elements for controlled expression and production of proteins encoded by the gene. A nucleic acid sequence for a gene, whether obtained by gene synthesis or by amplification by polymerase chain reaction from genomic sources, can be ligated to nucleic acid sequences defining these transcriptional and translational elements. The present example discloses the addition of an *E. coli* minimal promoter and ribosome binding site properly oriented in the nucleic acid sequence before a gene of interest.

The acetylating malonate semialdehyde dehydrogenase gene, such as is readily available from several sources (e.g., ca.expasy.org/cgi-bin/nicezyme.pl?1.2.1.18) is amplified by polymerase chain reaction from a genomic DNA template by standard PCR methodology. The forward primer incorporates an NcoI restriction site at the start methionine codon of the gene and the reverse primer includes a stop codon for the gene. The amplified nucleic acid sequence is subjected to enzymatic restriction digestion with the restriction enzyme NcoI from New England.

An *E. coli* tpiA promoter and ribosome binding site is produced by polymerase chain reaction using a forward primer GGGAACGGCGGGGAAAAACAAACGTT (SEQ ID NO:017) and a reverse primer GGTCCATGGTAAT-TCTCCACGCTTATAAGC (SEQ ID NO:018). Using genomic *E. Coli* K12 DNA as the template, a PCR reaction was conducted using these primers. The forward primer is complimentary to the nucleic acid sequence upstream of the minimal tpiA promoter region (SEQ ID NO:019). The reverse primer is located just downstream of the minimal promoter region and includes an NcoI restriction site at the location of the start methionine and also includes a ribosome binding site. The PCR-amplified nucleic acid sequence is subjected to enzymatic restriction digestion with the restriction enzyme NcoI from New England BioLabs (Ipswich, Mass. USA) according to manufacturer's instructions. The digestion mixture is separated by agarose gel electrophoresis, and is visualized under UV transillumination as described in Subsection II of the Common Methods Section. An agarose gel slice containing a DNA piece corresponding to the restricted nucleic acid sequence is cut from the gel and the DNA is recovered with a standard gel extraction protocol and components from Qiagen according to manufacturer's instructions.

The restricted, purified nucleic acid piece containing the transcriptional and translational elements is ligated to the recovered DNA containing the gene of interest. The ligation product is used as a template for a subsequent polymerase chain reaction using the forward primer GGGAACG-GCGGGGAAAAACAAACGTT (SEQ ID NO:017). Alternatively, any other forward primer may be use so long as it includes sufficient nucleic acid sequences upstream of the minimal tpiA promoter sequence (SEQ ID NO:019). In the present specific example, the reverse primer is GGGTTTTCAGGCGATGCCGTTGAGCGCTTCGCC (SEQ ID NO:021). The amplified nucleic acid product is separated by agarose gel electrophoresis, and is visualized under UV transillumination as described in Subsection II of the Common Methods Section. An agarose gel slice containing a DNA piece corresponding to the restricted nucleic acid sequence is cut from the gel and the DNA is recovered with a standard gel extraction protocol and components from Qiagen according to manufacturer's instructions.

The resulting nucleic acid piece then is ligated into a suitable plasmid or other vector or transposon or other system, for example pSMART (Lucigen Corp, Middleton, Wis., USA), StrataClone (Stratagene, La Jolla, Calif., USA) or pCR2.1-TOPO TA (Invitrogen Corp, Carlsbad, Calif., USA) according to manufacturer's instructions. These methods also are described in the Subsection II of the Common Methods Section. Accordingly, the resulting nucleic acid piece can be restriction digested and purified and re-ligated into any other vector as is standard in the art. A similar method can be used to combine any gene with any transcriptional and translational elements with variation of restriction sites and primers.

The resulting nucleic acid is cloned using standard methodologies into the multiple cloning site of plasmid pBT-3, resulting in pBT-3-mmsA. This plasmid expresses an acetylating malonate semialdehyde dehydrogenase has a replicon compatible with pKK223 based vectors and confers chloramphenicol resistance.

Example 5

Development of a Plasmid Comprising a Pyruvate Decarboxylase. Evolution of Pyruvate Decarboxylase Enzymes for the Enzymatic Conversion of Oxaloacetate to Malonate Semialdehyde (Prophetic)

Similarly to alpha-ketoglutarate dehydrogenase from *Mycobacterium tuberculosis*, the pyruvate decarboxylase from *Zymomonas mobilis* can be evolved to perform the conversion of oxaloacetate to malonate semialdehyde. The pyruvate decarboxylase enzyme is a thiamine diphosphate-dependent enzyme that decarboxylates 2-keto acids and has been shown to prefer short aliphatic substrates (Siegert P et al. (2005). Exchanging the substrate specificities of pyruvate decarboxylase from *Zymomonas mobilis* and benzoylformate decarboxylase from *Pseudomonas putida*. Protein Eng Des Sel 18, 345-357). Additionally, this enzyme does not require substrate activation by pyruvamide (Hoppner, T. C. & Doelle, H. W. (1983). Purification and kinetic characteristics of pyruvate decarboxylase and ethanol dehydrogenase from *Zymomonas mobilis* in relation to ethanol production. Eur J Appl Microbiol Biotechnol 17, 152-157), and a structure of the protein characterized by x-ray crystallography shows the residues responsible for formation of the substrate and cofactor binding pockets (Dobritzsch D et al. (1998). High resolution crystal structure of pyruvate decarboxylase from *Zymomonas mobilis*. Implications for substrate activation in pyruvate decarboxylases. J Biol Chem 273, 20196-20204). Furthermore, alteration of the substrate specificity of this enzyme by specific amino acid changes have previously been reported (Siegert P et al. (2005). Exchanging the substrate specificities of pyruvate decarboxylase from *Zymomonas mobilis* and benzoylformate decarboxylase from *Pseudomonas putida*. Protein Eng Des Sel 18, 345-357). An example of a process for randomly mutating specific amino acid regions of this protein follows.

To evolve the binding pocket of the protein for performing the oxaloacetate to malonate semialdehyde conversion, specific regions of the nucleic acid sequence comprising regions of the protein's amino acid sequence will be mutated. Identification of specific amino acid regions within the protein that are involved in the binding pocket interactions is performed by examining the previously determined crystal structure and also by comparing the protein sequence of the *Zymomonas mobilis* pyruvate decarboxylase with pyruvate decarboxylase from other species showing strong sequence similarity. Using this information, the nucleotide sequence of the gene is examined in order to place restriction sites within the nucleotide sequence at the boundaries of the corresponding amino acid regions identified previously. Form this nucleotide sequence, the *Zymomonas mobilis* pyruvate decarboxylase gene with these restrictions sites is codon optimized for *E. coli* according to a service from DNA 2.0 (Menlo Park, Calif. USA), a commercial DNA gene synthesis provider (SEQ ID NO:022). This gene construct is synthesized by DNA 2.0 and provided in a pJ206 vector backbone. Additionally, the protein sequence includes the addition of a hepta-histidine purification tag (SEQ ID NO:009), which can be easily removed by restriction digestion of the plasmid with HindIII followed by self-ligation. The protein for which SEQ ID NO:022 encodes is provided as SEQ ID NO:023.

To specifically mutate amino acids in the pyruvate decarboxylase protein, the plasmid containing the codon-optimized sequence is cut at regions of interest via the incorporated restriction sites. Nucleotide sequences is synthesized or produced by polymerase chain reaction with oligonucleotides designed to incorporate specific or random changes at these regions of interest.

Figure 11:
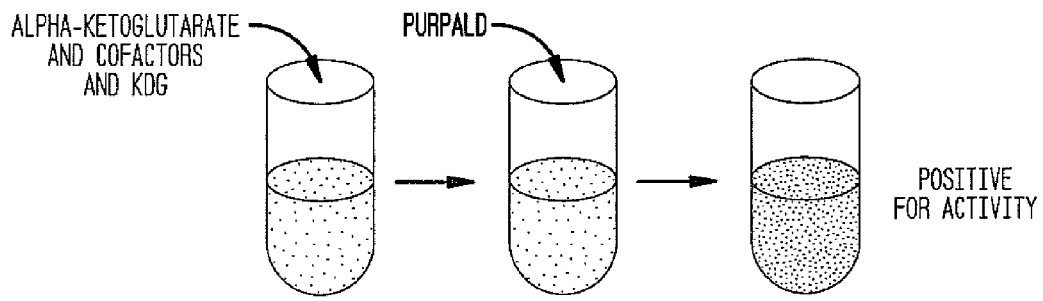
FIG. 11 depicts the screening Protocol. Purified enzyme will be mixed in vitro with the appropriate substrate and reagents. A) The control reaction for the native alpha-ketoglutarate decarboxylase. B) Predicted results for the native alpha-ketoglutarate decarboxylase with oxaloacetate as a substrate. C) Predicted results for kgd mutants, both positive and negative, for oxaloacetate alpha-decarboxylase activity.
Figure 11:
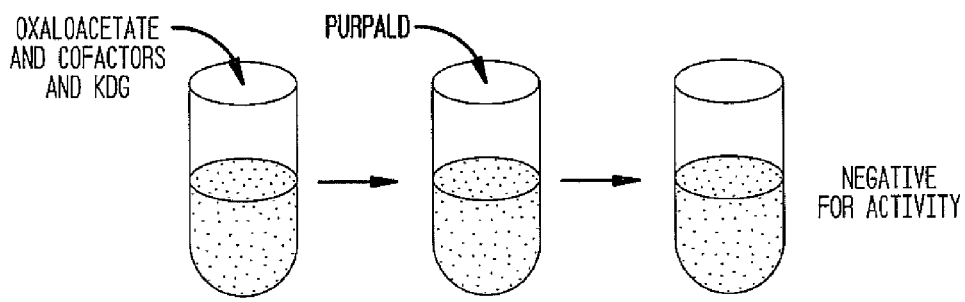
Figure 11:
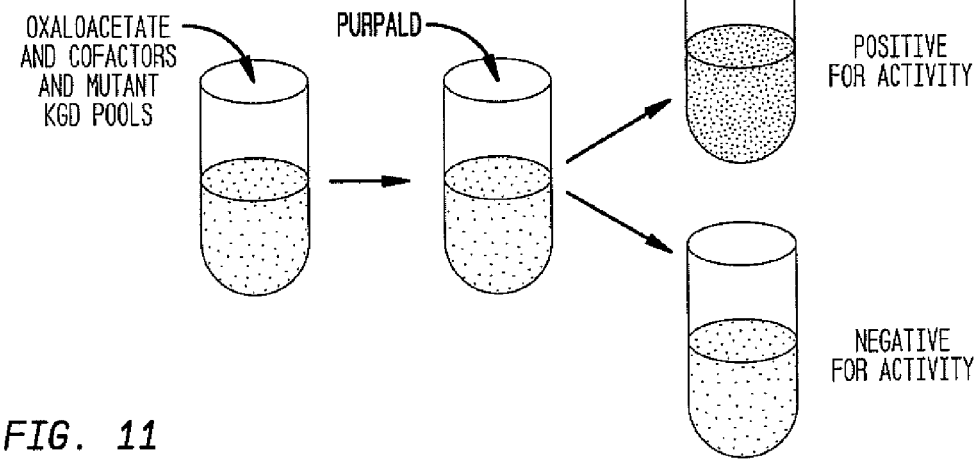

These nucleotide sequences will incorporate restriction sites or overhanging ends complimentary to the restriction sites used to cut the plasmid such that the new sequences are ligated into the plasmid to create the desired changes in the protein. These changes can be performed singly or multiply. If these changes are performed multiply, the resulting plasmids are transformed into a panD deleted *E. coli* strain and screened in a manner such as depicted in FIGS. 10A and 10B. Additionally, the protein produced by these changes may be assayed in a manner such as depicted in FIG. 11.

Example 6

Development of a Nucleic Acid Sequence Encoding a Protein Sequence Demonstrating Elevated Oxaloacetate Alpha-Decarboxylase Activity (Partial Prophetic)

Figure 12:
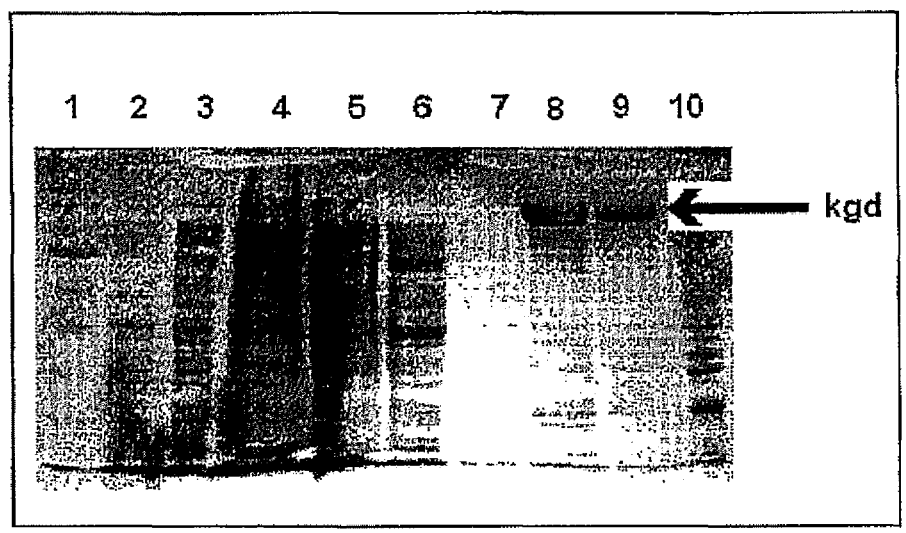
FIG. 12 Expression and Purification results of pKK223-Cterm-5×His-kgd. Lane 1=marker; lane 2=uninduced culture; lane 3=induced culture; lane 4=native lysate; lane 5=flowthrough; lane 6=first wash (wash 1); lane 7=last wash (wash 3); lane 8=first elution; lane 9=second elution, purified kg; lane 10=pelleted cell debris. The arrow points to the band comprising purified alpha-ketoglutarate decarboxylase.

Oxaloacetate alpha-decarboxylase activity is selected from a pool of alpha-ketoglutarate decarboxylase (kgd) mutants by selection in an *E. coli* AB354 host expressing a beta-alanine pyruvate aminotransferase. pKK223-cterm-5×his-kgd encoding the kgd gene was constructed as described above. Confirmation of alpha-ketoglutarate decarboxylase protein expression and enzymatic activity with appropriate controls were as follows. E. Cloni 10GF' electrocompetent cells (Lucigen, Cat. #60061-1) were transformed with the pKK223-Cterm-5×His-kgd, plasmid containing sequence for 5× HIS-tagged kgd protein behind a pTAC promoter. Transformants were confirmed using restriction digest and DNA sequencing (Macrogen, Korea). Expression and purification of his-tagged-kgd was performed as described in Subsection III of the Common Methods Section. SDS-PAGE results of expression and purification are show in FIG. 12. *E. coli* AB354 (ΔpanD) was transformed with the vector controls, pKK223, pKK223-Cterm-5×His, as well as the test vectors pKK223-mcr and pKK223-Cterm-5×His-kgd, according to standard methods described below. Each of the strains was grown overnight in LB rich media supplemented with 200 mg/L ampicillin (according to standard protocols). Following overnight growth, cells twice were harvested by centrifugation and washed by resuspension in M9 minimal media (standard protocol), diluted 1:10,000 and plated on M9 minimal media plates with 0.05 g/L threonine, 0.1 g/L leucine, 0.067 g/L thiamine, with the additional appropriate supplements, where indicated at the following concentrations (10 g/L beta-alanine (Sigma Aldrich, St. Louis, Mo.), 1 mM Isopropyl β-D-1-thiogalactopyranoside (Thermo Fisher Scientific, Fairlawn, N.J.), 0.2 g/L putrescine (MPBiomedicals, Santa Ana, Calif.), 200 mg/L ampicillin (Research Products International Corp., Mt. Prospect, Ill.) After plating, agarose plates were incubated at 37 C overnight by standard methods. Table 1 depicts the results of these selection controls. A plus (+) indicates growth on a plate, minus (−) indicates no growth. These data confirm the absence of growth in the selection hosts. Putrescine is known to induce the expression of gamma-aminobutyrate transaminase in *E. coli*. This enzyme has been shown in some species including *Rattus norvegicus* to also have beta-alanine aminotransferase activity. The mcr gene encoding the malonyl-coA reductase, has been shown to produce malonate semialdehyde. The lack of growth on the strain expressing malonyl-coA reductase in the presence of putrescine indicates the need for the co-expression of a beta-alanine aminotransferase in *E. coli* AB354 for the selection.

TABLE 1

| Strain | Supplements | | | | | | |
|---|---|---|---|---|---|---|---|
| | None | β-ala-nine | Amp | Amp + β-ala-nine | IPTG + Amp | AMP + Put | Amp + IPTG + Put |
| K12 | + | + | − | − | − | − | − |
| AB354 (Δ panD) | − | + | − | − | − | − | − |
| AB354 (Δ panD) + pKK223 | − | + | − | + | − | − | − |
| AB354 (Δ panD) + pKK223-mcr | − | + | − | + | − | − | − |
| AB354 (Δ panD) + pKK223-kgd | − | + | − | + | − | − | − |

Mutant libraries of pKK223-cterm-5×his-kgd were constructed as follows. Plasmid DNA of pKK223-cterm-5×his-kgd was purified by standard methods and transformed in the mutator strain *E. coli* XL1-Red (Stratagene, La Jolla, Calif.) according to manufacturer's protocols. Cells were harvested according to manufacturer's protocols and mutated plasmid DNA purified by standard methods.

Mutant pKK223-cterm-5×his-kgd DNA is used to transform an *E. coli* host, AB354+pBT-3-BAAT, described above. Greater than 10^5 transformants are collected from LB ampicillin (200 g/L), Chloramphenicol (40 g/L) agarose plates. Cells are washed in M9 minimal media, diluted 1:10,000 and plated on M9 minimal media plates with 0.05 g/L threonine, 0.1 g/L leucine, 0.067 g/L thiamine, with 1 mM Isopropyl β-D-1-thiogalactopyranoside (Thermo Fisher Scientific, Fairlawn, N.J.), 200 g/L ampicillin and 40 g/L chloramphenicol. Plates are incubated at 37 C for several days. Colonies that grow are individually collected as positives clones bearing oxaloacetate alpha-decarboxylase activity.

Example 7

Development of a Nucleic Acid Sequence Encoding a Protein Sequence Demonstrating Elevated Oxaloacetate Alpha-Decarboxylase Activity (Prophetic)

Oxaloacetate alpha-decarboxylase activity is selected from a pool of pyruvate decarboxylase (pdc) mutants by selection in an *E. coli* AB354 host expressing a beta-alanine pyruvate aminotransferase. pKK223-cterm-5×his-pdc encoding the pdc gene is constructed as described above. Confirmation of pyruvate decarboxylase protein expression and enzymatic activity with appropriate controls are as follows. E. Cloni 10GF' electrocompetent cells (Lucigen, Cat. #60061-1) are transformed with the pKK223-Cterm-5×His-pdc, plasmid containing sequence for 5× HIS-tagged pdc protein behind a pTAC promoter. Transformants are confirmed using restriction digest and DNA sequencing (Macrogen, Korea). Expression and purification of his-tagged-pdc are performed as described in Subsection III of the Common Methods Section. *E. coli* AB354 (ΔpanD) is transformed with the vector controls, pKK223, pKK223-Cterm-5×His, as well as the test vectors pKK223-mcr and pKK223-Cterm-5×His-pdc, according to standard methods described below. Each of the strains is grown overnight in LB rich media supplemented with 200 mg/L ampicillin (according to standard protocols). Following overnight growth, cells twice are harvested by centrifugation and washed by resuspension in M9 minimal media (standard protocol), diluted 1:10,000 and plated on M9 minimal media plates with 0.05 g/L threonine, 0.1 g/L leucine, 0.067 g/L thiamine, with the additional appropriate supplements, where indicated at the following concentrations (10 g/L beta-alanine (Sigma Aldrich, St. Louis, Mo.), 1 mM Isopropyl β-D-1-thiogalactopyranoside (Thermo Fisher Scientific, Fairlawn, N.J.), 0.2 g/L putrescine (MPBiomedicals, Santa Ana, Calif.), 200mg/L ampicillin (Research Products International Corp., Mt. Prospect, Ill.) After plating, agarose plates were incubated at 37 C overnight by standard methods. Putrescine is known to induce the expression of gamma-aminobutyrate transaminase in *E. coli*. This enzyme has been shown in some species including *Rattus norvegicus* to also have beta-alanine aminotransferase activity. The mcr gene encoding the malonyl-coA reductase, has been shown to produce malonate semialdehyde. The lack of growth on the strain expressing malonyl-coA reductase in the presence of putrescine indicates the need for the co-expression of a beta-alanine aminotransferase in *E. coli* AB354 for the selection.

Mutant libraries of pKK223-cterm-5×his-pdc are constructed as follows. Plasmid DNA of pKK223-cterm-5×his-pdc are purified by standard methods and transformed in the mutator strain *E. coli* XL1-Red (Stratagene, La Jolla, Calif.) according to manufacturer's protocols. Cells are harvested according to manufacturer's protocols and mutated plasmid DNA purified by standard methods.

Mutant pKK223-cterm-5×his-pdc DNA is used to transform an *E. coli* host, AB354+pBT-3-BAAT, described above. Greater than 10^5 transformants are collected from LB ampicillin (200 g/L), Chloramphenicol (40 g/L) agarose plates. Cells are washed in M9 minimal media, diluted 1:10,000 and plated on M9 minimal media plates with 0.05 g/L threonine, 0.1 g/L leucine, 0.067 g/L thiamine, with 1 mM Isopropyl β-D-1-thiogalactopyranoside (Thermo Fisher Scientific, Fairlawn, N.J.), 200 g/L ampicillin and 40 g/L chloramphenicol. Plates are incubated at 37 C for several days. Colonies that grow are individually collected as positives clones bearing oxaloacetate alpha-decarboxylase activity.

Example 8

Development of a Nucleic Acid Sequence Encoding a Protein Sequence Demonstrating Elevated Oxaloacetate Alpha-Decarboxylase Activity (Partial Prophetic)

Oxaloacetate alpha-decarboxylase activity is selected from a pool of alpha-ketoglutarate decarboxylase (kgd) mutants by selection in an *E. coli* NZN111 host expressing an acetylating malonate semialdehyde dehydrogenase. pKK223-cterm-5×his-kgd encoding the kgd gene was constructed as described above. Confirmation of alpha-ketoglutarate decarboxylase protein expression and enzymatic activity with appropriate controls were as follows. E. Cloni 10GF' electrocompetent cells (Lucigen, Cat. #60061-1) were transformed with the pKK223-Cterm-5×His-kgd, plasmid containing sequence for 5× HIS-tagged kgd protein behind a pTAC promoter. Transformants were confirmed using restriction digest and DNA sequencing (Macrogen, Korea). Expression and purification of his-tagged-kgd were performed as described in Subsection III of the Common Methods Section.

E. coli NZN111 is transformed with the vector controls, pKK223, pKK223-Cterm-5×His, as well as the test vectors pKK223-mcr and pKK223-Cterm-5×His-kgd, according to standard methods described below. Each of the strains is grown overnight in LB rich media supplemented with 200 mg/L ampicillin (according to standard protocols). Following overnight growth, cells twice are harvested by centrifugation and washed by resuspension in LB media (standard protocol), diluted 1:10,000 and plated on LB media plates with the additional appropriate supplements, where indicated at the following concentrations 1 mM Isopropyl β-D-1-thiogalactopyranoside (Thermo Fisher Scientific, Fairlawn, N.J.), 200mg/L ampicillin (Research Products International Corp., Mt. Prospect, Ill.) After plating, agarose plates are incubated at 37 C overnight anaerobically in BD type A Bio-Bags according to manufacturer's instructions (BD Biosciences, Franklin Lakes, N.J., Catalog #261214). The mcr gene encoding the malonyl-coA reductase, has been shown to produce malonate semialdehyde. The presence of growth of the strain expressing malonyl-coA reductase in the presence of the co expressed acetylating malonate semialdehyde dehydrogenase in E. coli NZN111 serves as a positive control for the selection.

Mutant libraries of pKK223-cterm-5×his-kgd were constructed as follows. Plasmid DNA of pKK223-cterm-5×his-kgd were purified by standard methods and transformed into the mutator strain E. coli XL1-Red (Stratagene, La Jolla, Calif.) according to manufacturer's protocols. Cells were harvested according to manufacturer's protocols and mutated plasmid DNA purified by standard methods.

Mutant pKK223-cterm-5×his-kgd DNA is used to transform an E. coli host, NZN111+pBT-3-mmsA, described above. Greater than 10^5 transformants are collected from LB ampicillin (200 g/L), Chloramphenicol (40 g/L) agarose plates. Cells are washed in LB media, diluted 1:10,000 and plated on LB media plates with 1 mM Isopropyl β-D-1-thiogalactopyranoside (Thermo Fisher Scientific, Fairlawn, N.J.), 200 g/L ampicillin and 40 g/L chloramphenicol. Plates are incubated at 37 C for several days anaerobically in BD type A Bio-Bags according to manufacturer's instructions (BD Biosciences, Franklin Lakes, N.J., Catalog #261214). Colonies that grow are individually collected as positives clones bearing oxaloacetate alpha-decarboxylase activity.

Example 9

Development of a Nucleic Acid Sequence Encoding a Protein Sequence Demonstrating Elevated Oxaloacetate Alpha-Decarboxylase Activity (Prophetic)

Oxaloacetate alpha-decarboxylase activity is selected from a pool of pyruvate decarboxylase (pdc) mutants by selection in an E. coli NZN111 host expressing an acetylating malonate semialdehyde dehydrogenase. pKK223-cterm-5×his-pdc encoding the pdc gene is constructed as described above. Confirmation of pyruvate decarboxylase protein expression and enzymatic activity with appropriate controls are as follows. E. Cloni 10GF' electrocompetent cells (Lucigen, Cat. #60061-1) are transformed with the pKK223-Cterm-5×His-pdc, plasmid containing sequence for 5× HIS-tagged pdc protein behind a pTAC promoter. Transformants are confirmed using restriction digest and DNA sequencing (Macrogen, Korea). Expression and purification of his-tagged-pdc are performed as described in Subsection III of the Common Methods Section.

E. coli NZN111 and E. coli NZN111+pBT3-mmsA is transformed with the vector controls, pKK223, pKK223-Cterm-5×His, as well as the test vectors pKK223-mcr and pKK223-Cterm-5×His-pdc, according to standard methods described below. Each of the strains is grown overnight in LB rich media supplemented with 200 mg/L ampicillin (according to standard protocols). Following overnight growth, cells twice are harvested by centrifugation and washed by resuspension in LB media (standard protocol), diluted 1:10,000 and plated on LB media plates with the additional appropriate supplements, where indicated at the following concentrations 1 mM Isopropyl β-D-1-thiogalactopyranoside (Thermo Fisher Scientific, Fairlawn, N.J.), 200 mg/L ampicillin (Research Products International Corp., Mt. Prospect, Ill.) After plating, agarose plates were incubated at 37 C overnight anaerobically in BD type A Bio-Bags according to manufacturer's instructions (BD Biosciences, Franklin Lakes, N.J., Catalog #261214). The mcr gene encoding the malonyl-coA reductase, has been shown to produce malonate semialdehyde. The presence of growth of the strain expressing malonyl-coA reductase in the presence of the co-expressed acetylating malonate semialdehyde in E. coli NZN111 serves as a positive control for the selection.

Mutant libraries of pKK223-cterm-5×his-pdc are constructed as follows. Plasmid DNA of pKK223-cterm-5×his-pdc are purified by standard methods and transformed into the mutator strain E. coli XL1-Red (Stratagene, La Jolla, Calif.) according to manufacturer's protocols. Cells are harvested according to manufacturer's protocols and mutated plasmid DNA purified by standard methods.

Mutant pKK223-cterm-5×his-pdc DNA is used to transform an E. coli host, NZN111+pBT-3-mmsA, described above. Greater than 10^5 transformants are collected from LB ampicillin (200 g/L), chloramphenicol (40 g/L) agarose plates. Cells are washed in LB media, diluted 1:10,000 and plated on LB media plates with 1 mM Isopropyl β-D-1-thiogalactopyranoside (Thermo Fisher Scientific, Fairlawn, N.J.), 200 g/L ampicillin and 40 g/L chloramphenicol. Plates are incubated at 37 C for several days anaerobically in BD type A Bio-Bags according to manufacturer's instructions (BD Biosciences, Franklin Lakes, N.J., Catalog #261214). Colonies that grow are individually collected as positives clones bearing oxaloacetate alpha-decarboxylase activity.

Example 10

Confirmation of Oxaloacetate Alpha-Decarboxylase Activity (Partial Prophetic)

The colorimetric to confirm enzymatic decarboxylation of 2-oxo-acid substrates is adapted from current standard methodologies and is illustrated below in FIG. 11. This approach necessitates the expression and purification of the mutant enzymes and reaction with the purified enzyme, its cofactor (thiamin pyrophosphate) and the appropriate substrate. Protein expression and purification are performed with standard methodologies. This colorimetric screening method will be used both to conduct broad screening for positive oxaloacetate alpha-decarboxylase mutants, and also to conduct confirmatory testing of the positive clones identified in a selection method described above.

Transformants containing a gene cloned into the pKK223-Cterm-5×his expression vector are grown overnight in LB+0.2% glucose+200 ug/mL Ampicillin, diluted 1:20 and grown (LB+0.2% glucose+200 ug/mL Ampicillin) to OD600 of 0.4. IPTG is added at 1 mM final concentration to induce protein expression. Cultures are then allowed to grow at 37 degrees C. for four hours. Cells were harvested by centrifugation at 4 degrees C. for 10 minutes at 4000 rpm. Pellets are resuspended and concentrated 50× (e.g. 500 mL culture resuspended in 10 mL buffer) in Qiagen Ni-NTA Lysis Buffer (50 mM Na2HPO4, 300 mM NaCl, 10 mM imidazole, pH 8.0)+1 mM PMSF. Lysozyme is added to a final concentration of 1 mg/mL; cells are incubated on ice for 30 minutes. Cells are lysed using a French Press (cell pressure=2000 psi) three times. Lysates are cleared by centrifugation at 4 degrees C. for 20 minutes, applied to Qiagen Ni-NTA columns, washed and eluted as specified by Qiagen (cat. #31314). Samples are analyzed by SDS-PAGE by routine protocols.

100 uL reaction mixtures contain 50 mM Potassium phosphate (pH 7.0), 0.2 mM TPP, 1 mM $MgCl_2$, 10 mM of the appropriate substrate. 300 pg of purified enzyme is added to the reaction and incubated 16 hours at 37 degrees C. After 16 hours at 37 degrees C., 100 uL of Purpald colorimetric indicator (as per Sigma-Aldrich, cat. #162892) is added to each well in order to detect formation of corresponding aldehyde product. After addition of the Purpald, reactions are incubated at room temperature for 1 hour and read at a wavelength of 540 nm in a Thermomax Microplate Reader (Molecular Devices) using SOFTMax Pro Microplate Reader software, Ver. 4.0. Absorbances greater than control reactions without substrate are used to determine the presence of decarboxylation.

Common Methods Section

All methods in this Section are provided for incorporation into the above methods where so referenced therein and/or below.

Subsection I. Bacterial Growth Methods: Bacterial growth culture methods, and associated materials and conditions, are disclosed for respective species that may be utilized as needed, as follows:

*Escherichia coli* K12 is a gift from the Gill lab (University of Colorado at Boulder) and is obtained as an actively growing culture. Serial dilutions of the actively growing *E. coli* K12 culture are made into Luria Broth (RPI Corp, Mt. Prospect, Ill., USA) and are allowed to grow for aerobically for 24 hours at 37° C. at 250 rpm until saturated.

*Pseudomonas aeruginosa* genomic DNA is a gift from the Gill lab (University of Colorado at Boulder).

Subsection II: Gel Preparation, DNA Separation, Extraction, Ligation, and Transformation Methods:

Molecular biology grade agarose (RPI Corp, Mt. Prospect, Ill., USA) is added to 1× TAE to make a 1% Agarose: TAE solution. To obtain 50× TAE add the following to 900 mL of distilled water: add the following to 900 ml distilled $H_2O$: 242 g Tris base (RPI Corp, Mt. Prospect, Ill., USA), 57.1 ml Glacial Acetic Acid (Sigma-Aldrich, St. Louis, Mo., USA) and 18.6 g EDTA (Fisher Scientific, Pittsburgh, Pa. USA) and adjust volume to 1L with additional distilled water. To obtain 1× TAE, add 20 mL of 50× TAE to 980 mL of distilled water. The agarose-TAE solution is then heated until boiling occurred and the agarose is fully dissolved. The solution is allowed to cool to 50° C. before 10 mg/mL ethidium bromide (Acros Organics, Morris Plains, N.J., USA) is added at a concentration of 5 ul per 100 mL of 1% agarose solution. Once the ethidium bromide is added, the solution is briefly mixed and poured into a gel casting tray with the appropriate number of combs (Idea Scientific Co., Minneapolis, Minn., USA) per sample analysis. DNA samples are then mixed accordingly with 5× TAE loading buffer. 5× TAE loading buffer consists of 5× TAE (diluted from 50× TAE as described above), 20% glycerol (Acros Organics, Morris Plains, N.J., USA), 0.125% Bromophenol Blue (Alfa Aesar, Ward Hill, Mass., USA), and adjust volume to 50 mL with distilled water. Loaded gels are then run in gel rigs (Idea Scientific Co., Minneapolis, Minn., USA) filled with 1× TAE at a constant voltage of 125 volts for 25-30 minutes. At this point, the gels are removed from the gel boxes with voltage and visualized under a UV transilluminator (FOTODYNE Inc., Hartland, Wis., USA).

The DNA isolated through gel extraction is then extracted using the QIAquick Gel Extraction Kit following manufacturer's instructions (Qiagen (Valencia Calif. USA)). Similar methods are known to those skilled in the art.

The thus-extracted DNA then may be ligated into pSMART (Lucigen Corp, Middleton, Wis., USA), StrataClone (Stratagene, La Jolla, Calif., USA) or pCR2.1-TOPO TA (Invitrogen Corp, Carlsbad, Calif., USA) according to manufacturer's instructions. These methods are described in the next subsection of Common Methods.

Ligation Methods:

For Ligations into pSMART Vectors:

Gel extracted DNA is blunted using PCRTerminator (Lucigen Corp, Middleton, Wis., USA) according to manufacturer's instructions. Then 500 ng of DNA is added to 2.5 uL 4× CloneSmart vector premix, 1 ul CloneSmart DNA ligase (Lucigen Corp, Middleton, Wis., USA) and distilled water is added for a total volume of 10 ul. The reaction is then allowed to sit at room temperature for 30 minutes and then heat inactivated at 70° C. for 15 minutes and then placed on ice. E. cloni 10G Chemically Competent cells (Lucigen Corp, Middleton, Wis., USA) are thawed for 20 minutes on ice. 40 ul of chemically competent cells are placed into a microcentrifuge tube and 1 ul of heat inactivated CloneSmart Ligation is added to the tube. The whole reaction is stirred briefly with a pipette tip. The ligation and cells are incubated on ice for 30 minutes and then the cells are heat shocked for 45 seconds at 42° C. and then put back onto ice for 2 minutes. 960 ul of room temperature Recovery media (Lucigen Corp, Middleton, Wis., USA) and places into microcentrifuge tubes. Shake tubes at 250 rpm for 1 hour at 37° C. Plate 100 ul of transformed cells on Luria Broth plates (RPI Corp, Mt. Prospect, Ill., USA) plus appropriate antibiotics depending on the pSMART vector used. Incubate plates overnight at 37° C.

For Ligations into StrataClone:

Gel extracted DNA is blunted using PCRTerminator (Lucigen Corp, Middleton, Wis., USA) according to manufacturer's instructions. Then 2 ul of DNA is added to 3 ul StrataClone Blunt Cloning buffer and 1 ul StrataClone Blunt vector mix amp/kan (Stratagene, La Jolla, Calif., USA) for a total of 6 ul. Mix the reaction by gently pipeting up at down and incubate the reaction at room temperature for 30 minutes then place onto ice. Thaw a tube of StrataClone chemically competent cells (Stratagene, La Jolla, Calif., USA) on ice for 20 minutes. Add 1 ul of the cloning reaction to the tube of chemically competent cells and gently mix with a pipette tip and incubate on ice for 20 minutes. Heat shock the transformation at 42° C. for 45 seconds then put on ice for 2 minutes. Add 250 ul pre-warmed Luria Broth (RPI Corp, Mt. Prospect, Ill., USA) and shake at 250 rpm for 37° C. for 2 hour. Plate 100 ul of the transformation mixture onto Luria Broth plates (RPI Corp, Mt. Prospect, Ill., USA) plus appropriate antibiotics. Incubate plates overnight at 37° C.

For Ligations into pCR2.1-TOPO TA:

Add 1 ul TOPO vector, 1 ul Salt Solution (Invitrogen Corp, Carlsbad, Calif., USA) and 3 ul gel extracted DNA into a microcentrifuge tube. Allow the tube to incubate at room temperature for 30 minutes then place the reaction on ice. Thaw one tube of TOP10F' chemically competent cells (Invitrogen Corp, Carlsbad, Calif., USA) per reaction. Add 1 ul of reaction mixture into the thawed TOP10F' cells and mix gently by swirling the cells with a pipette tip and incubate on ice for 20 minutes. Heat shock the transformation at 42° C. for 45 seconds then put on ice for 2 minutes. Add 250 ul pre-warmed SOC media (Invitrogen Corp, Carlsbad, Calif., USA) and shake at 250 rpm for 37° C. for 1 hour. Plate 100 ul of the transformation mixture onto Luria Broth plates (RPI Corp, Mt. Prospect, Ill., USA) plus appropriate antibiotics. Incubate plates overnight at 37° C.

General Transformation and Related Culture Methodologies:

Chemically competent transformation protocols are carried out according to the manufactures instructions or according to the literature contained in *Molecular Cloning* (Sambrook and Russell). Generally, plasmid DNA or ligation products are chilled on ice for 5 to 30 min. in solution with chemically competent cells. Chemically competent cells are a widely used product in the field of biotechnology and are available from multiple vendors, such as those indicated above in this Subsection. Following the chilling period cells generally are heat-shocked for 30 seconds at 42° C. without shaking, re-chilled and combined with 250 microliters of rich media, such as S.O.C. Cells are then incubated at 37° C. while shaking at 250 rpm for 1 hour. Finally, the cells are screened for successful transformations by plating on media containing the appropriate antibiotics.

The choice of an *E. coli* host strain for plasmid transformation is determined by considering factors such as plasmid stability, plasmid compatibility, plasmid screening methods and protein expression. Strain backgrounds can be changed by simply purifying plasmid DNA as described above and transforming the plasmid into a desired or otherwise appropriate *E. coli* host strain such as determined by experimental necessities, such as any commonly used cloning strain (e.g., DH5a, Top1OF', *E. coli* 10G, etc.)

To make 1L M9 minimal media:

M9 minimal media was made by combining 5× M9 salts, 1M $MgSO_4$, 20% glucose, 1M $CaCl_2$ and sterile deionized water. The 5× M9 salts are made by dissolving the following salts in deionized water to a final volume of 1L: 64 g $Na_2HPO_4 7H_2O$, 15 g $KH_2PO_4$, 2.5 g NaCl, 5.0 g $NH_4Cl$. The salt solution was divided into 200 mL aliquots and sterilized by autoclaving for 15 minutes at 15 psi on the liquid cycle. A 1M solution of $MgSO_4$ and 1M $CaCl_2$ were made separately, then sterilized by autoclaving. The glucose was filter sterilized by passing it thought a 0.22 μm filter. All of the components are combined as follows to make 1L of M9: 750 mL sterile water, 200 mL 5× M9 salts, 2 mL of 1M $MgSO_4$, 20 mL 20% glucose, 0.1 mL $CaCl_2$, Q.S. to a final volume of 1L.

To Make EZ Rich Media:

All media components were obtained from TEKnova (Hollister Calif. USA) and combined in the following volumes. 100 mL 10× MOPS mixture, 10 mL 0.132M $K_2HPO_4$, 100 mL 10× ACGU, 200 mL 5× Supplement EZ, 10 mL 20% glucose, 580 mL sterile water.

Subsection III. Additional Methods Related to Enzyme Evaluation Expression and Purification of proteins expressed in pKK223-Cterm-5×his by Expression Plasmids Transformants containing a gene cloned into the pKK223-Cterm-5×his expression vector were grown overnight in LB+0.2% glucose+200 ug/mL Ampicillin, diluted 1:20 and grown (LB+0.2% glucose+200 ug/mL Ampicillin) to OD600 of 0.4. IPTG was added at 1 mM final concentration to induce protein expression. Cultures were then allowed to grow at 37 degrees C. for four hours. Cells were harvested by centrifugation at 4 degrees C. for 10 minutes at 4000 rpm. Pellets were resuspended and concentrated 50× (e.g. pellet from 500 mL culture resuspended in 10 mL buffer) in Qiagen Ni-NTA Lysis Buffer (50 mM Na2HPO4, 300 mM NaCl, 10 mM imidazole, pH 8.0)+1 mM PMSF. Lysozyme was added to a final concentration of 1 mg/mL; cells were incubated on ice for 30 minutes. Cells were lysed using a French Press (cell pressure=2000 psi) three times. Lysates were cleared by centrifugation at 4 degrees C. for 20 minutes, applied to Qiagen Ni-NTA columns, washed and eluted as specified by Qiagen (cat. #31314). Samples were analyzed by SDS-PAGE by routine protocols.

Decarboxylation Enzyme Reactions:

100 uL reaction mixtures were added to microwells. Each 100 uL of reaction mixture contained 50 mM Potassium Phosphate (pH 7.0), 0.2 mM TPP, 1 mM $MgCl_2$, and 10 mM of the appropriate substrate. 300 pg of purified enzyme was added to a respective microwell and incubated 16 hours at 37 degrees C. After 16 hours at 37 degrees C., 100 uL of Purpald® colorimetric indicator (Sigma-Aldrich, cat. #162892), prepared per manufacturer's instructions, was added to each microwell in order to detect formation of corresponding aldehyde product. After addition of the Purpald®, the microwells were incubated at room temperature for 1 hour and read at a wavelength of 540 nm in a Thermomax Microplate Reader (Molecular Devices) using SOFTMax Pro Microplate Reader software, Ver. 4.0.

Summary of Suppliers Section

The names and city addresses of major suppliers are provided in the methods above. In addition, as to Qiagen products, the DNeasy® Blood and Tissue Kit, Cat. No. 69506, is used in the methods for genomic DNA preparation; the QIAprep® Spin ("mini prep"), Cat. No. 27106, is used for plasmid DNA purification, and the QIAquick® Gel Extraction Kit, Cat. No. 28706, is used for gel extractions as described above.

Bio-production Media

Bio-production media, which is used in the present invention with recombinant microorganisms having a biosynthetic pathway for 3-HP (and optionally products further downstream of 3-HP), must contain suitable carbon substrates. Suitable substrates may include, but are not limited to, monosaccharides such as glucose and fructose, oligosaccharides such as lactose or sucrose, polysaccharides such as starch or cellulose or mixtures thereof and unpurified mixtures from renewable feed stocks such as cheese whey permeate, cornsteep liquor, sugar beet molasses, and barley malt. Additionally the carbon substrate may also be one-carbon substrates such as carbon dioxide, or methanol for which metabolic conversion into key biochemical intermediates has been demonstrated. In addition to one and two carbon substrates methylotrophic organisms are also known to utilize a number of other carbon containing compounds such as methylamine, glucosamine and a variety of amino acids for metabolic activity. For example, methylotrophic yeast are known to utilize the carbon from methylamine to form trehalose or glycerol (Bellion et al., Microb. Growth C1 Compd., [Int. Symp.], 7th (1993), 415-32. Editor(s): Murrell, J. Collin; Kelly, Don P. Publisher: Intercept, Andover, UK). Similarly, various species of Candida will metabolize alanine or oleic acid (Sulter et al., Arch. Microbiol. 153:485-489 (1990)). Hence it is contemplated that the source of carbon utilized in the present invention may encompass a wide variety of carbon containing substrates and will only be limited by the choice of organism. Although it is contemplated that all of the above mentioned carbon substrates and mixtures thereof are suitable in the present invention as a carbon source, common carbon substrates used as carbon sources are glucose, fructose, and sucrose, as well as mixtures of any of these sugars. Sucrose may be obtained from feed stocks such as sugar cane, sugar beets, cassava, and sweet sorghum. Glucose and dextrose may be obtained through saccharification of starch based feed stocks including grains such as corn, wheat, rye, barley, and oats.

In addition, sugars may be obtained from cellulosic and lignocellulosic biomass through processes of pretreatment and saccharification, as described, for example, in US patent application US20070031918A1, which is herein incorporated by reference. Biomass refers to any cellulosic or lignocellulosic material and includes materials comprising cellulose, and optionally further comprising hemicellulose, lignin, starch, oligosaccharides and/or monosaccharides. Biomass may also comprise additional components, such as protein and/or lipid. Biomass may be derived from a single source, or biomass can comprise a mixture derived from more than one source; for example, biomass could comprise a mixture of corn cobs and corn stover, or a mixture of grass and leaves. Biomass includes, but is not limited to, bioenergy crops, agricultural residues, municipal solid waste, industrial solid waste, sludge from paper manufacture, yard waste, wood and forestry waste. Examples of biomass include, but are not limited to, corn grain, corn cobs, crop residues such as corn husks, corn stover, grasses, wheat, wheat straw, barley, barley straw, hay, rice straw, switchgrass, waste paper, sugar cane bagasse, sorghum, soy, components obtained from milling of grains, trees, branches, roots, leaves, wood chips, sawdust, shrubs and bushes, vegetables, fruits, flowers and animal manure. Any such biomass may be used in a bio-production method or system to provide a carbon source. In addition to an appropriate carbon source, such as selected from one of the above-disclosed types, bio-production media must contain suitable minerals, salts, cofactors, buffers and other components, known to those skilled in the art, suitable for the growth of the cultures and promotion of the enzymatic pathway necessary for 3-HP (and optionally products further downstream of 3-HP) production.

Culture Conditions

Typically cells are grown at a temperature in the range of about 25° C. to about 40° C. in an appropriate medium. Suitable growth media in the present invention are common commercially prepared media such as Luria Bertani (LB) broth, M9 minimal media, Sabouraud Dextrose (SD) broth, Yeast medium (YM) broth or (Ymin) yeast synthetic minimal media. Other defined or synthetic growth media may also be used, and the appropriate medium for growth of the particular microorganism will be known by one skilled in the art of microbiology or bio-production science.

Suitable pH ranges for the bio-production are between pH 5.0 to pH 9.0, where pH 6.0 to pH 8.0 is a typical pH range for the initial condition.

Bio-productions may be performed under aerobic, microaerobic, or anaerobic conditions, with or without agitation.

The amount of 3-HP (and optionally products further downstream of 3-HP) produced in a bio-production media generally can be determined using a number of methods known in the art, for example, high performance liquid chromatography (HPLC) or gas chromatography (GC). Specific HPLC methods for the specific examples are provided herein.

Bio-production Reactors and Systems:

Any of the recombinant microorganisms as described and/or referred to above may be introduced into an industrial bio-production system where the microorganisms convert a carbon source into 3-HP (and optionally products further downstream of 3-HP) in a commercially viable operation. The bio-production system includes the introduction of such a recombinant microorganism into a bioreactor vessel, with a carbon source substrate and bio-production media suitable for growing the recombinant microorganism, and maintaining the bio-production system within a suitable temperature range (and dissolved oxygen concentration range if the reaction is aerobic or microaerobic) for a suitable time to obtain a desired conversion of a portion of the substrate molecules to 3-HP (and optionally products further downstream of 3-HP). Industrial bio-production systems and their operation are well-known to those skilled in the arts of chemical engineering and bioprocess engineering. The following paragraphs provide an overview of the methods and aspects of industrial systems that may be used for the bio-production of 3-HP (and optionally products further downstream of 3-HP).

In various embodiments, any of a wide range of sugars, including, but not limited to sucrose, glucose, xylose, cellulose or hemicellulose, are provided to a microorganism, such as in an industrial system comprising a reactor vessel in which a defined media (such as a minimal salts media including but not limited to M9 minimal media, potassium sulfate minimal media, yeast synthetic minimal media and many others or variations of these), an inoculum of a microorganism providing one or more of the 3-HP (and optionally products further downstream of 3-HP) biosynthetic pathway alternatives, and the a carbon source may be combined. The carbon source enters the cell and is cataboliized by well-known and common metabolic pathways to yield common metabolic intermediates, including phosphoenolpyruvate (PEP). (See Molecular Biology of the Cell, $3^{rd}$ Ed., B. Alberts et al. Garland Publishing, New York, 1994, pp. 42-45, 66-74, incorporated by reference for the teachings of basic metabolic catabolic pathways for sugars; Principles of Biochemistry, $3^{rd}$ Ed., D. L. Nelson & M. M. Cox, Worth Publishers, New York, 2000, pp 527-658, incorporated by reference for the teachings of major metabolic pathways; and Biochemistry, $4^{th}$ Ed., L. Stryer, W. H. Freeman and Co., New York, 1995, pp. 463-650, also incorporated by reference for the teachings of major metabolic pathways.). Further to types of industrial bio-production, various embodiments of the present invention may employ a batch type of industrial bioreactor. A classical batch bioreactor system is considered "closed" meaning that the composition of the medium is established at the beginning of a respective bio-production event and not subject to artificial alterations and additions during the time period ending substantially with the end of the bio-production event. Thus, at the beginning of the bio-production event the medium is inoculated with the desired organism or organisms, and bio-production is permitted to occur without adding anything to the system. Typically, however, a "batch" type of bio-production event is batch with respect to the addition of carbon source and attempts are often made at controlling factors such as pH and oxygen concentration. In batch systems the metabolite and biomass compositions of the system change constantly up to the time the bio-production event is stopped. Within batch cultures cells moderate through a static lag phase to a high growth log phase and finally to a stationary phase where growth rate is diminished or halted. If untreated, cells in the stationary phase will eventually die. Cells in log phase generally are responsible for the bulk of production of a desired end product or intermediate.

A variation on the standard batch system is the Fed-Batch system. Fed-Batch bio-production processes are also suitable in the present invention and comprise a typical batch system with the exception that the substrate is added in increments as the bio-production progresses. Fed-Batch systems are useful when catabolite repression is apt to inhibit the metabolism of the cells and where it is desirable to have limited amounts of substrate in the media. Measurement of the actual substrate concentration in Fed-Batch systems may be measured directly, such as by sample analysis at different times, or estimated on the basis of the changes of measurable factors such as pH, dissolved oxygen and the partial pressure of waste gases such as $CO_2$. Batch and Fed-Batch approaches are common and well known in the art and examples may be found in Thomas D. Brock in Biotechnology: A Textbook of Industrial Microbiology, Second Edition (1989) Sinauer Associates, Inc., Sunderland, Mass., Deshpande, Mukund V., Appl. Biochem. Biotechnol., 36:227, (1992), and Biochemical Engineering Fundamentals, $2^{nd}$ Ed. J. E. Bailey and D. F. Ollis, McGraw Hill, New York, 1986, herein incorporated by reference for general instruction on bio-production, which as used herein may be aerobic, microaerobic, or anaerobic.

Although the present invention may be performed in batch mode, as provided in Example 8, or in fed-batch mode, it is contemplated that the method would be adaptable to continuous bio-production methods. Continuous bio-production is considered an "open" system where a defined bio-production medium is added continuously to a bioreactor and an equal amount of conditioned media is removed simultaneously for processing. Continuous bio-production generally maintains the cultures within a controlled density range where cells are primarily in log phase growth. Two types of continuous bioreactor operation include: 1) Chemostat—where fresh media is fed to the vessel while simultaneously removing an equal rate of the vessel contents. The limitation of this approach is that cells are lost and high cell density generally is not achievable. In fact, typically one can obtain much higher cell density with a fed-batch process. 2) Perfusion culture, which is similar to the chemostat approach except that the stream that is removed from the vessel is subjected to a separation technique which recycles viable cells back to the vessel. This type of continuous bioreactor operation has been shown to yield significantly higher cell densities than fed-batch and can be operated continuously. Continuous bio-production is particularly advantageous for industrial operations because it has less down time associated with draining, cleaning and preparing the equipment for the next bio-production event. Furthermore, it is typically more economical to continuously operate downstream unit operations, such as distillation, than to run them in batch mode.

Continuous bio-production allows for the modulation of one factor or any number of factors that affect cell growth or end product concentration. For example, one method will maintain a limiting nutrient such as the carbon source or nitrogen level at a fixed rate and allow all other parameters to moderate. In other systems a number of factors affecting growth can be altered continuously while the cell concentration, measured by media turbidity, is kept constant. Continuous systems strive to maintain steady state growth conditions and thus the cell loss due to the medium being drawn off must be balanced against the cell growth rate in the bio-production. Methods of modulating nutrients and growth factors for continuous bio-production processes as well as techniques for maximizing the rate of product formation are well known in the art of industrial microbiology and a variety of methods are detailed by Brock, supra.

It is contemplated that embodiments of the present invention may be practiced using either batch, fed-batch or continuous processes and that any known mode of bio-production would be suitable. Additionally, it is contemplated that cells may be immobilized on an inert scaffold as whole cell catalysts and subjected to suitable bio-production conditions for 3-HP (and optionally products further downstream of 3-HP) production.

The following published resources are incorporated by reference herein for their respective teachings to indicate the level of skill in these relevant arts, and as needed to support a disclosure that teaches how to make and use methods of industrial bio-production of 3-HP (and optionally products further downstream of 3-HP) from sugar sources, and also industrial systems that may be used to achieve such conversion with any of the recombinant microorganisms of the present invention (Biochemical Engineering Fundamentals, $2^{nd}$ Ed. J. E. Bailey and D. F. Ollis, McGraw Hill, New York, 1986, entire book for purposes indicated and Chapter 9, pages 533-657 in particular for biological reactor design; Unit Operations of Chemical Engineering, $5^{th}$ Ed., W. L. McCabe et al., McGraw Hill, New York 1993, entire book for purposes indicated, and particularly for process and separation technologies analyses; Equilibrium Staged Separations, P. C. Wankat, Prentice Hall, Englewood Cliffs, N.J. USA, 1988, entire book for separation technologies teachings).

The scope of the present invention is not meant to be limited to the exact sequences provided herein. It is appreciated that a range of modifications to nucleic acid and to amino acid sequences may be made and still provide a desired functionality. The following discussion is provided to more clearly define ranges of variation that may be practiced and still remain within the scope of the present invention.

It is recognized in the art that some amino acid sequences of the present invention can be varied without significant effect of the structure or function of the proteins disclosed herein. Variants included can constitute deletions, insertions, inversions, repeats, and type substitutions so long as the indicated enzyme activity is not significantly affected. Guidance concerning which amino acid changes are likely to be phenotypically silent can be found in Bowie, J. U., et Al., "Deciphering the Message in Protein Sequences: Tolerance to Amino Acid Substitutions," Science 247:1306-1310 (1990).

In various embodiments polypeptides obtained by the expression of the polynucleotide molecules of the present invention may have at least approximately 80%, 90%, 95%, 96%, 97%, 98%, 99% or 100% identity to one or more amino acid sequences encoded by the genes and/or nucleic acid sequences described herein for the 3-HP (and optionally products further downstream of 3-HP) biosynthesis pathways. A truncated respective polypeptide has at least about 90% of the full length of a polypeptide encoded by a nucleic acid sequence encoding the respective native enzyme, and more particularly at least 95% of the full length of a polypeptide encoded by a nucleic acid sequence encoding the respective native enzyme. By a polypeptide having an amino acid sequence at least, for example, 95% "identical" to a reference amino acid sequence of a polypeptide is intended that the amino acid sequence of the claimed polypeptide is identical to the reference sequence except that the claimed polypeptide sequence can include up to five amino acid alterations per each 100 amino acids of the reference amino acid of the polypeptide. In other words, to obtain a polypeptide having an amino acid sequence at least 95% identical to a reference amino acid sequence, up to 5% of the amino acid residues in the reference sequence can be deleted or substituted with another amino acid, or a number of amino acids up to 5% of the total amino acid residues in the reference sequence can be inserted into the reference sequence. These alterations of the reference sequence can occur at the amino or carboxy terminal positions of the reference amino acid sequence or anywhere between those terminal positions, interspersed either individually among residues in the reference sequence or in one or more contiguous groups within the reference sequence.

As a practical matter, whether any particular polypeptide is at least 80%, 85%, 90%, 92%, 95%, 96%, 97%, 98% or 99% identical to any reference amino acid sequence of any polypeptide described herein (which may correspond with a particular nucleic acid sequence described herein), such particular polypeptide sequence can be determined conventionally using known computer programs such the Bestfit program (Wisconsin Sequence Analysis Package, Version 8 for Unix, Genetics Computer Group, University Research Park, 575 Science Drive, Madison, Wis. 53711). When using Bestfit or any other sequence alignment program to determine whether a particular sequence is, for instance, 95% identical to a reference sequence according to the present invention, the parameters are set, of course, such that the percentage of identity is calculated over the full length of the reference amino acid sequence and that gaps in homology of up to 5% of the total number of amino acid residues in the reference sequence are allowed. For example, in a specific embodiment the identity between a reference sequence (query sequence, a sequence of the present invention) and a subject sequence, also referred to as a global sequence alignment, may be determined using the FASTDB computer program based on the algorithm of Brutlag et al. (Comp. App. Biosci. 6:237-245 (1990)). Preferred parameters used in a FASTDB amino acid alignment are: Matrix=PAM 0, k-tuple=2, Mismatch Penalty=1, Joining Penalty=20, Randomization Group Length=0, Cutoff Score=1, Window Size=sequence length, Gap Penalty=5, Gap Size Penalty=0.05, Window Size=500 or the length of the subject amino acid sequence, whichever is shorter. According to this embodiment, if the subject sequence is shorter than the query sequence due to N- or C-terminal deletions, not because of internal deletions, a manual correction is made to the results to take into consideration the fact that the FASTDB program does not account for N- and C-terminal truncations of the subject sequence when calculating global percent identity. For subject sequences truncated at the N- and C-termini, relative to the query sequence, the percent identity is corrected by calculating the number of residues of the query sequence that are N- and C-terminal of the subject sequence, which are not matched/aligned with a corresponding subject residue, as a percent of the total bases of the query sequence. A determination of whether a residue is matched/aligned is determined by results of the FASTDB sequence alignment. This percentage is then subtracted from the percent identity, calculated by the above FASTDB program using the specified parameters, to arrive at a final percent identity score. This final percent identity score is what is used for the purposes of this embodiment. Only residues to the N- and C-termini of the subject sequence, which are not matched/aligned with the query sequence, are considered for the purposes of manually adjusting the percent identity score. That is, only query residue positions outside the farthest N- and C-terminal residues of the subject sequence. For example, a 90 amino acid residue subject sequence is aligned with a 100 residue query sequence to determine percent identity. The deletion occurs at the N-terminus of the subject sequence and therefore, the FASTDB alignment does not show a matching/alignment of the first 10 residues at the N-terminus. The 10 unpaired residues represent 10% of the sequence (number of residues at the N- and C-termini not matched/total number of residues in the query sequence) so 10% is subtracted from the percent identity score calculated by the FASTDB program. If the remaining 90 residues were perfectly matched the final percent identity would be 90%. In another example, a 90 residue subject sequence is compared with a 100 residue query sequence. This time the deletions are internal deletions so there are no residues at the N- or C-termini of the subject sequence which are not matched/aligned with the query. In this case the percent identity calculated by FASTDB is not manually corrected. Once again, only residue positions outside the N- and C-terminal ends of the subject sequence, as displayed in the FASTDB alignment, which are not matched/aligned with the query sequence are manually corrected for.

The above descriptions and methods for sequence homology are intended to be exemplary and it is recognized that this concept is well-understood in the art. Further, it is appreciated that nucleic acid sequences may be varied and still provide a functional enzyme, and such variations are within the scope of the present invention. Nucleic acid sequences that encode polypeptides that provide the indicated functions for 3-HP (and optionally products further downstream of 3-HP) that increase tolerance or production are considered within the scope of the present invention. These may be further defined by the stringency of hybridization, described below, but this is not meant to be limiting when a function of an encoded polypeptide matches a specified 3-HP (and optionally products further downstream of 3-HP) tolerance-related or biosynthesis pathway enzyme activity.

Further to nucleic acid sequences, "hybridization" refers to the process in which two single-stranded polynucleotides bind non-covalently to form a stable double-stranded polynucleotide. The term "hybridization" may also refer to triple-stranded hybridization. The resulting (usually) double-stranded polynucleotide is a "hybrid" or "duplex." "Hybridization conditions" will typically include salt concentrations of less than about 1M, more usually less than about 500 mM and less than about 200 mM. Hybridization temperatures can be as low as 5° C., but are typically greater than 22° C., more typically greater than about 30° C., and often are in excess of about 37° C. Hybridizations are usually performed under stringent conditions, i.e. conditions under which a probe will hybridize to its target subsequence. Stringent conditions are sequence-dependent and are different in different circumstances. Longer fragments may require higher hybridization temperatures for specific hybridization. As other factors may affect the stringency of hybridization, including base composition and length of the complementary strands, presence of organic solvents and extent of base mis-matching, the combination of parameters is more important than the absolute measure of any one alone. Generally, stringent conditions are selected to be about 5° C. lower than the $T_m$ for the specific sequence at a defined ionic strength and pH. Exemplary stringent conditions include salt concentration of at least 0.01 M to no more than 1 M Na ion concentration (or other salts) at a pH 7.0 to 8.3 and a temperature of at least 25° C. For example, conditions of 5×SSPE (750 mM NaCl, 50 mM NaPhosphate, 5 mM EDTA, pH 7.4) and a temperature of 25-30° C. are suitable for allele-specific probe hybridizations. For stringent conditions, see for example, Sambrook and Russell and Anderson "Nucleic Acid Hybridization" 1$^{st}$ Ed., BIOS Scientific Publishers Limited (1999), which are hereby incorporated by reference for hybridization protocols. "Hybridizing specifically to" or "specifically hybridizing to" or like expressions refer to the binding, duplexing, or hybridizing of a molecule substantially to or only to a particular nucleotide sequence or sequences under stringent conditions when that sequence is present in a complex mixture (e.g., total cellular) DNA or RNA.

Having so described the present invention and provided examples, and further discussion, and in view of the above paragraphs, it is appreciated that various non-limiting aspects of the present invention may include:

A genetically modified (recombinant) microorganism comprising a nucleic acid sequence that encodes a polypeptide with at least 85% amino acid sequence identity to any of the enzymes of any of 3-HP tolerance-related or biosynthetic pathways, wherein the polypeptide has enzymatic activity effective to perform the enzymatic reaction of the respective 3-HP biosynthetic pathway enzyme, and the recombinant microorganism exhibits greater 3-H tolerance and/or 3-HP bio-production.

A genetically modified (recombinant) microorganism comprising a nucleic acid sequence that encodes a polypeptide with at least 90% amino acid sequence identity to any of the enzymes of any of 3-HP tolerance-related or biosynthetic pathways, wherein the polypeptide has enzymatic activity effective to perform the enzymatic reaction of the respective 3-HP tolerance-related or biosynthetic pathway enzyme, and the recombinant microorganism exhibits greater 3-HP tolerance and/or 3-HPbio-production.

A genetically modified (recombinant) microorganism comprising a nucleic acid sequence that encodes a polypeptide with at least 95% amino acid sequence identity to any of the enzymes of any of 3-HP tolerance-related or biosynthetic pathways, wherein the polypeptide has enzymatic activity effective to perform the enzymatic reaction of the respective 3-HP tolerance-related or biosynthetic pathway enzyme, and the recombinant microorganism exhibits greater 3-HPtolerance and/or 3-HP bio-production.

The above paragraphs are meant to indicate modifications in the nucleic acid sequences may be made and a respective polypeptide encoded there from remains functional so as to perform an enzymatic catalysis along one of the 3-HP tolerance-related and/or biosynthetic pathways described above.

The term "heterologous DNA," "heterologous nucleic acid sequence," and the like as used herein refers to a nucleic acid sequence wherein at least one of the following is true: (a) the sequence of nucleic acids is foreign to (i.e., not naturally found in) a given host microorganism; (b) the sequence may be naturally found in a given host microorganism, but in an unnatural (e.g., greater than expected) amount; or (c) the sequence of nucleic acids comprises two or more subsequences that are not found in the same relationship to each other in nature. For example, regarding instance (c), a heterologous nucleic acid sequence that is recombinantly produced will have two or more sequences from unrelated genes arranged to make a new functional nucleic acid. Embodiments of the present invention may result from introduction of an expression vector into a host microorganism, wherein the expression vector contains a nucleic acid sequence coding for an enzyme that is, or is not, normally found in a host microorganism. With reference to the host microorganism's genome, then, the nucleic acid sequence that codes for the enzyme is heterologous.

Also, and more generally, in accordance with examples and embodiments herein, there may be employed conventional molecular biology, cellular biology, microbiology, and recombinant DNA techniques within the skill of the art. Such techniques are explained fully in the literature. (See, e.g., Sambrook and Russell, Molecular Cloning: A Laboratory Manual, Third Edition 2001 (volumes 1-3), Cold Spring Harbor Laboratory Press, Cold Spring Harbor, N.Y.; Animal Cell Culture, R. I. Freshney, ed., 1986). These published resources are incorporated by reference herein for their respective teachings of standard laboratory methods found therein. Further, all patents, patent applications, patent publications, and other publications referenced herein (collectively, "published resource(s)") are hereby incorporated by reference in this application. Such incorporation, at a minimum, is for the specific teaching and/or other purpose that may be noted when citing the reference herein. If a specific teaching and/or other purpose is not so noted, then the published resource is specifically incorporated for the teaching(s) indicated by one or more of the title, abstract, and/or summary of the reference. If no such specifically identified teaching and/or other purpose may be so relevant, then the published resource is incorporated in order to more fully describe the state of the art to which the present invention pertains, and/or to provide such teachings as are generally known to those skilled in the art, as may be applicable. However, it is specifically stated that a citation of a published resource herein shall not be construed as an admission that such is prior art to the present invention.

Thus, based on the above disclosure, it is appreciated that within the scope of the present invention are methods for selection and identification of mutant polynucleotides comprising nucleic acid sequences that encode mutant polypeptides that demonstrate elevated activity of oxaloacetate alpha-oxo decarboxylase activity (also referred to herein as oxaloacetate alpha-decarboxylase activity). Also within the scope of the present invention may be compositions that comprise such identified mutant polynucleotides and polypeptides. In various embodiments, these methods are directed for the specific purpose of obtaining recombinant microorganisms that have capacity for increased bio-production of 3-HP. Although specific genes, enzymes, plasmids and other constructs are described in the above examples, these are not meant to limit the scope of the invention, particularly in view of the level of skill in the art.

Thus, while various embodiments of the present invention have been shown and described herein, it will be obvious that such embodiments are provided by way of example only. Numerous variations, changes and substitutions may be made without departing from the invention herein in its various embodiments. Specifically, and for whatever reason, for any grouping of compounds, nucleic acid sequences, polypeptides including specific proteins including functional enzymes, metabolic pathway enzymes or intermediates, elements, or other compositions, or concentrations stated or otherwise presented herein in a list, table, or other grouping (such as metabolic pathway enzymes shown in a figure), unless clearly stated otherwise, it is intended that each such grouping provides the basis for and serves to identify various subset embodiments, the subset embodiments in their broadest scope comprising every subset of such grouping by exclusion of one or more members (or subsets) of the respective stated grouping. Moreover, when any range is described herein, unless clearly stated otherwise, that range includes all values therein and all sub-ranges therein. Accordingly, it is intended that the invention be limited only by the spirit and scope of appended claims, and of later claims, and of either such claims as they may be amended during prosecution of this or a later application claiming priority hereto.

What is claimed is:

1. A method for producing an acrylic acid-based consumer product, said method comprising the steps of:
   i) combining a carbon source and a cell culture to produce 3-hydroxypropionic acid, wherein said cell culture comprises a genetically modified *Escherichia coli* (*E. coli*) microorganism comprising a heterologous nucleic acid encoding for a protein with malonyl-CoA reductase activity; and wherein said genetically modified *E. coli* microorganism further comprises reduction in activity of pyruvate formate-lyase;
   ii) growing said cell culture in feed-batch, batch mode, or continuous batch mode production;
   iii) converting said 3-hydroxypropionic acid to acrylic acid;
   iv) polymerizing acrylic acid into a polymer of acrylate; and
   v) processing said polymer of acrylate into a consumer product.

2. The method of claim 1, wherein said microorganism is further modified for increased tolerance to 3-hydroxypropionic acid.

3. The method of claim 1, wherein said genetically modified *E. coli* microorganism further comprises reduction in activity of lactate dehydrogenase, phosphate acetyltransferase, and pyruvate oxidase.

4. The method of claim 1, wherein said genetically modified *E. coli* microorganism further comprises a modification in a malonyl-CoA reductase enzyme, wherein the malonyl-CoA reductase enzyme comprises a molecule with at least 90% sequence identity to SEQ ID NO: 11.

5. A consumer product produced according to the following steps:
   i) combining a carbon source and a cell culture to produce 3-hydroxypropionic acid, wherein said cell culture comprises a genetically modified *Escherichia coil* microorganism comprising a heterologous nucleic acid encoding for a protein with malonyl-CoA reductase activity; and wherein said genetically modified *E. coli* microorganism further comprises reduction in activity of pyruvate formate-lyase;
   ii) growing said cell culture in feed-batch, batch mode, or continuous batch mode production;
   iii) converting said 3-hydroxypropionic acid to acrylic acid;
   iv) polymerizing acrylic acid into a polymer of acrylate; and
   v) processing said polymer of acrylate into a consumer product.

6. The method of claim 1, wherein the polymer of acrylate is selected from the group consisting of methyl acrylate, butyl acrylate, ethyl acrylate, and polyacrylic acid.

7. The method of claim 1, wherein the polymer of acrylate is butyl acrylate.

8. The method of claim 1, wherein the polymer of acrylate is ethyl acrylate.

9. The method of claim 1, wherein the consumer product is selected from the group consisting of: paints, coatings, plastics, adhesives, dispersives, textiles, or leather.

10. The method of claim 1, wherein the cell culture has increased 3-HP production greater than about 40 g/L of biomass/cell culture.

11. The method of claim 1, wherein the cell culture has increased 3-HP production greater than about 60 g/L of biomass/cell culture.

12. The method of claim 1, wherein the cell culture has increased 3-HP production greater than about 85 g/L of biomass/cell culture.

13. The method of claim 1, wherein said genetically modified *E. coli* microorganism further comprises reduction in activity of a lactate dehydrogenase.

14. The method of claim 1, wherein said genetically modified *E. coli* microorganism further comprises reduction in activity of a phosphate acetyltransferase.

15. The method of claim 1, wherein said genetically modified *E. coli* microorganism further comprises reduction in activity of a pyruvate oxidase.

* * * * *